(12) United States Patent
Angros

(10) Patent No.: US 9,170,179 B2
(45) Date of Patent: Oct. 27, 2015

(54) METHOD OF REMOVING FLOATATION LIQUID

(71) Applicant: Lee H. Angros, Bethany, OK (US)

(72) Inventor: Lee H. Angros, Bethany, OK (US)

( * ) Notice: Subject to any disclaimer, the term of this patent is extended or adjusted under 35 U.S.C. 154(b) by 0 days.

(21) Appl. No.: 14/216,071

(22) Filed: Mar. 17, 2014

(65) Prior Publication Data

US 2014/0287456 A1   Sep. 25, 2014

Related U.S. Application Data

(60) Provisional application No. 61/791,178, filed on Mar. 15, 2013.

(51) Int. Cl.
| | | |
|---|---|---|
| *G01N 1/28* | (2006.01) | |
| *G01N 1/36* | (2006.01) | |
| *G01N 1/31* | (2006.01) | |
| *G01N 1/30* | (2006.01) | |

(52) U.S. Cl.
CPC .................. *G01N 1/36* (2013.01); *G01N 1/312* (2013.01); *G01N 1/30* (2013.01)

(58) Field of Classification Search
USPC ....................................................... 435/40.52
See application file for complete search history.

(56) References Cited

U.S. PATENT DOCUMENTS

| 4,158,709 | A  | * | 6/1979 | Tsaknis et al. ............... 427/2.11 |
|---|---|---|---|---|
| 5,318,795 | A  |   | 6/1994 | Stokes et al. |
| 5,948,685 | A  | * | 9/1999 | Angros ........................... 436/63 |
| 8,192,994 | B2 | * | 6/2012 | Angros ........................... 436/63 |
| 8,377,377 | B2 | * | 2/2013 | Angros ........................... 422/64 |
| 8,470,109 | B2 | * | 6/2013 | Angros ........................... 156/64 |
| 2009/0155907 | A1 | | 6/2009 | Winther et al. |
| 2010/0068757 | A1 | | 3/2010 | Angros |
| 2011/0190153 | A1 | | 8/2011 | Adey et al. |

FOREIGN PATENT DOCUMENTS

WO     2010/078214     7/2010

OTHER PUBLICATIONS

International Search Report and Written Opinion (PCT/US2014/030409); Aug. 21, 2014.

* cited by examiner

*Primary Examiner* — Ralph Gitomer
(74) *Attorney, Agent, or Firm* — Dunlap Codding, P.C.

(57) ABSTRACT

A method of removing a floatation liquid from between a microscope slide and a paraffin embedded biological specimen including position the microscope slide with the paraffin embedded biological specimen floated thereon onto a slide support element. The slide support element is rotated to cause the microscope slide and the paraffin embedded biological specimen to turn in a way that causes the floatation liquid disposed between the microscope slide and the paraffin embedded biological specimen to be drawn from between the microscope slide and the paraffin embedded biological specimen.

53 Claims, 43 Drawing Sheets

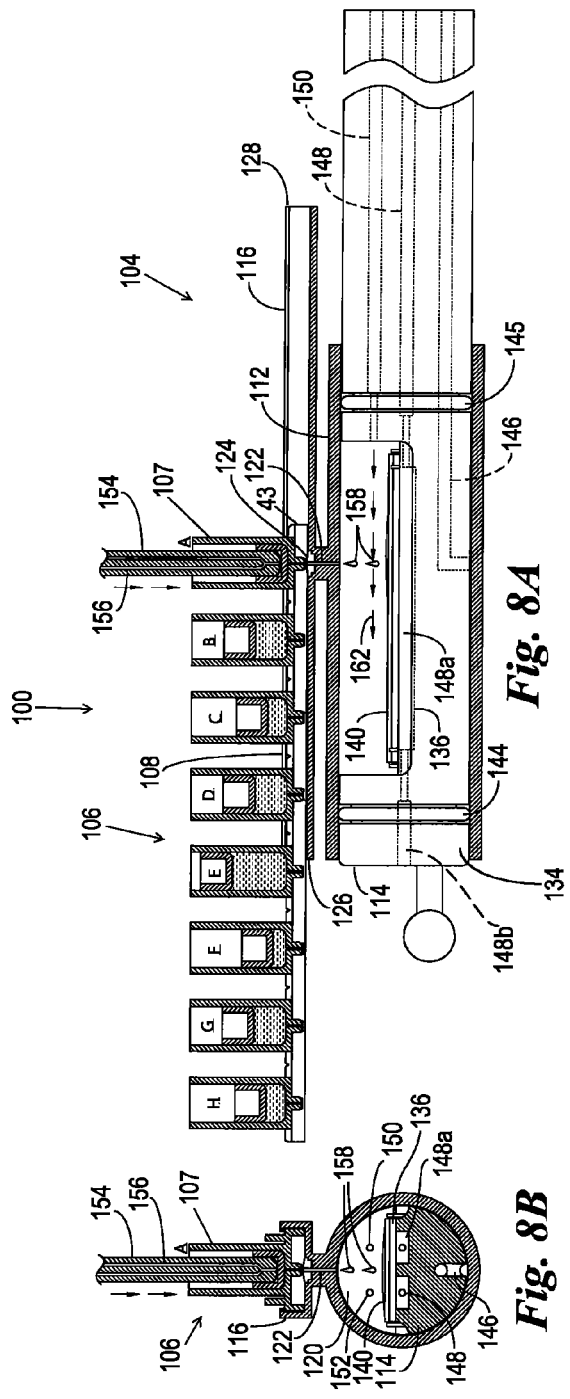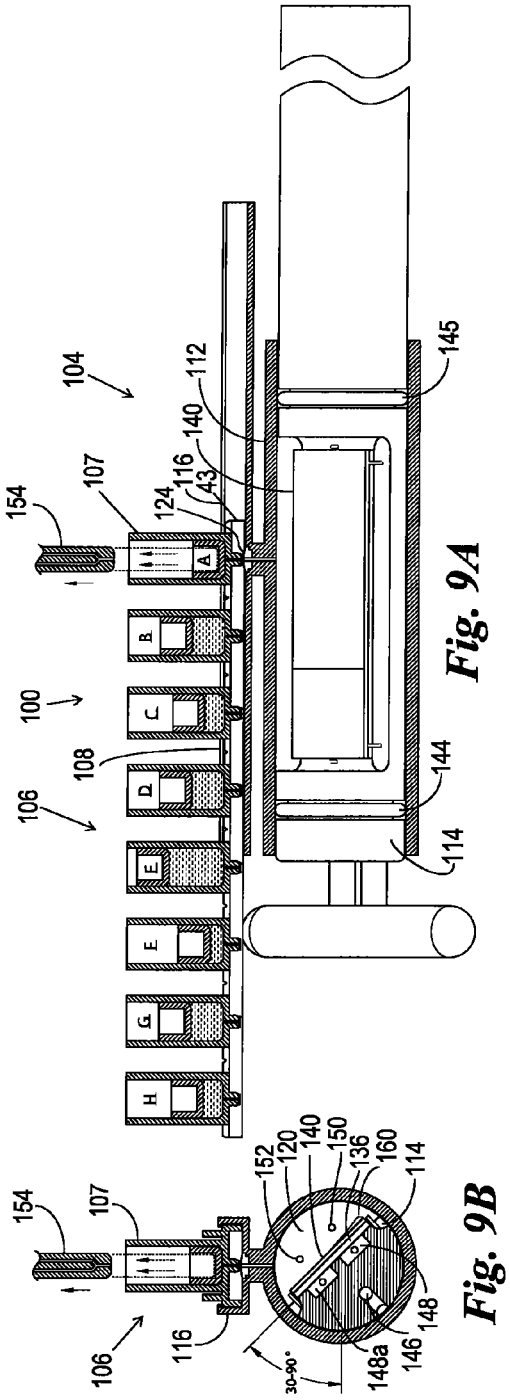

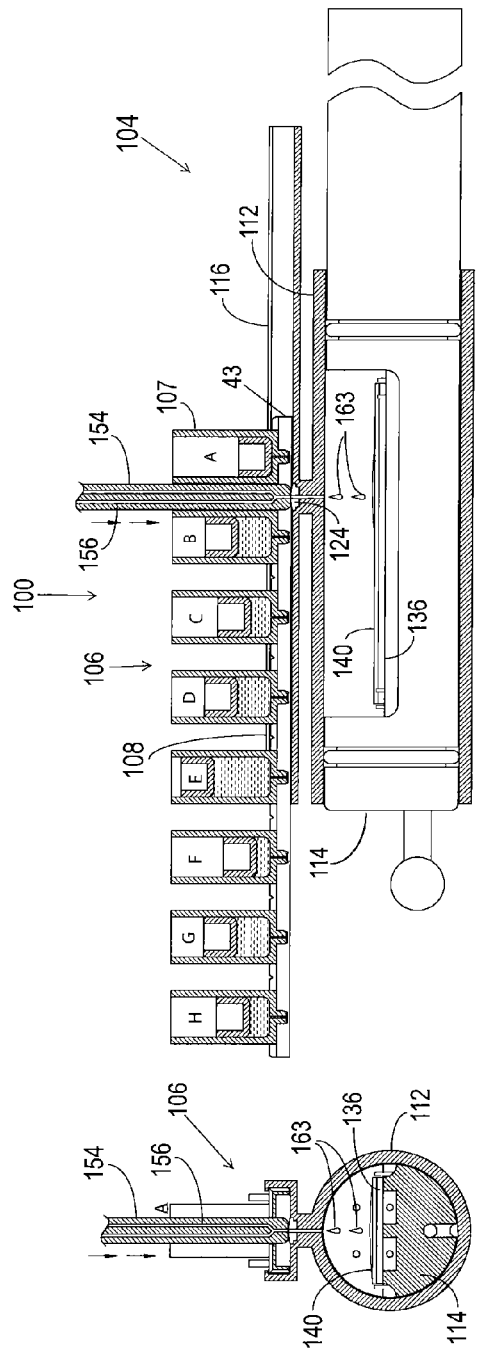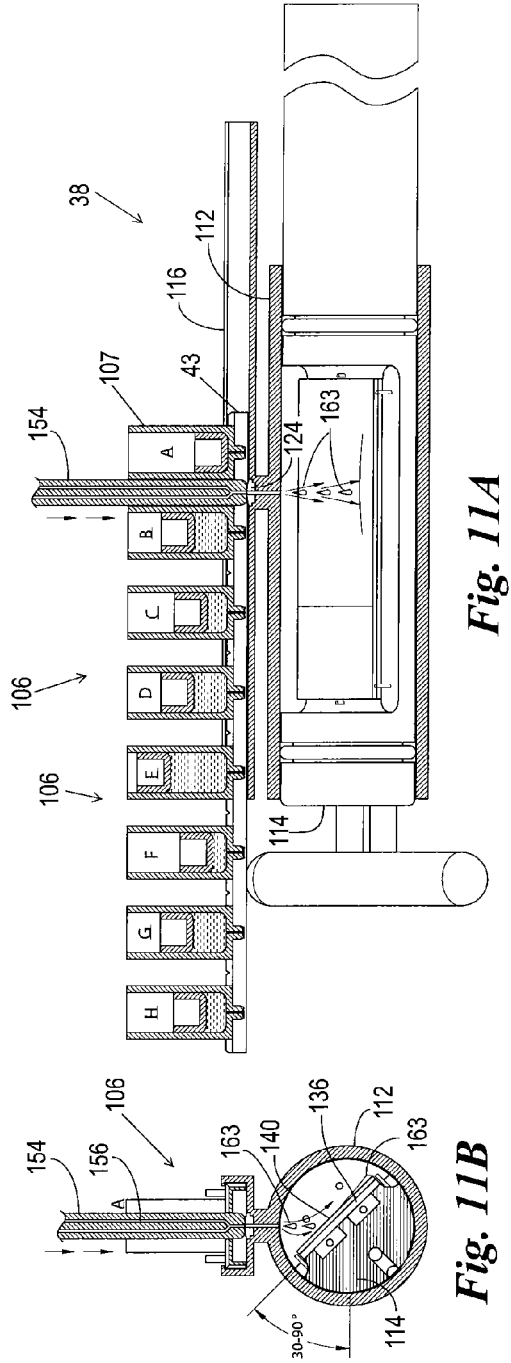

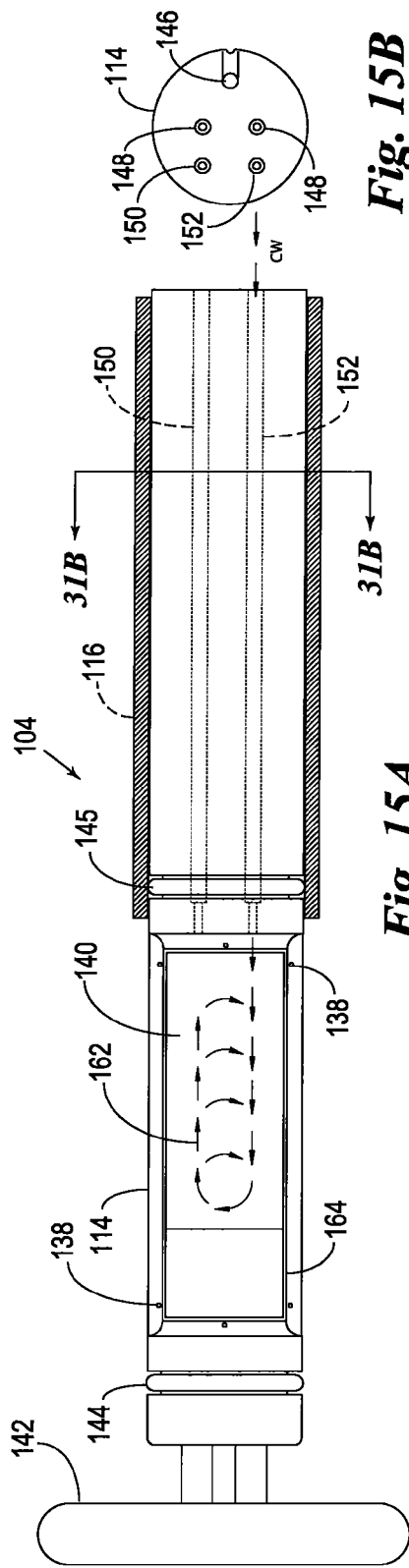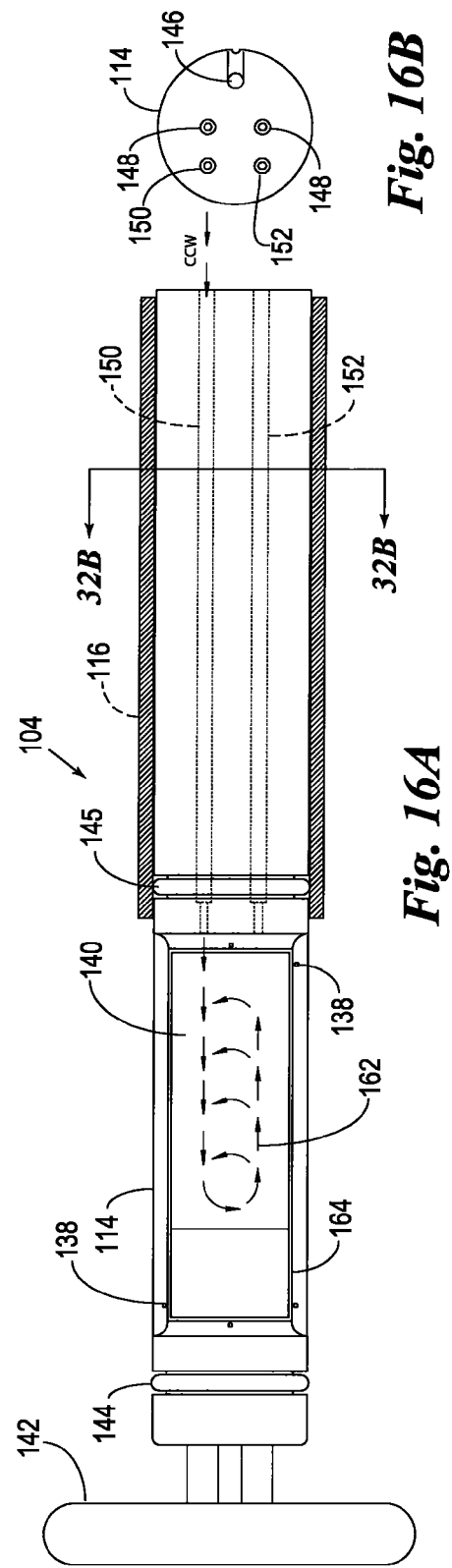

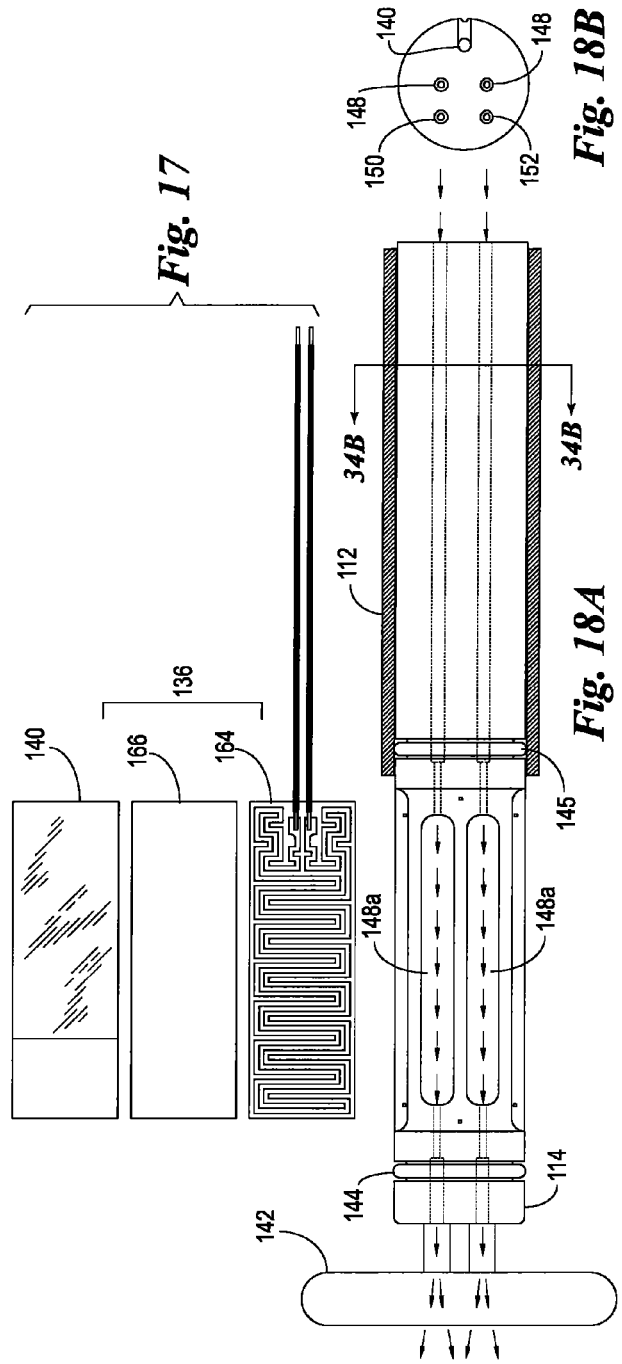

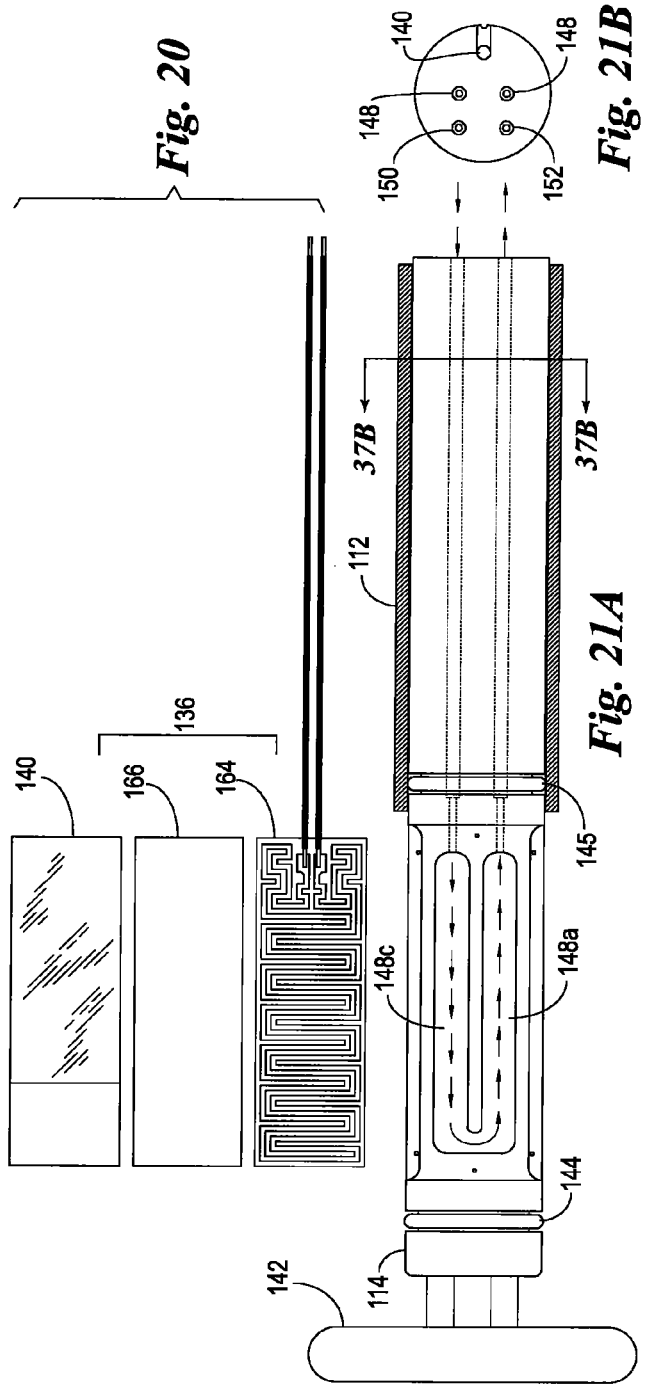

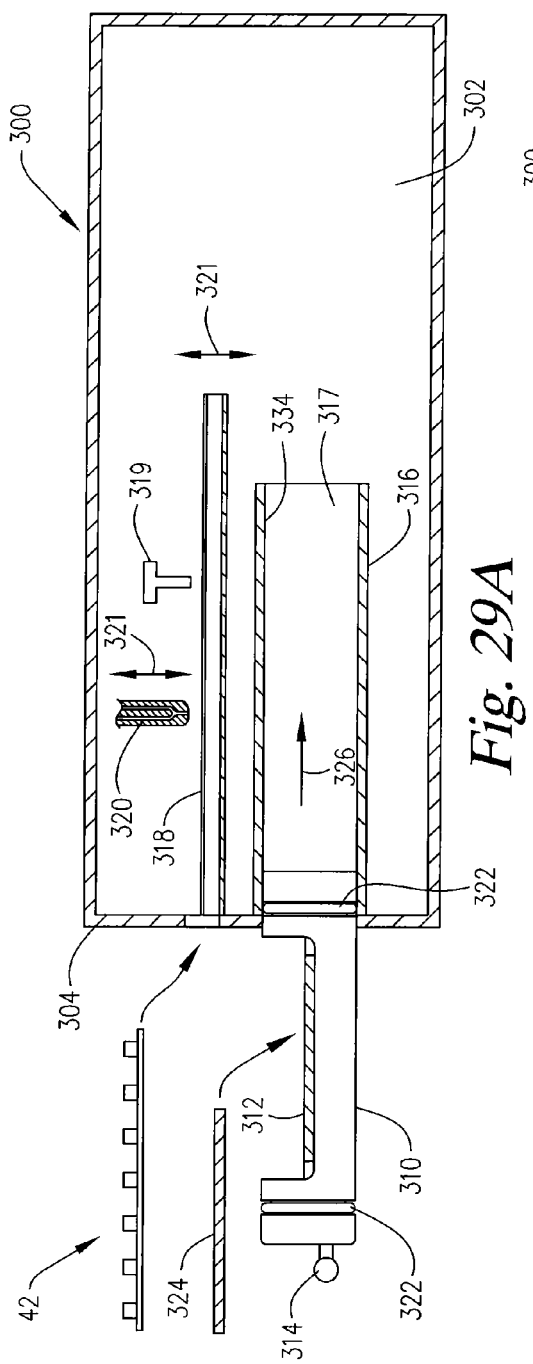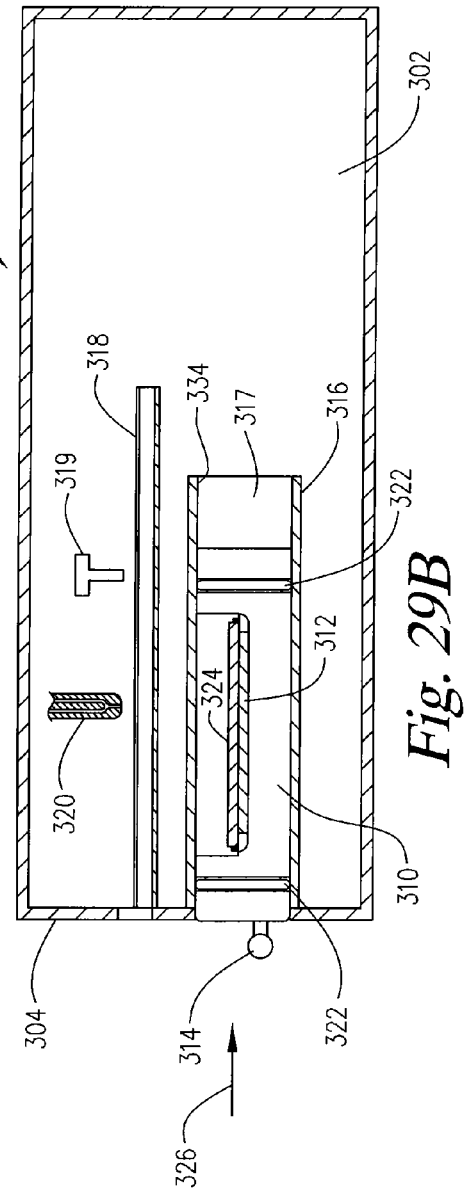

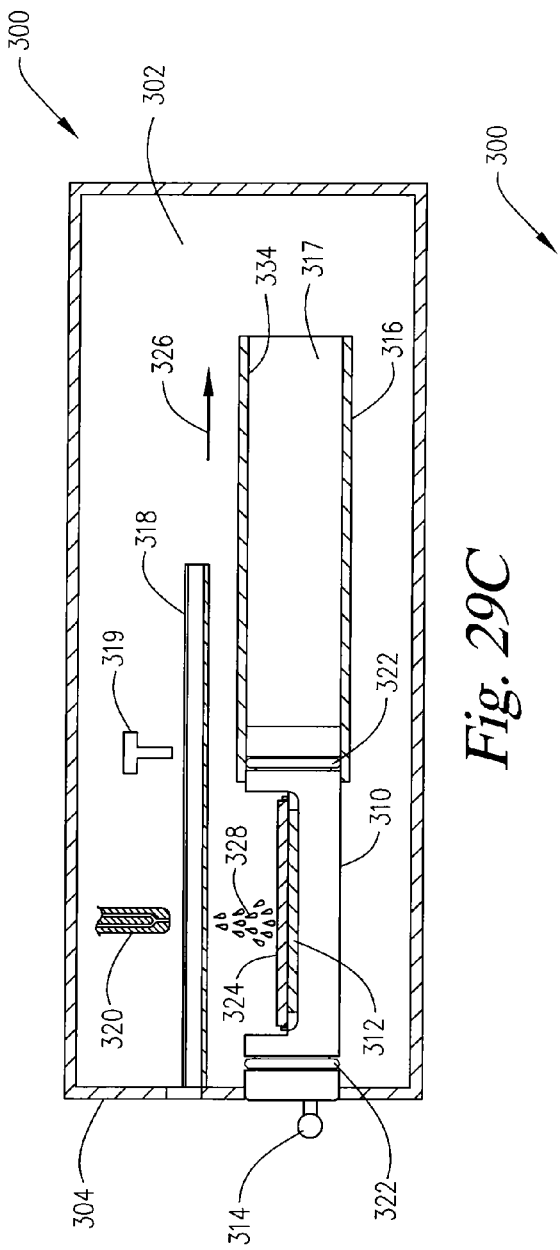
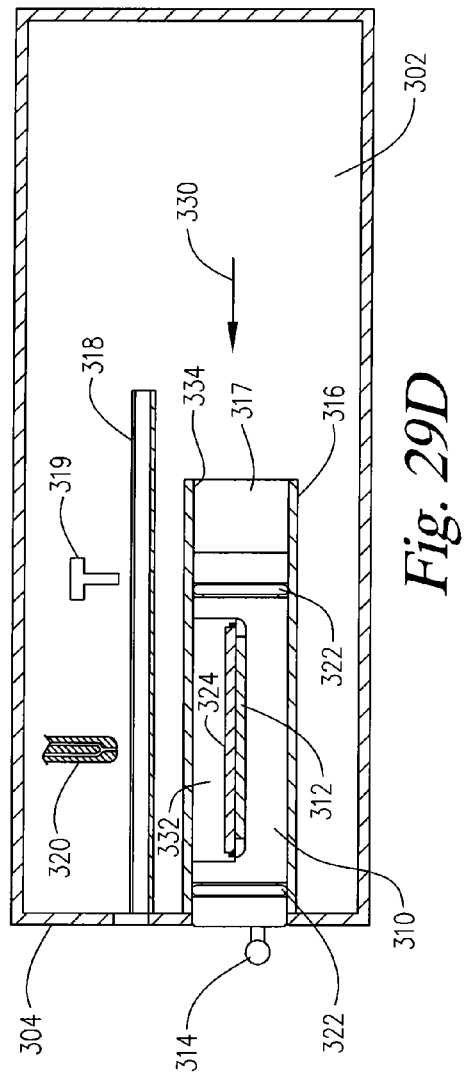
Fig. 29C
Fig. 29D

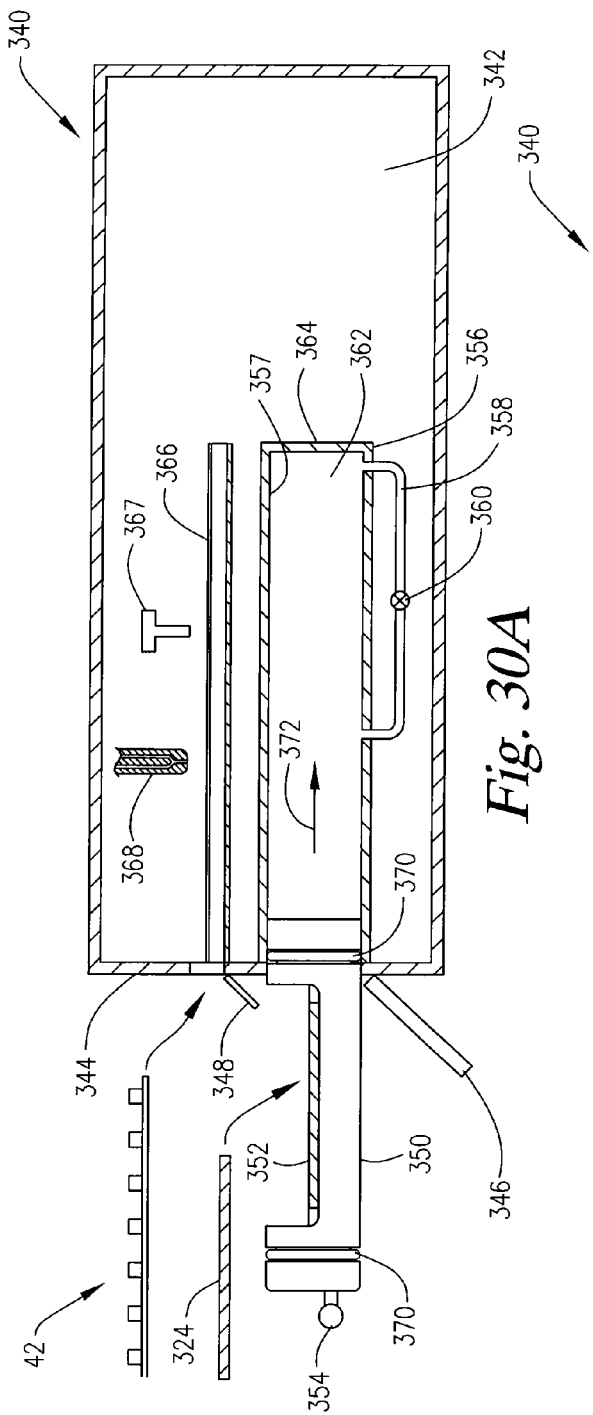
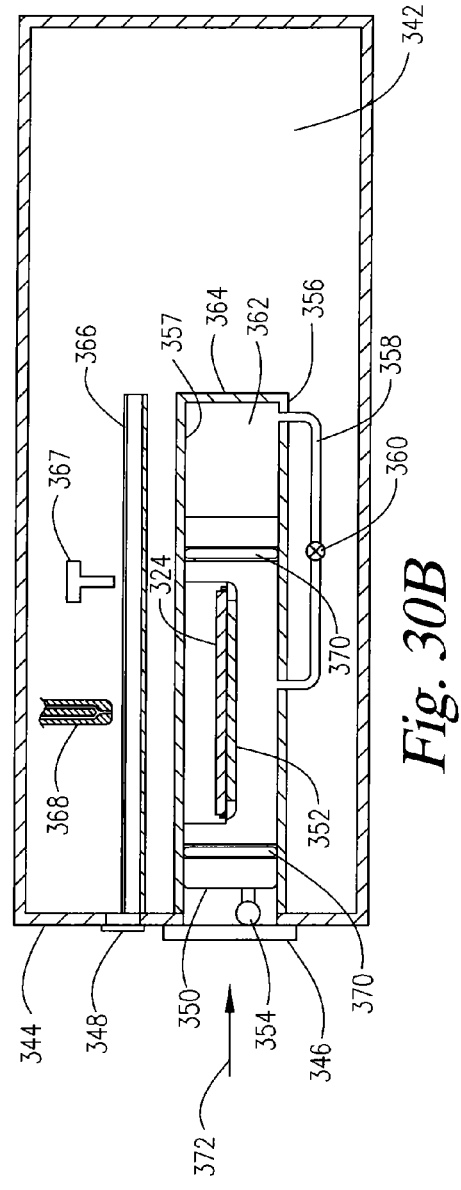
Fig. 30A
Fig. 30B

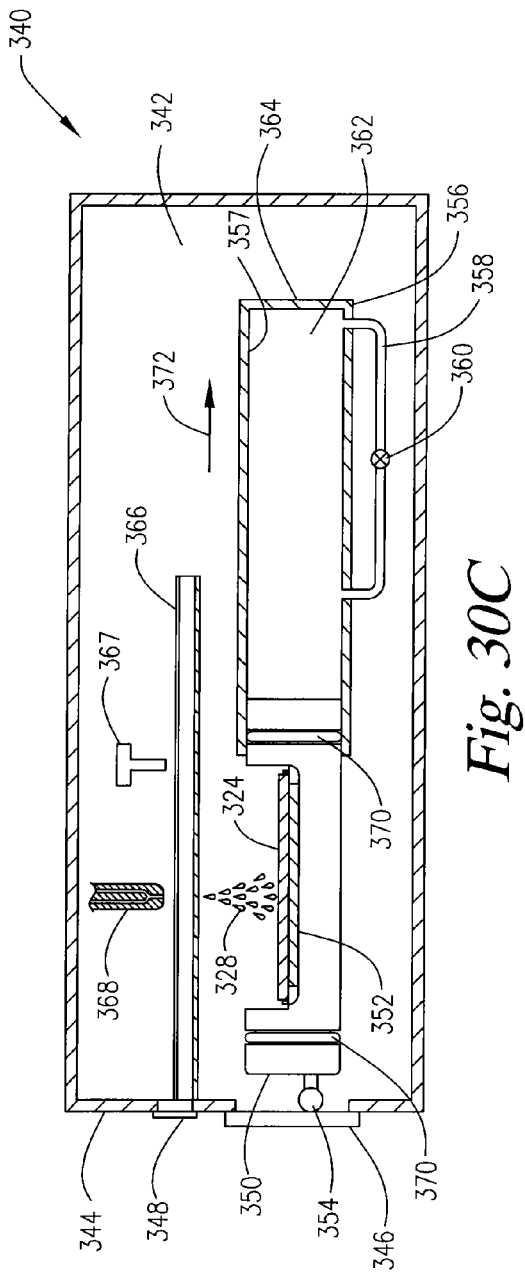
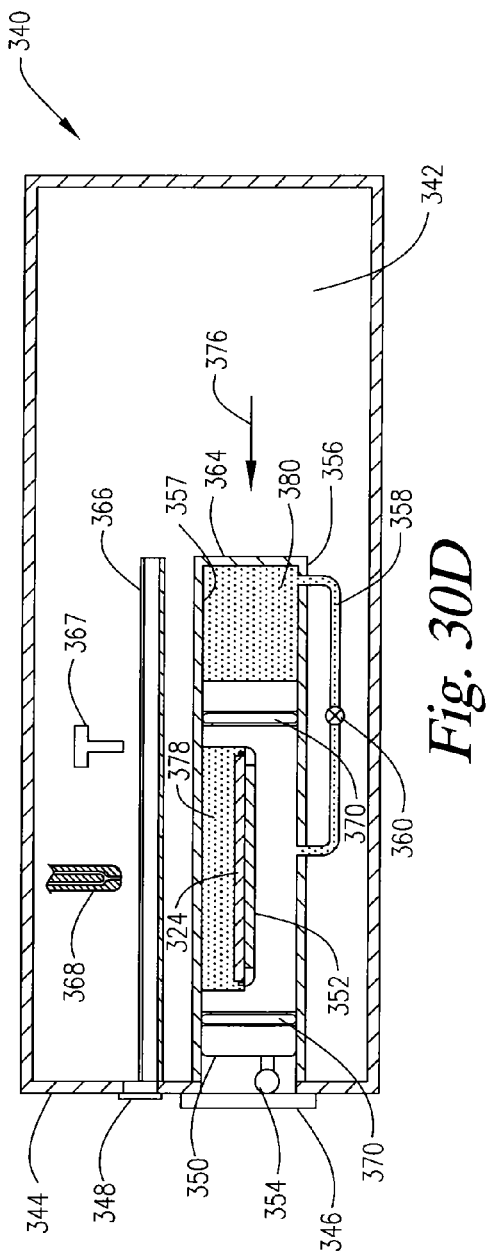
Fig. 30C
Fig. 30D

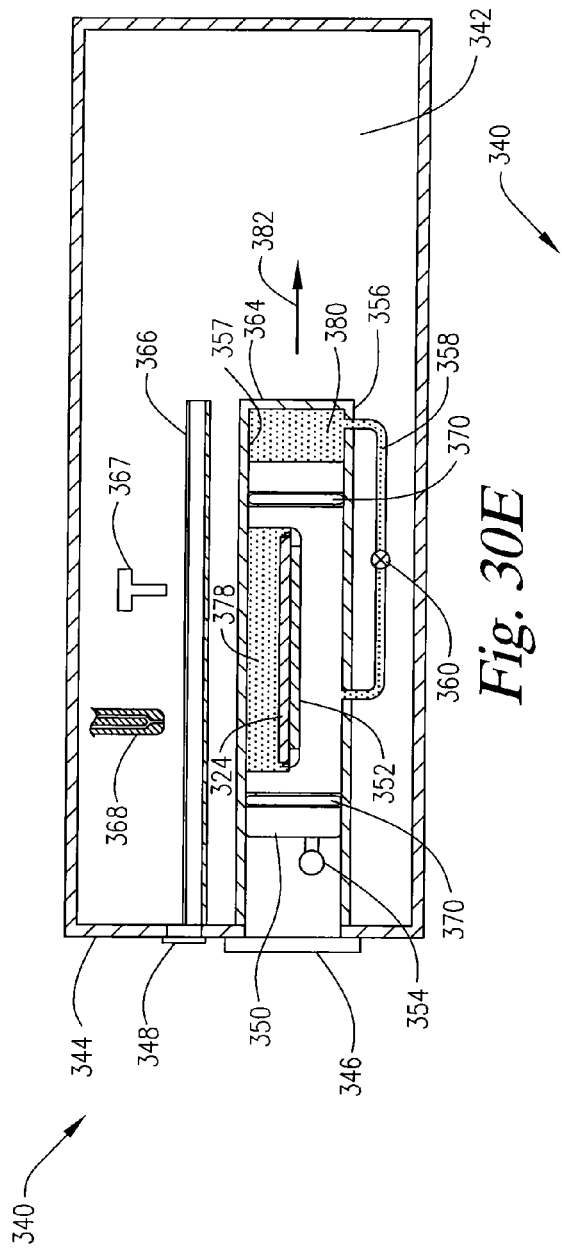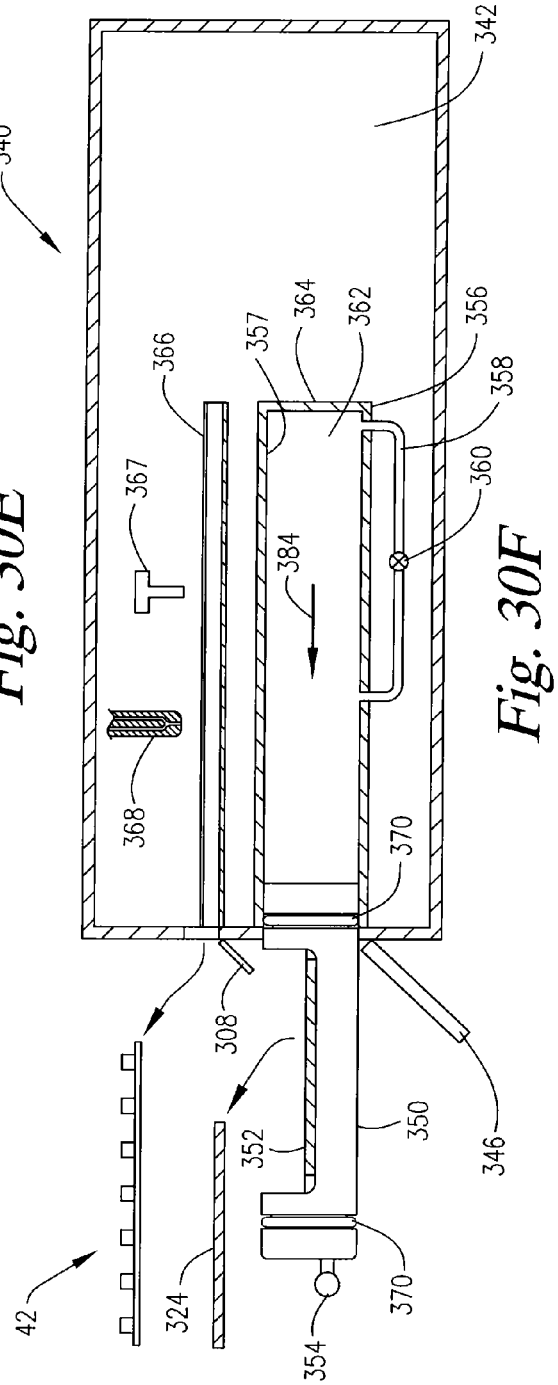
Fig. 30E
Fig. 30F

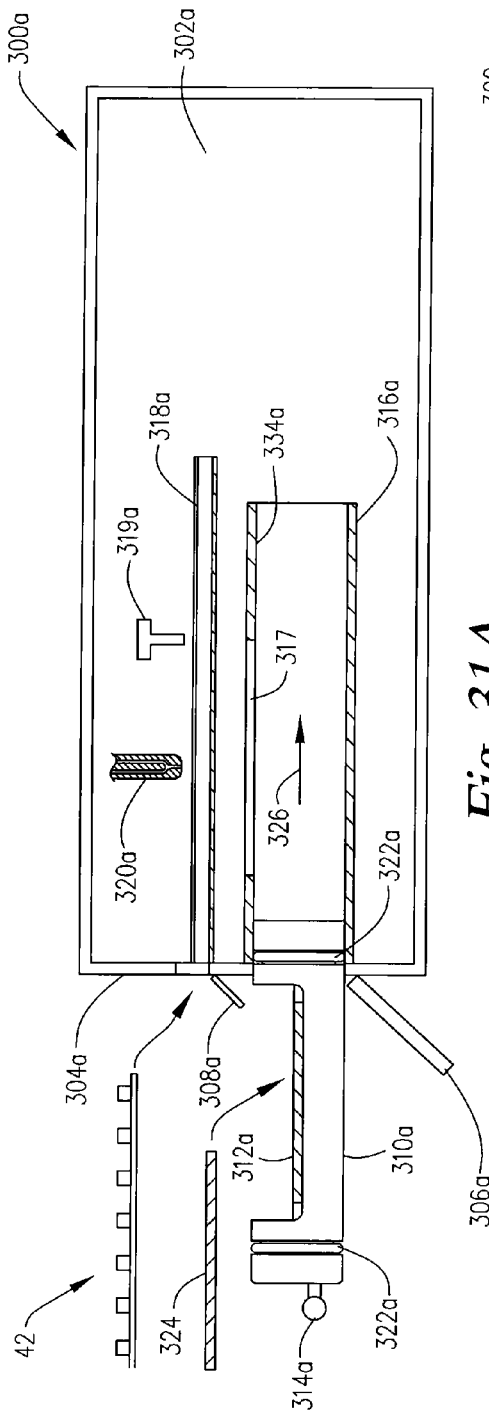
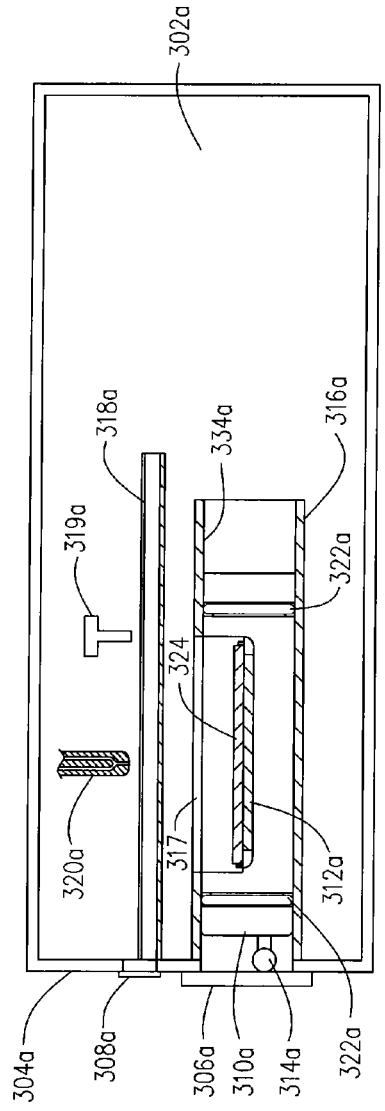
Fig. 31A
Fig. 31B

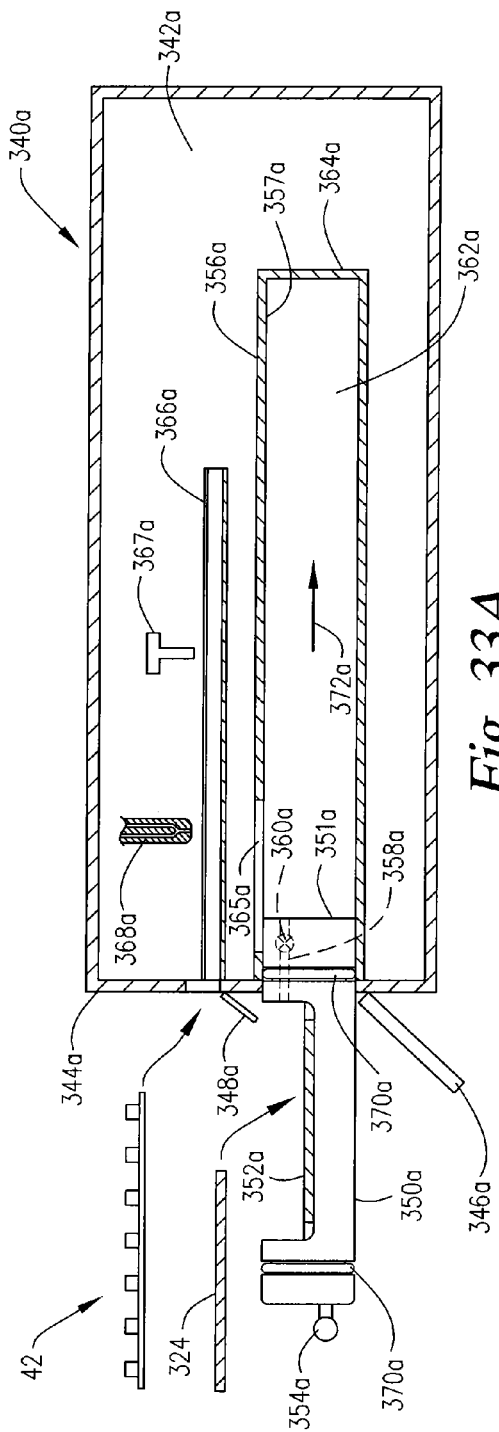
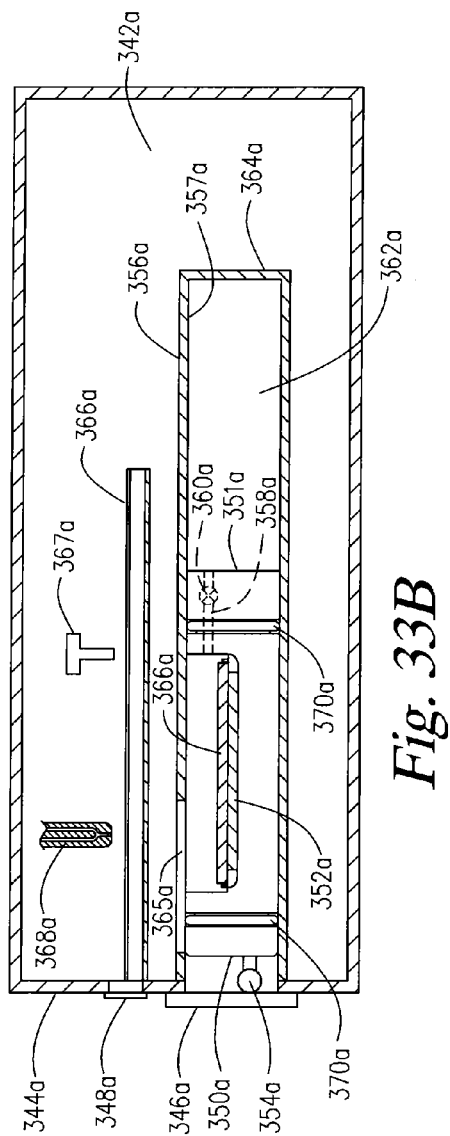
Fig. 33A
Fig. 33B

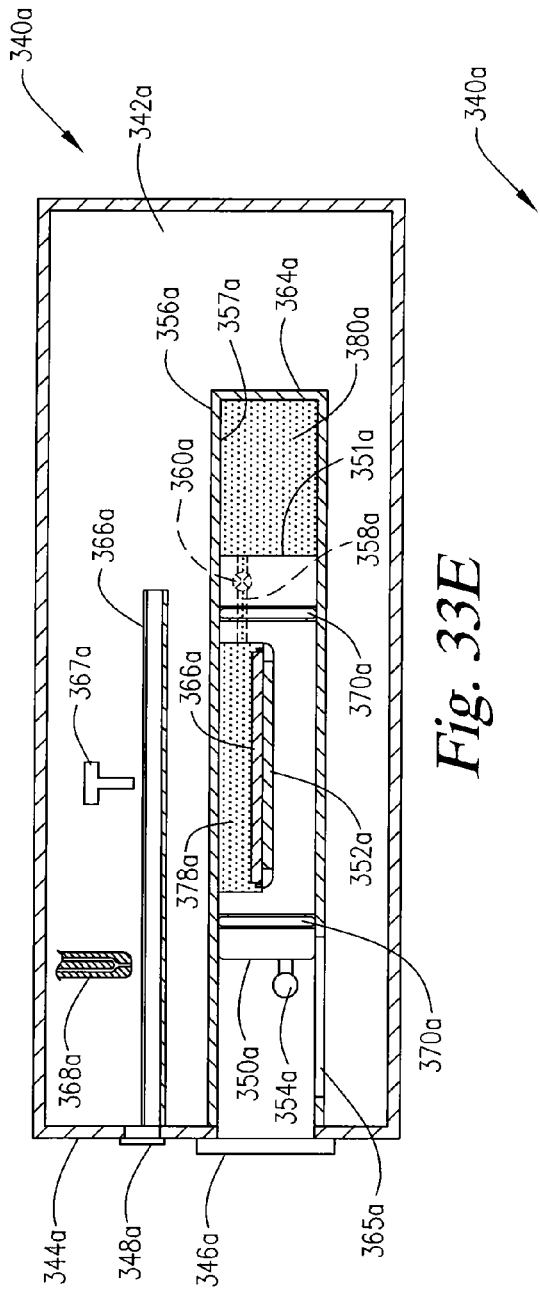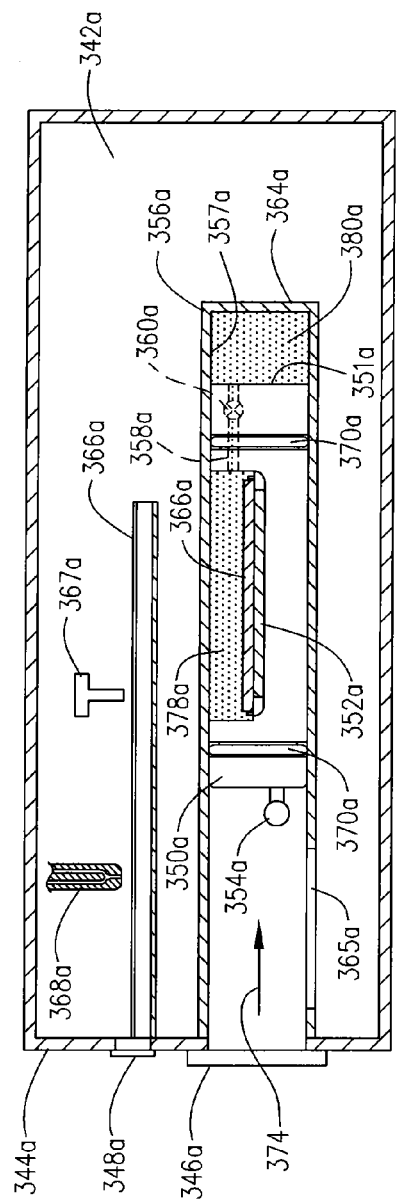

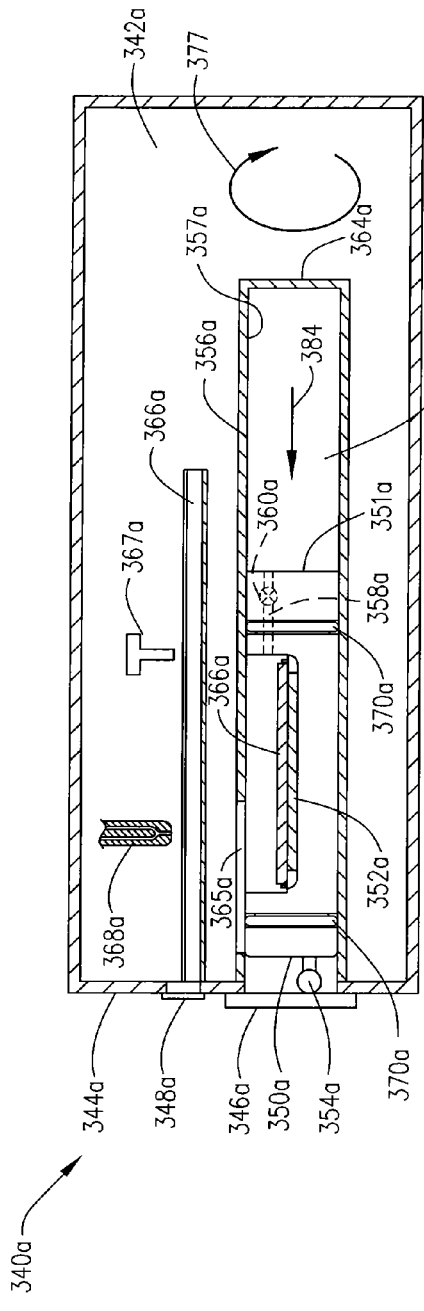
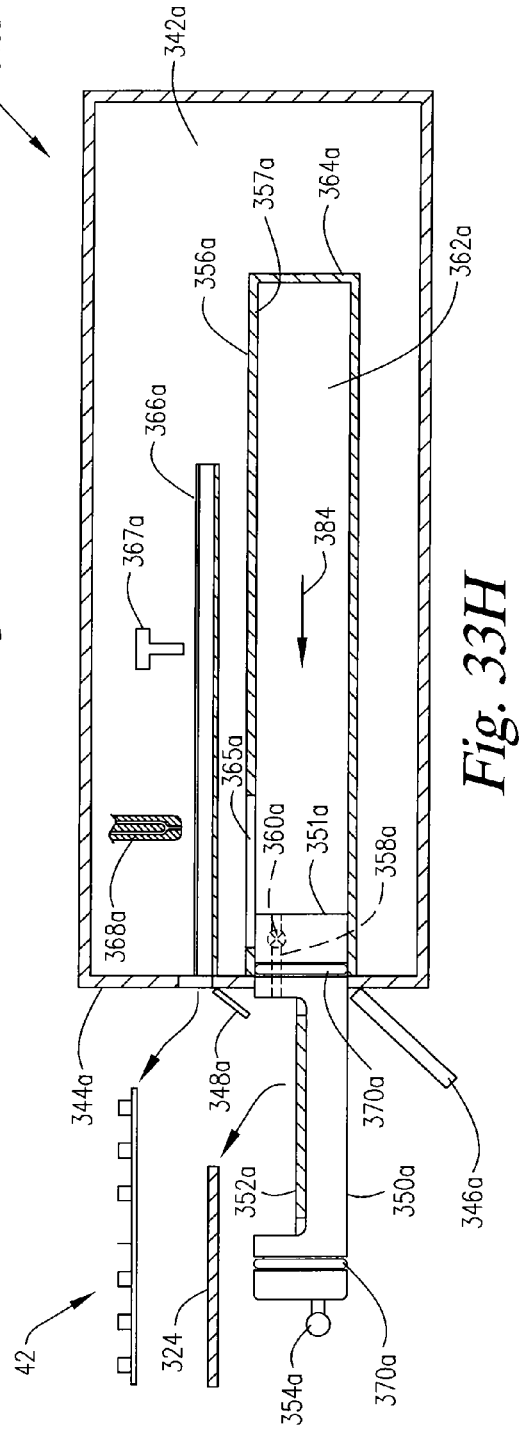
Fig. 33G
Fig. 33H

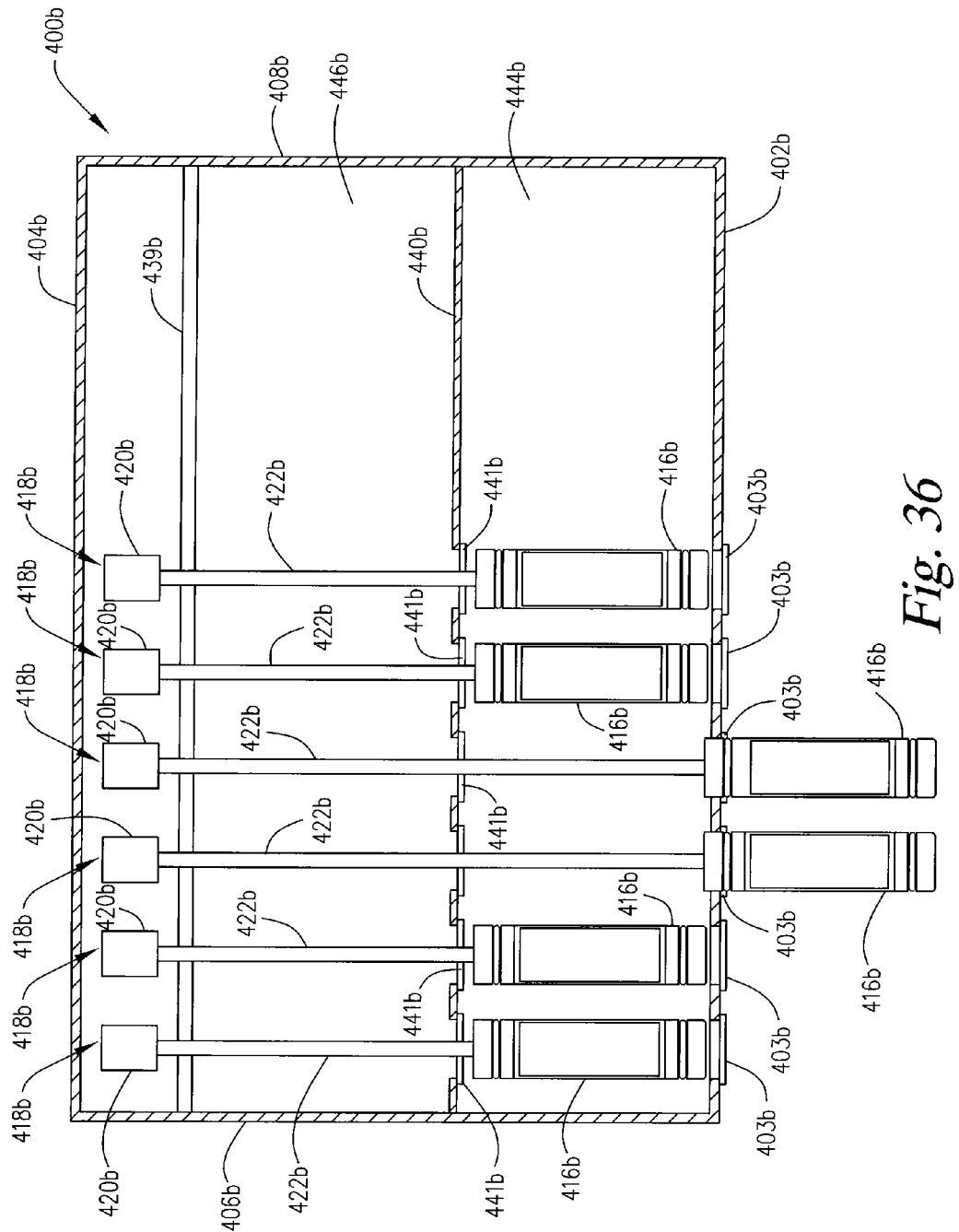

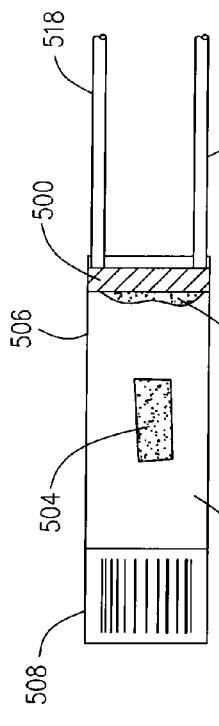
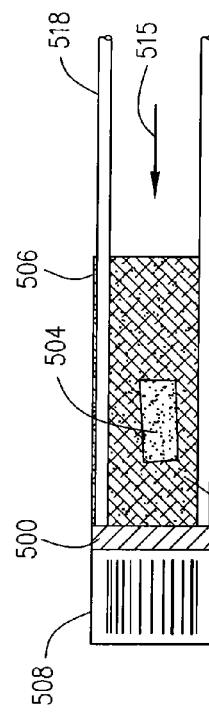
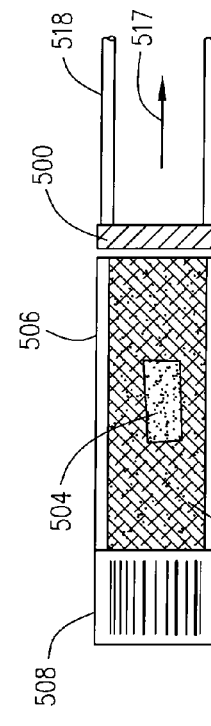
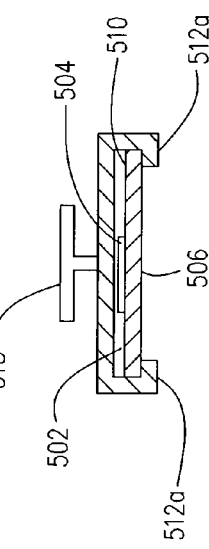
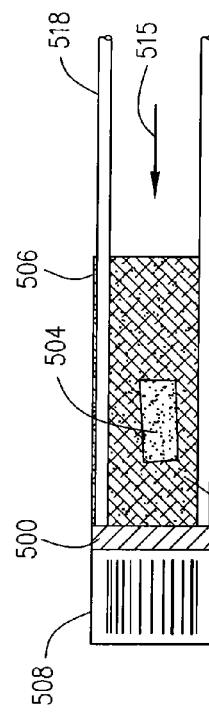
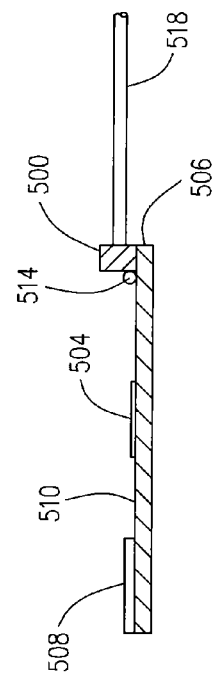

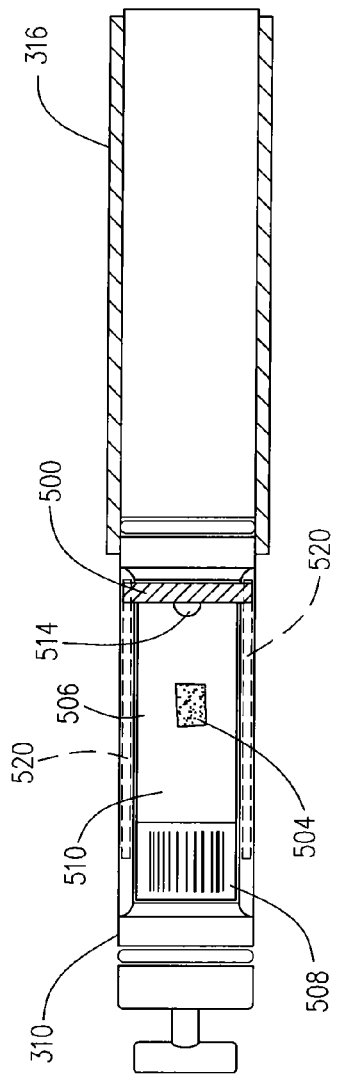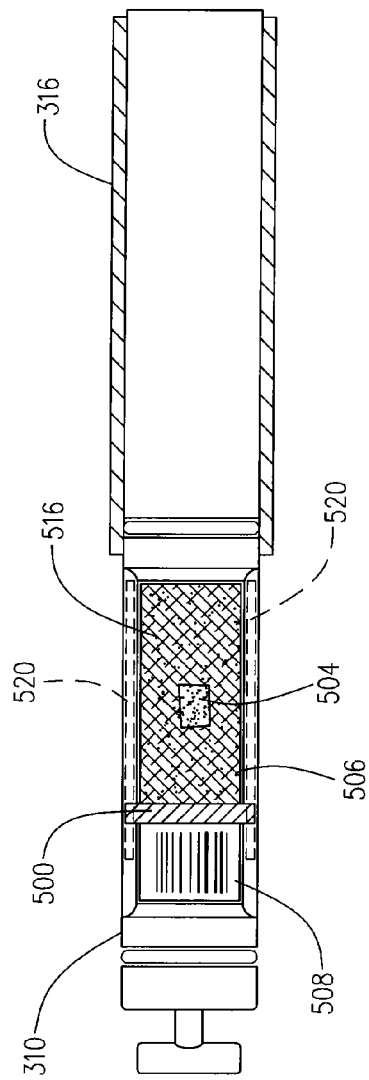
Fig. 38A
Fig. 38B

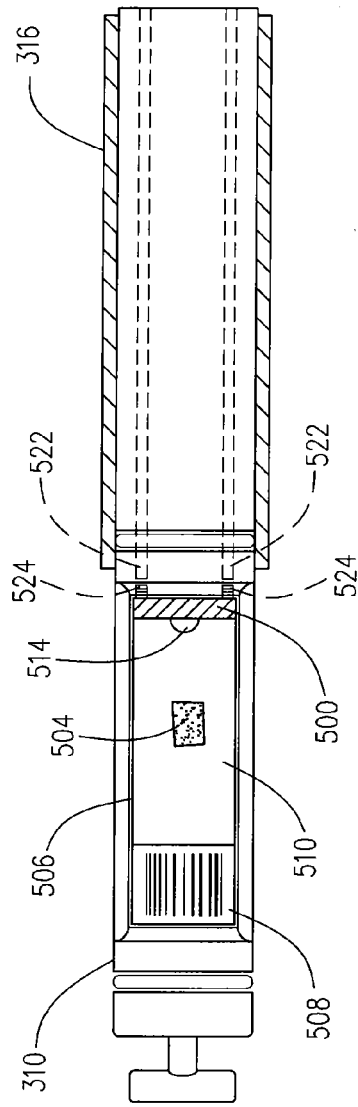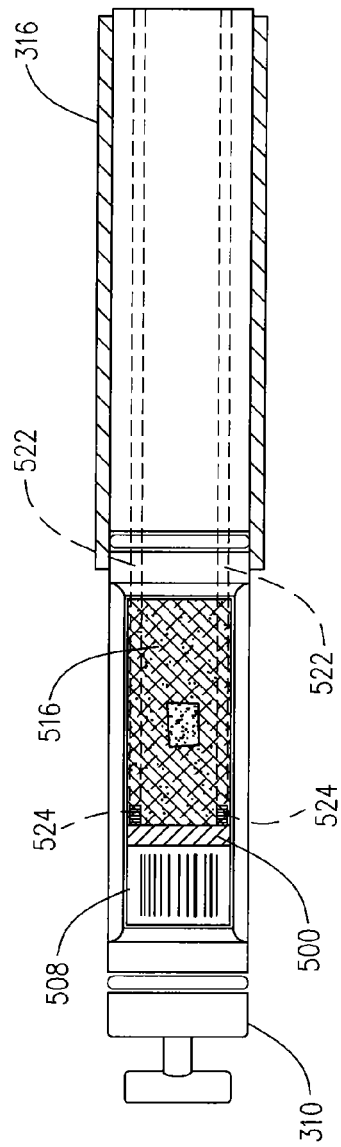

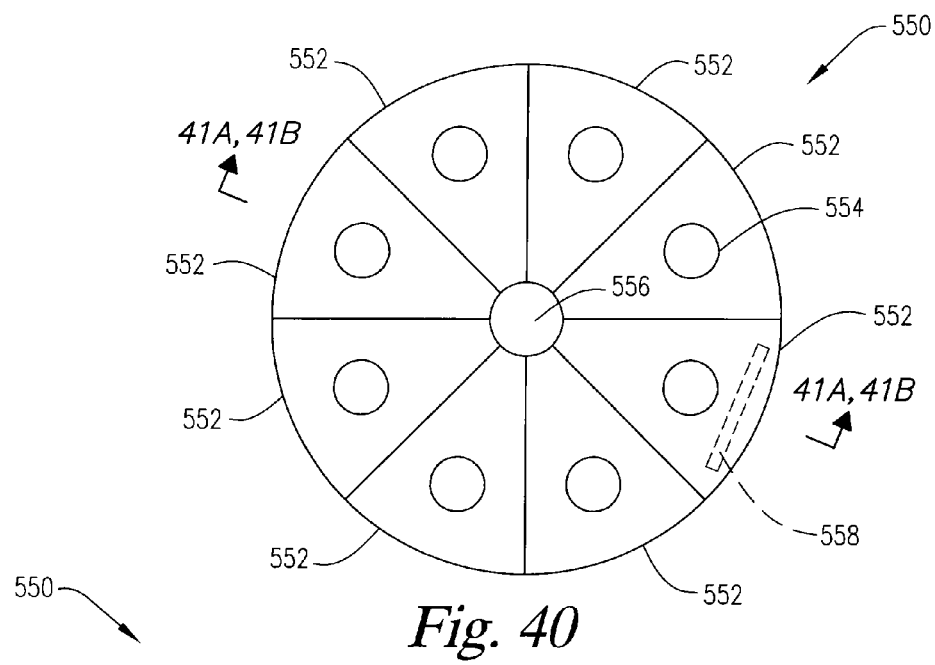
Fig. 40
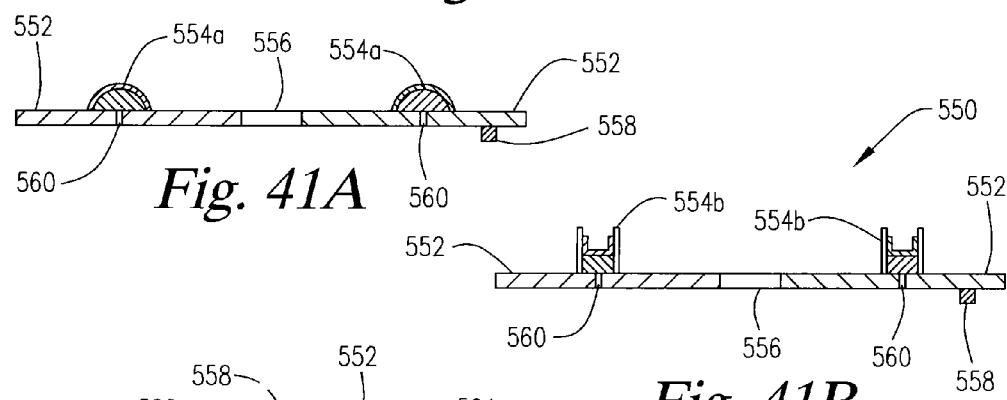
Fig. 41A
Fig. 41B
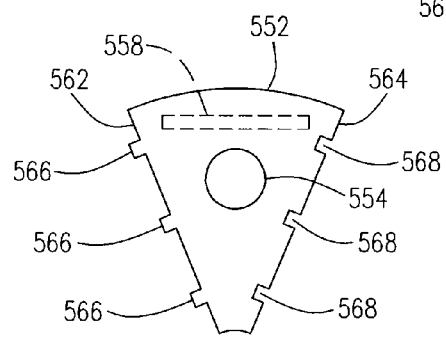
Fig. 42

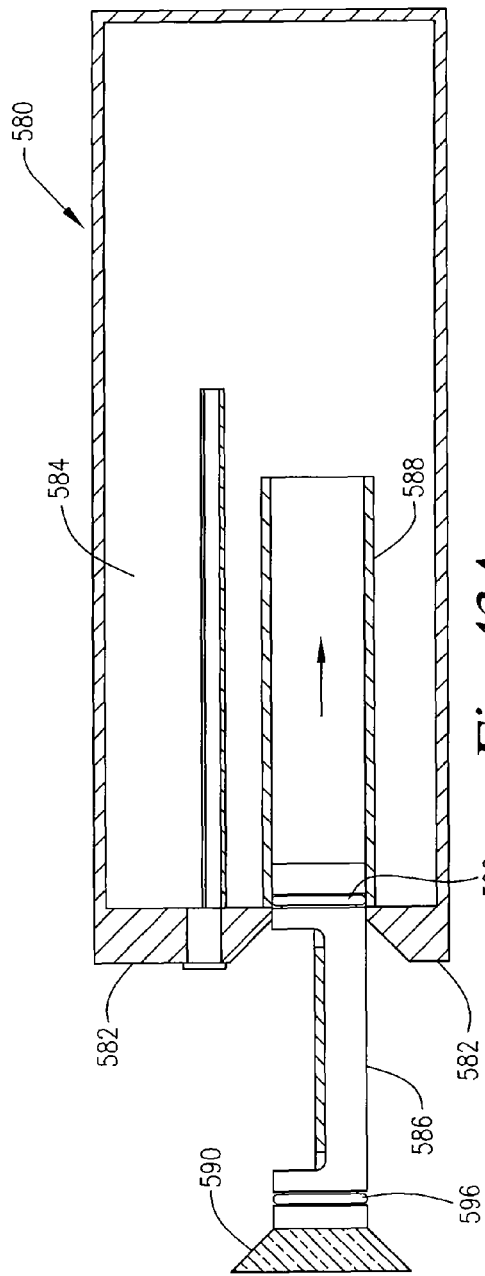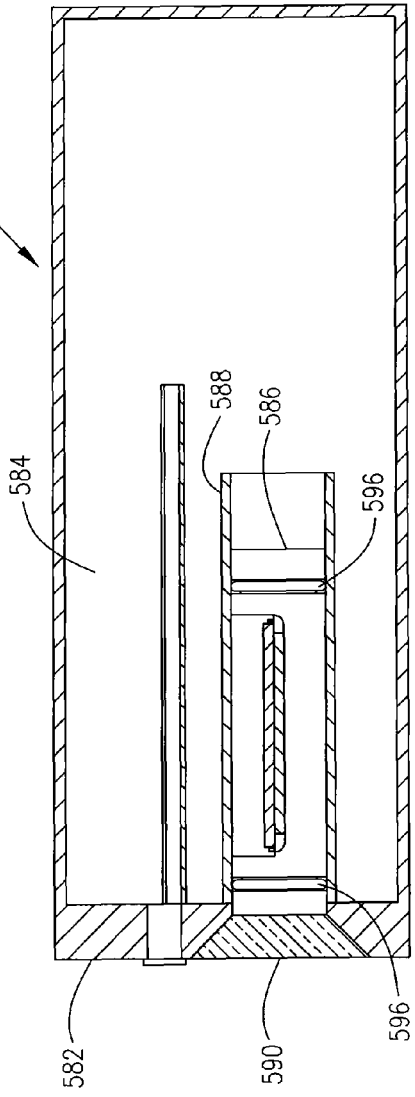

METHOD OF REMOVING FLOATATION LIQUID

CROSS-REFERENCE TO RELATED APPLICATIONS

This application claims benefit to U.S. Provisional Application Ser. No. 61/791,178, filed Mar. 15, 2013, which is hereby incorporated herein in its entirety.

BACKGROUND

During the process of placing a paraffin embedded (also known as wax embedded biological specimens) biological specimen on microscope slides, (i.e., paraffin or wax embedded tissues section(s) and paraffin or wax embedded cytology specimen(s)), a time consuming step of drying the water trapped between the paraffin embedded section and the microscope slide as a result of the floatation of the paraffin section onto the microscope slide is typically carried out. This water is from the histological water floatation bath. The water from the process of floating the paraffin section(s) onto a histological water floatation bath and then picking up the section(s) with a microscope slide is the preferred method for placing a paraffin section onto a microscope slide. Another method in the art is the user will add water or other liquid (with or without chemicals present like adhesives) to the microscope slide and then place a paraffin section onto the water on the microscope slide. These prior art methods of liquid flotation or liquid mounting of a paraffin embedded biological specimen to a microscope slide are known here as "histological water," "histological water flotation," "histological water flotation bath," "histological flotation water bath," "water," "liquid," "liquid flotation," "residual water," "flotation water," "flotation liquid," and "mounted microscope slides."

Since paraffin is hydrophobic and a water barrier, the trapped water between the paraffin section and the microscope slide must be removed so that the paraffin section can uniformly lay flat against the microscope slide and only then will the biological specimen become attached to the slide. This water trapped under the paraffin section and the residual water present on the microscope slide must be removed prior to placement of the slide, with paraffin section attached, in contact with aqueous and non-aqueous de-waxing solution to dissolve the paraffin therefore removing the paraffin in contact with the biological specimen prior to staining the biological specimen.

One method that has been used for removing the water trapped under a paraffin section and the paraffin surrounding the biological specimen on microscope slide, for a immunohistochemistry protocol, is letting the microscope slide and paraffin section dry at room temperature or under heat (i.e., air-dry, or 60° C. heated oven for 1 hour or 60° C. overnight) for 1 hour to overnight. This evaporation method (utilizing ambient room temperature air or a heat source) is excessively inefficient and excessively time consuming, and can produce tissue artifacts like crack artifacts in the tissue (due to uncontrolled evaporation of the water) and or bubble(s) artifact due to the heat inconsistently evaporating the water and a uncontrolled melting of the paraffin associated with the biological specimen. Ambient air evaporation of the water is very time consuming, in excess of 1 hour.

The evaporation method utilizing heat to evaporate the water and also melt the paraffin (excess of 55° C.) is also very time consuming, usually in the range of 30 minutes to 1 hour at 60° C. One would anticipate that if the water was exposed to increased heat, the evaporation time would decrease. This would be true, however, the increase in temperature (above 60° C.) produces unwanted heat artifacts and increases the problems associated with excessive heat evaporation. The method of evaporating the water present on and under the paraffin section and evaporating residual water on the microscope slide utilize only the inefficient method of evaporative drying or evaporative removal of the water. This method is based on excessive evaporation times (1 hour to overnight) for the water to evaporate, whether the evaporation is at ambient temperature (room temp) or evaporation is by heat which causes heat artifacts in the biological specimen.

Because the "drying" or "evaporation" of the water trapped under or associated with the paraffin section is uneven in all areas underneath the paraffin section or paraffin boarder surrounding the specimen (i.e., there are different areas and amounts of residual water under or around the tissue), during heating to evaporative the water, some melted paraffin areas can "float" on the evaporating water underneath itself, thus pulling pieces of delicate tissue away from the tissue specimen causing a detached tissue artifact. Another tissue artifact caused by heating the water on under the paraffin section can cause the water trapped under the paraffin section to go from a liquid phase to a gas phase and form a "gas bubble" under the tissue section which causes the delicate tissue to detach from the microscope slide and thus form a "bubble" or "rounded area" of missing tissue were the gas bubble was formed. These cracks, bubbles, and pulled away areas of the specimen are a significant staining artifact problem.

Since the drying of the water present around or under the paraffin section is not even and consistent do to the water being thicker or "pooled" in different areas around or under the paraffin section, there will be areas under the paraffin section and around the paraffin section that dry sooner than other areas around or under the paraffin section. The paraffin may start to melt while there is still water present under the paraffin. This melted paraffin will now be "floating" on the water underneath itself and can become mobile to "move" about the slide and away from its original mounted location. This movement of partial pieces of the once intact specimen can become important during the orientation of the original "whole" specimen that should have the same morphological size, shape, and physical characteristics of the embedded paraffin block that was cut by the microtome to make the paraffin section. These areas of "water-trapped floating specimen" on the microscope slide can be detrimental in the staining processes and in the interpretation of the specimen under a microscope since the original cut paraffin section no longer has the morphology of the paraffin embedded block or the originally cut biological specimen present in the paraffin block.

An accepted way to dry the water underneath a recently floated paraffin section onto a microscope slide is to dry the "wet" paraffin embedded section in a 60-100 degree Celsius oven with the microscope slide being placed most commonly in the vertical position in the oven for drying. This vertical positioning of the microscope slide cause the trapped water between the paraffin section and microscope slide to move from the top area of the paraffin section toward the bottom area of the paraffin section, which causes the "pooling effect" of the water under the paraffin section to increase at the lower end of the paraffin section due to the gravitational pull of the water towards the lower end of the paraffin section and thus increasing the likelihood of the delicate paraffin section's lower area to "detach," "break away," and/or "float" away from the upper paraffin section area.

This "water pooling" effect under the lower part of the paraffin section is significantly increased due to the physics of the trapped water under the paraffin section physically moving, due to gravity, toward the bottom of the paraffin section leading to the increased chance of the biological specimen "moving" or "breaking away" from the upper end of the paraffin section due to gravity pulling on the delicate paraffin section during this vertical drying. It is also known that drying a microscope slide in the horizontal position does not eliminate the "floating" or "pooling" effects of the water trapped under the paraffin embedded biological specimen, because the water is still trapped under the paraffin section. These unwanted heat induced problems and heat induced artifact(s), from heating, are only increased if the temperature is increased from the prior art evaporation temp of 60° C.

Another method known in the art of drying the floatation liquid from under or between a paraffin embedded section and a microscope slide is the use of "blotting" paper, or bibulous paper. The technician would, by hand or by manual method, "blot" the "wet" paraffin section directly with the bibulous paper. This "hands on" method has its draw backs related to the "tearing," "ripping," "dislodging," "dislocating," and otherwise damaging the delicate paraffin embedded biological specimen that is "floating" on the tissue floatation liquid between the paraffin embedded biological specimen and the microscope slide. This method is not repeatability reproducible due to the enormous manual labor intensive technical time to blot each and every microscope slide in a plurality of microscope sides. The different pressures and forces exceeded onto the delicate paraffin embedded biological specimen from each hand, finger, or otherwise manually pressing or touching of the bibulous paper is significant enough to damage the paraffin embedded biological specimen.

The paraffin embedded biological specimen would be damaged in part by the dry bibulous paper touching the wet paraffin embedded biological specimen, with the possibility of the wet paraffin embedded biological specimen "sticking" to the dry bibulous paper and possibly pulling up the paraffin embedded biological specimen and adhering at least part of the paraffin embedded biological specimen to the dry bibulous paper. This method is not effective or efficient, not to mention, the added cost of another consumable needed to be purchased to remove the floatation liquid from a wet paraffin embedded biological specimen. One would anticipate that to save the cost of the bibulous and the time to blot each microscope slide, it would be advantageous to keep with the prevailing method of heating the wet microscope slide and wet paraffin embedded biological specimen attached in a heating oven. It is common prior art practice after "blotting" to still place the "blotted" microscope slide and paraffin embedded biological specimen into a conventional heating oven to evaporate the residual floatation liquid that is still present between the paraffin embedded biological specimen and the microscope slide after "blotting."

To this end, a need exists for an apparatus and method for efficiently and effectively removing floatation liquid from between a microscope slide and a paraffin embedded biological specimen. It is to such an apparatus and method that the inventive concepts disclosed herein are directed.

BRIEF DESCRIPTION OF THE DRAWINGS

FIG. 8A is a cross-sectional side view of the reaction components of FIG. 7 in operation in a reagent dispensing phase.

FIG. 8B is a transverse cross-sectional view of the reaction components of FIG. 8A.

FIG. 9A is a cross-sectional side view of the reaction components of FIG. 7 and FIG. 8A in a reagent drainage phase.

FIG. 9B is a transverse cross-sectional view of the reaction components of FIG. 9A.

FIG. 10A is a cross-sectional side view of the reaction components of FIG. 9A in a rinse buffer dispensing phase.

FIG. 10B is a transverse cross-sectional view of the reaction components of FIG. 10A.

FIG. 11A is a cross-sectional side view of the reaction components of FIG. 10A in a rinse buffer drainage phase.

FIG. 11B is a transverse cross-sectional view of the reaction components of FIG. 11A.

FIG. 15A is a top plan view of the reaction compartment and slide support element of FIG. 13 which shows a clockwise air mixing step.

FIG. 15B is a transverse cross-sectional view of the air ports of the slide support element of FIG. 15A.

FIG. 16A is a top view of the reaction compartment and slide support element of FIG. 13 which shows a counterclockwise air mixing step.

FIG. 16B is a transverse cross-sectional view of the air ports of the slide support element of FIG. 16A.

FIG. 17 is a view of the microscope slide and detached components of the heating element of the slide support element of FIG. 12.

FIG. 18A is a top plan view of a slide support element with the microscope slide and heating element detached to show air flow through the air cooling ducts which are used to enhance a rapid cooling of the heating element.

FIG. 18B is a transverse cross-sectional view through the air cooling ducts of the slide support element of FIG. 18A.

FIG. 19A is a cross-sectional side view of the reaction components of FIG. 18A.

FIG. 19B is a transverse cross-sectional view through the air cooling ducts of the slide support element of FIG. 19A.

FIG. 20 is a view of the microscope slide and detached components of the heating element of the slide support element of FIG. 12.

FIG. 21A is a top plan view of a slide support element with the microscope slide and heating element detached to show air flow through the air cooling ducts which are used to rapidly cool the heating element.

FIG. 21B is a transverse cross-sectional view through the air cooling ducts of the slide support element of 21A.

FIG. 22A is a cross-sectional side view of the reaction components of FIG. 18A.

FIG. 22B is a transverse cross-sectional view through the air cooling ducts of the slide support element of FIG. 22A.

FIGS. 29A-29F are cross-sectional side views of an embodiment of the invention wherein the slide support element is able to move into and out of the staining apparatus and reaction compartment, and the reaction compartment is able to move backwardly to enable application of the reagents directly onto the microscope slide on the slide support element.

FIGS. 30A-30F are cross-sectional side views of an embodiment of the invention wherein the slide support element is able to move to variable positions within the reaction compartment such that the pressurization within the reaction compartment is able to occur via compression of the headspace ("in-situ" pressurization) of the reaction compartment by the slide support element.

FIGS. 31A-31F are cross-sectional side views of an embodiment of the invention which are similar to those of FIGS. 29A-29F, except the reaction compartment has an upper window through which reagents can be applied to the microscope slide without requiring movement of the reaction compartment backwardly. The reaction compartment can be rotated 180° (for example) to enclose the microscope slide within a pressurizable portion of the reaction compartment.

FIGS. 33A-33H are cross-sectional side views of an embodiment of the invention combining the "window" elements of FIGS. 30A-30F and the "in-situ" pressurization elements of FIGS. 31A-31F.

FIG. 36 is a top plan view of an apparatus similar to the staining apparatus of FIG. 4 except in place of separately pressurizable reaction compartments, the apparatus comprises a pressurizable common chamber into which the slide support elements can be withdrawn and treated under a common pressure level.

FIGS. 37A-37F shows a gap coating mechanism which causes a reagent to be spread over the biological specimen on the microscope during operation of the present invention. FIGS. 37A, 37B and 37C are cross-sectional views.

FIGS. 37D-37F are top views.

FIGS. 38A-38B shows top plan views of an alternate gap coater of the invention.

FIGS. 39A-39B are top plan views of alternate embodiments of the gap coater of the invention.

FIG. 40 is a top view of a reagent pack of the present invention.

FIG. 41A is a cross-sectional view taken through line 41A/41B of FIG. 40 which shows reagent containers as blisters or bubbles.

FIG. 41B is a cross-sectional view taken through line 41A/41B of FIG. 40 which shows the reagent containers as vials.

FIG. 42 is a top plan view of an attachable/detachable module of the reagent pack of FIG. 40 having a single reagent container thereon.

FIG. 43A-43B is a cross sectional side view of a slide support embodiment wherein the slide support element has a beveled seal for sealing with a front wall of the staining apparatus.

DETAILED DESCRIPTION OF EXEMPLARY EMBODIMENTS

Figure 1:
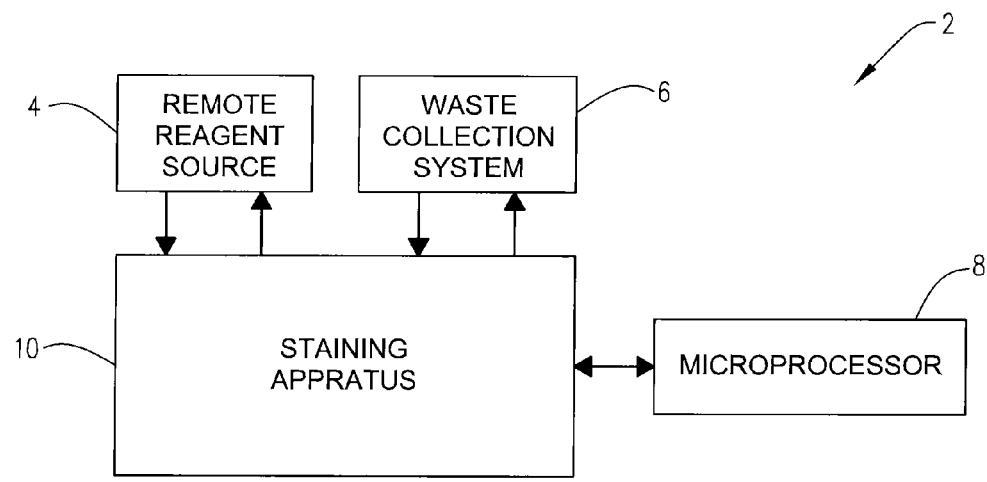
FIG. 1 is a schematic view of a microscope slide staining system of the invention.

In the following detailed description of embodiments of the inventive concepts, numerous specific details are set forth in order to provide a more thorough understanding of the inventive concepts. However, it will be apparent to one of ordinary skill in the art that the inventive concepts disclosed and claimed herein may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a process, method, article, or apparatus that comprises a list of elements or steps is not necessarily limited to only those elements or steps and may include other elements, steps, or features not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Throughout this disclosure and the claims, the terms "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, or combinations thereof, for example.

The use of the term "at least one" will be understood to include one as well as any quantity more than one, including but not limited to each of, 2, 3, 4, 5, 10, 15, 20, 30, 40, 50, 100, and all integers therebetween. The term "at least one" may extend up to 100 or 1000 or more, depending on the term to which it is attached; in addition, the quantities of 100/1000 are not to be considered limiting, as higher limits may also produce satisfactory results. Singular terms shall include pluralities and plural terms shall include the singular unless indicated otherwise.

The term "or combinations thereof" as used herein refers to all permutations and/or combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily referring to the same embodiment, although the inventive concepts disclosed herein are intended to encompass all combinations and permutations including one or more of the features of the embodiments described herein.

Contemplated herein is an automated microscope slide staining system that features an apparatus comprising a plurality of independently movable and operable slide support elements for individually and independently processing and pressurizing a plurality of individual microscope slides. Where used herein the term "microscope slide" is intended to refer to conventional microscope slides as well as other microscopy analytical devices which are used as vessels, substrates, or support structures for supporting biological and biochemical specimens for testing, processing and/or analysis, and which are sized and shaped to fit on a support element as described and contemplated herein. Thus the term "microscope slide" includes, but is not limited to, devices such as biochips, vials, flasks, microtiter plates, test tubes, petri dishes, and microarray plates, as well as standard glass or plastic microscope slides. In one embodiment, the apparatus of the present invention is used as an automated in-situ antigen recovery and staining apparatus and may feature independently movable slide support elements, each which has an individually heatable heating plate or element associated therewith. Each slide support element may support a single microscope slide. Each slide support element with the microscope slide thereon is enclosable within its own individually and independently pressurizable reaction compartment and/or comprises a portion thereof. In one treatment step, for example, a solution such as an antigen retrieval solution is disposed on the microscope slide and the heating plate or element heats the slide and the antigen retrieval solution thereon to temperatures of, for example, 120° C. to 160° C. by regulating the pressure within the individual reaction compartment (or pressurizable common chamber of the staining apparatus as explained below) thereby increasing the temperature that the solution can attain. In one embodiment each reaction compartment has its own individual pressure regulator, device, or switch to regulate pressure within the reaction compartment but more preferably pressure is regulated by modulating heat and pressure within the reaction compartment. Pressures exceeding 1 atm (i.e., exceeding 14.7 psi, 0 psig or 101.325 kPa) or below 1 atm can be created and maintained in the reaction compartment and the biological specimen on the microscope slide is exposed to this pressure level. The reaction compartment can hold, for example, 0.1 ml to 100 ml of antigen retrieval solution.

Where used herein the term "biological specimen" includes, but is not limited to, unprocessed specimens, processed specimens, paraffin embedded tissue, whole mounts, frozen sections, cell preps, cell suspensions, touch preps, thin preps, cytospins, and other biological materials or molecules including blood, urine, cerebrospinal fluids, pleural fluids, ascites fluids, biopsy materials, fine needle aspirates, pap smears, swabbed cells or tissues, microbiological preps including bacteria, viruses, parasites, protozoans, biochemicals including, but not limited to proteins, DNA, RNA, carbohydrates, lipids, ELISA reagents and analytes, synthetic macromolecules, phospholipids, support structures of biological molecules (e.g., metals, beads, plastics, polymers, glass), or any other materials attached to a biological testing substrate for processing, examination, or observation.

Each microscope slide, at some point, (before placing the microscope slide onto the present invention apparatus or after the microscope slide is placed onto the apparatus or further processing once the microscope slide is removed from the apparatus) during treatment is treated with a "liquid solution", "processing liquid", "reagent" or "reagents" (liquid reagent(s), dry reagent(s), semi-solid reagent(s), colloidal reagent(s), emulsion reagent(s), etc.) (generally referred to herein as "reagent", "reagents" or "reagent elements" "liquid solutions" "aqueous liquid solutions", "non-aqueous liquid solutions", "processing liquids", and including examples of, but not limited to, antigen retrieval reagents, molecular RNA and DNA probes, citrate buffer, EDTA, TRIS, PBS, with or without surfactants or detergents like SDS, Tween, Brij, ionic and non ionic detergents, polyols, and silicone additives, rinse buffers, immunoreagents, immunohistochemical reagents, polyols, biological stains, histochemical reagents, counterstains, in-situ hybridization reagents, chromogens, PCR reagents, monoclonal antibodies, polyclonal antibodies, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives) silicone additives and silane coupling agents as described in U.S. Pat. No. 7,731,811, activated or hydrolyzed biological adhesive (i.e.—products and reactants form silane coupling agents hydrolysis) as described in U.S. Pat. No. 7,731,811, hydrolyzed biological adhesive by-products like alcohol produced from the hydrolysis of the silane coupling agent coating method describe in U.S. Pat. No. 7,731,811, water from the histological flotation water bath, D.I., water from the histological flotation water bath, water with or without adhesives added to the histological flotation water bath. Other methods known in the art for applying paraffin sections onto microscope slides using liquids other than a histological flotation water-bath, and any other liquid or solution that is known in the art for processing biological specimens mounted onto microscope slides including any type of dry or desiccated reagent, semi-solid reagent or solution, colloidal solution or reagent, residual desiccated reagent, emulsions, or any other substance present on a microscope slide or biological specimen attached thereon that needs to be removed from the microscope slide and/or the biological specimen attached thereto, etc.

Because of the ability to pressurize and regulate pressure within the reaction compartment, and the ability to individually heat each slide, each slide can be heated to temperatures that could not be obtained without the elevated pressurized environment of the enclosed reaction compartment (or pressurizable common chamber). For example, since the vapor produced by the reagent is contained in the reaction compartment (or is released in a regulated manner), the pressure in the reaction compartment can be regulated to produce a reaction temperature required by the user. Pressures ("negative pressure", i.e., vacuums) below 1 atm (i.e., below 14.7 psi, 0 psig or 101.325 kPa) may also be created and maintained within the reaction compartment. For example, vacuum pressures of from 100 kPa to 10 kPa to 1 kPa to 100 Pa to 10 Pa to 1 Pa to 0.1 Pa may be formed and held in the reaction compartment.

In one embodiment, each reaction compartment and microscope slide can be heated separately and independently from the other reaction compartments and microscope slides by a conductive heating element (or heating plate) underneath or otherwise adjacent to the microscope slide (e.g., wherein the heating element is in a sidewall of the reaction compartment or in a cavity). In one embodiment in an enclosed reaction compartment, the microscope slide therein has an antigen retrieval solution deposited onto the microscope slide before or after being placed in the reaction compartment. The slide is then heated, in a preferred embodiment, to a temperature of about 100° C.-300° C. and under a pressure from 0.1 psig (102.015 kPa) to, for example, 350 psig (2515 kPa). In one embodiment the containment of the pressure is proportional to the temperature of the antigen retrieval solution, such that the regulation of both the temperature of the heating element of the reaction compartment and the regulation of the pressure generated by the solution on the slide can be adjusted during the automated staining procedure.

In one example, the heating element could heat the slide to 120° C. or greater and the pressure in the reaction compartment could be 16 psig (30.7 psi) wherein the solution on the microscope slide in contact with the biological specimen would be about 130° C., for example. It would be apparent to one of ordinary skill in the art of pressure regulated vessels that the temperature attained by the antigen retrieval solution would be dependant on the regulation and containment of either the pressure generated or the temperature of the heating element or both. If regulation of the temperature of the solution is to be at least partially determined by the pressure level in the reaction compartment, the heating plate can be set at 130° C. (for example) and the pressure relief valve could be set to a level to maintain a pressure of 19 psig (232.4 kPa) within the reaction compartment, for example. Thus, the temperature of the antigen retrieval solution would not substantially exceed 130° C. and would remain in the range of 120° C.-130° C.

If regulation of the temperature of the solution on the microscope slide is desired to be regulated by the temperature of the heating element, then the heating plate can be regulated to heat the slide to a desired temperature. Once the desired pressure within the reaction compartment has been reached, the temperature of the heating element is adjusted to keep the desired pressure within the desired limits. The reaction compartment under some conditions does not necessarily require a pressure regulator since the pressure in the reaction compartment may be determined solely by the temperature level of the heating element. In some embodiments it would be advantageous to have a regulator to relieve pressure if the pressure exceeds desired levels or to have a pressure regulator which would cause the heating element to be turned on and off depending on the desired pressure level.

Since "boiling" of the solution or reagent on the slide is suppressed by the containment of the pressure, the antigen recovery buffer or other reagent on the microscope slide may appear not to be boiling ("bubbling") even though it has actually reached a temperature at or above 100° C. Elimination or reduction of vapor loss due to boiling is advantageous because it removes the necessity of adding additional buffer during processing (such as is necessary when using certain other apparatuses known in the art, e.g., as shown in U.S. Pat. Nos. 5,654,200; 5,595,707; 6,296,809; 6,352,861; 6,582,962; 6,096,271; 6,180,061; 6183,693; 6,541,261; or 6,783,733). This removal of the necessity to add reagent during treatment occurs even when only small amounts of buffers or reagents are initially used (e.g., 500 μl-4 ml) and treatment times may be extended up to 60 minutes at high temperatures (e.g., over 100° C., e.g., 120° C.-160° C.). Loss of reagent volume during heating in the present invention is thus minimal due to containment of vapors generated. Another important advantage to minimization of boiling at high temperatures is that the biological specimen on the slide is not subjected to extreme agitation from bubble formation which could cause the biological specimen to detach from the glass slide or be otherwise damaged. Moreover, the controlled pressurized microenvironment in the reaction compartment of the present invention is very efficient because the amount of buffer that is used is minimal and the amount of time needed to heat to high heat conditions (e.g., 120° C.-160° C.) is also minimal (e.g., 5 minutes).

Commercial pressure cookers which are currently available for use in antigen retrieval procedures are bulky and require a greater amount of buffer or reagent and time to complete the high temperature antigen retrieval process and furthermore must be used to treat many slides in the same container. The typical pressure cooker treatment cycle from start time to the last step (rinse) typically lasts 45-60 minutes. Only a few different buffers can be heated at the same time, (on the order of 5-6 separate slide treatment containers) within a pressure cooker's main reaction compartment. Moreover, each separate slide container in a conventional commercial pressure cooker requires significant volumes of antigen retrieval solution (e.g., 45-50 mls per container). As opposed to the pressure cookers which are used in the field of antigen retrieval, the apparatus and method of the present invention may use the vapor pressure generated by the reagent on the slide itself to produce an elevated pressure in the individual reaction compartment. Conventional pressure cookers, to the contrary, rely on a separate liquid present within the bottom of the vessel to produce the vapor necessary to cause increased pressure within the vessel for inducing antigen retrieval on the slides therein. This method requires the additional step of heating the separate liquid to an elevated temperature before the process of heating the slide and the reagent thereon can begin.

Each of the individual reaction compartments of the apparatus of the present invention, to the contrary, utilize relatively small quantities of antigen retrieval buffer (e.g., 0.5-5 ml per slide) and heat up quickly and cool quickly due to the small amounts of liquid and area to be heated and cooled. Even a volume of 0.1-1 ml per slide can be used with the present invention and the typical time from start to finish using the present invention may be just 20 minutes, for example.

In a one embodiment of the invention, to prevent small amounts of liquid reagents (e.g., including, but not limited to antigen retrieval reagents, RNA and DNA probes, citrate buffer, EDTA, TRIS, PBS, with or without surfactants or detergents like SDS, Tween, Brij, ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives, or other reagent elements described herein) from being reduced in volume by the conversion from a liquid phase to a gaseous phase, and loss thereof, during heating (as occurs in other commercially available systems), the reaction compartment of the staining apparatus of the present invention, when closed, can be pre-pressurized, individually, prior to the heating of the slide and reagent. This pre-pressurization from a separate pressurization source, (i.e., rather than solely from the vapor pressure produced by the heated liquid in the reaction compartment), can significantly reduce the amount of loss of the gaseous phase (evaporation) of the small amounts of liquid reagents (e.g., 100 µl-5 ml) under high temperature conditions (e.g., 100° C.-160° C.) for extended heating times (e.g., 10-60 minutes) of the present invention, thereby eliminating the requirement of adding additional reagent after the treatment process has begun (i.e., after the reaction compartment or slide support element is isolated within the staining apparatus). For example, preferably, 0.1-4 milliliters of the reagent element (e.g., antigen retrieval reagent) is placed on the slide, the reaction compartment is then pre-pressurized and then the heating element begins to heat the reagent. The pre-pressurization of the reaction compartment, followed by heating of the reagent, produces an environment for the reagent to reach temperatures exceeding 100° C., for example up to 160° C., with minimal reagent loss due to gas phase formation (evaporation).

It is apparent that with the present invention particular temperatures and pressures can alternatively be established at any desired level for any treatment protocol known in the art of staining biological specimens. Super high temperature conditions can also be achieved using the present invention. These super high heating conditions can reach and exceed, for example, 350° C. and 300 psig (2170 kPa) due to pressurization, pre-pressurization, and the particular construction of the reaction compartment (described in further detail below). The individual pre-pressurizable reaction compartments of the present invention can be adapted to hold any type of vessel or substrate known in the art for containing a biological specimen for testing as described elsewhere herein.

In one embodiment, the reaction compartment can be pre-pressurized and remain pressurized even under very high pressures of over 300 psig (2170 kPa) to produce very high temperatures exceeding 300° C. for use in special procedures that require such very high temperature conditions. In alternate embodiments, the reaction compartment can generate and sustain temperatures and pressures, for high heat conditions, in the range of 100° C. to 160° C. to 200° C. to 250° C. to 300° C., for example. Preferably, a pressure of at least 15 psig (204.8 kPa) is maintained within the reaction compartment during heating.

As described elsewhere herein, this heat can be generated by a conductive heating element positioned on or in the slide support element beneath the microscope slide, a conductive heating element in the reaction compartment wall, other types of heating devices in locations adjacent to the reagents being heated, microwaves passed into the reaction compartment to heat the regents, and/or magnetic induction for example. These types of heating devices can all be incorporated separately or together with the systems described herein for the regulation of pressure.

The regulation of pressure within the reaction compartment (or pressurizable common chamber), either by pre-pressurization from an extended source, or by pressure produced by evaporation of the heated reagent, or other means such as in situ pressurization described herein, is an important component of the invention.

One version of the present invention eliminates the use of a single large container (e.g., a pressure cooker) to treat one or a plurality of slides under pressure. Each individually operable reaction compartment of a staining apparatus of the present apparatus can treat at least one individual microscope slide disposed therein with one or more individually applied reagents at an individualized temperature and pressure without relying on or affecting any of the other plurality of microscope slides in their respective reaction compartments in the same apparatus, i.e., each pressurizable reaction compartment can operate independently of each other pressurizable reaction compartment. An advantage of this embodiment of the invention is in its ability to treat every slide in the instrument separately and independently at an individualized temperature and pressure within a dedicated reaction compartment thereby increasing efficiency in the production and processing of specimens and providing a constant workflow advantage. Using this embodiment of the invention, a technician can separately begin a test of a slide utilizing any protocol at any temperature or pressure without affecting or stopping the other reaction compartments even when those other reaction compartments are already in use.

As described above, the temperature of the reagent on the microscope slide on the slide support element can be maintained by regulating the temperature of the heating element or by regulating the pressure to which the microscope slide is exposed or by both in combination. In one embodiment, for example, the heating element can be set to reach 125° C., the maintenance pressure can be set to 23 psig (259.9 kPa), and the reaction compartment can be pre-pressurized to 23 psig (259.9 kPa), and the slide can be heated such that the reagent on the microscope slide reaches a temperature of 125° C. for 10 minutes, and is then cooled for further processing. In a preferred embodiment, the pre-pressurized conditions may be attained before the microscope slide is heated so that, in this embodiment, the pressure in the reaction compartment is not produced by the vaporization of the liquid reagent contained in the reaction compartment, but rather by a separate pressurization method, system or device. The reaction compartment preferably holds a single microscope slide but can be adapted to hold two or more microscope slides. In the preferred embodiment, an individual reaction compartment is pre-pressurizable and is constructed to contain only a single microscope slide.

Without wishing to be held to theory, the pre-pressurization process, when using reagents (including any reagents described elsewhere herein) features conditions to minimize evaporative loss of reagents and or aqueous phase (water) or oil phase (oil) of reagents during heating and/or ambient temperature staining conditions. A further aspect of the embodiment featuring the independently pre-pressurized reaction compartments is that during the reaction process, pressure within the reaction compartment causes the reagents to come in close physical contact with the biological specimen by being "pressed" against the biological specimen wherein the physical contact between them is increased due to the pressure exerted on the reagent and thereby of the reagent upon the biological specimen.

This pressurized force of the reagent upon the biological specimen on the microscope slide helps to decrease the time of treatment by the reagents due to very efficient contact of the reagents with the biological specimen. Specimens may have their processing times significantly reduced due to superior staining caused by the reagents being physically "pressed" against the biological specimen, thus enhancing intimate contact with the biological specimen.

Polymerase Chain Reaction (PCR), including tissue PCR, is dependant on the retention of the water levels in the reagents during processing. Specific water concentrations, pH conditions, and temperatures must be strictly met in order for the PCR reaction to be successful. The pressurized conditions of the reaction compartment of the present invention are ideal for these conditions (low evaporation) to be met during staining. This low evaporation, due to an individually pressurized micro-environment (the individual reaction compartment) is ideal for PCR reactions on glass microscope slides, plastic microscope slides, vessels, tubes, micro arrays, micro titer plates, plates, or any other vessel used for the containment of biological specimens. This pressurization can also be used at ambient temperature as well (e.g., 25° C.).

In one embodiment of the apparatus, the pre-pressurizable reaction compartments are sized to hold only one microscope slide, while in an alternate embodiment, the reaction compartment can hold several microscope slides e.g., two, three, four, or more and can be pre-pressurized to decrease processing time and reduce evaporation or reagent loss.

The heating of the reagent on the microscope slide can be done by pre-pressurizing the reaction compartment with heated (below 100° C.) or super heated (above 100° C.) air (or gas) that would maintain the required temperature for the treatment protocol or would at least pre-heat the reaction compartment prior to the heating element reaching heating temperature or being turned on to heat, and maintain the heating of the reagent on the microscope slide. As noted above, in a particularly preferred embodiment of the invention, one or more of the reaction compartments of the staining apparatus is pre-pressurized after the microscope slide or slides are enclosed therein. The pre-pressurization of the reaction compartment may occur before, during, or after the heating element is actuated to heat the microscope slide and reagent thereon.

In another embodiment of the invention in which the apparatus comprises a pressurizable common chamber for pressurization without separate pressurizable reaction compartments (e.g., see FIGS. 35-36 below), a plurality of microscope slides together in the pressurizable common chamber may be pre-pressurized and heated thereby eliminating the need to add additional reagent to each microscope slide during the antigen retrieval process. For example, the plurality of microscope slides in the apparatuses shown in U.S. Pat. Nos. 5,654,200; 5,595,707; 6,296,809; 6,352,861; 6,582,962; 6,096,271; 6,180,061; 6183,693; 6,541,261; or 6,783,733 may be enclosed within a pressurizable common chamber and pre-pressurized before, during, or after the heating step begins. In this embodiment, a plurality of microscope slides on independently movable slide support elements are enclosed within a pressurizable common chamber, reagent is applied to the microscope slides (before or after enclosure within the pressurizable common chamber), the pressurizable common chamber is pressurized to a level above atmospheric pressure, and the microscope slides are heated so the temperature of the reagent on the microscope slide exceeds 85° C. and more preferably exceeds 100° C. Further, the reagent could be applied to the microscope slides after the pressurizable common chamber is pressurized.

The same steps as above could be followed in an alternate embodiment absent inclusion of a heating process. The result of the process without heating is reduced evaporation or vaporization of the reagent from the slide while reagent is reacting with the specimen or sample on the slide and an increase in the physical interaction thereof, due to increased pressure of the reagent with the specimen or sample on the slide.

In one embodiment, wherein the apparatus comprises separate pressurizable reaction compartments, each microscope slide on each separate slide support element is processed within its own individual reaction compartment that can be individually pressurized. Each reaction compartment is operable separately from each other reaction compartment. Together they comprise an automated slide staining apparatus able to process a plurality of microscope slides simultaneously, if desired, yet independently. Each reaction compartment (and slide support element) is functionally operably independent (i.e., non-interdependent) from each other reaction compartment. The independent operability of each reaction compartment (and slide support element) is due to each reaction compartment having separate operational mechanisms, including but not limited to, individually moving slide support elements, individually moving reagent dispensing packs and/or reagent dispensing devices, and individually movable or stationary ports and dispensers for rinses, pressure, vacuum and waste disposal. Preferably each single individual processing device corresponding and dedicated to any of the reaction compartments is independent at any time of the operation of the dedicated processing components of another reaction compartment whether it is in operation or not, including, preferably, microprocessing programs unique to each reaction compartment. All processing components (e.g., including, but not limited to, reagent dispensers, rinse ports, vacuum ports, pressure ports, waste ports, mixing ports, slide support elements, reaction compartments, air cooling ducts, and liquid cooling ducts) can be individually and independently moveable and/or usable. The exception to this, in an embodiment of the apparatus, is one or more "X-Y-Z" positioning devices discussed elsewhere herein (e.g., FIGS. 34 and 35).

The apparatus of the present invention preferably comprises a microprocessor which utilizes an operating system that can have multiple, individually, and/or simultaneously running processing programs, partially or completely specific to each individual reaction compartment and/or slide support element. This would enable a simple approach to programming by eliminating the need for the microprocessor to have one operating program to determine and evaluate the status of all processing steps as in current slide staining instruments (e.g., as shown in U.S. Pat. Nos. 5,439,649; 5,595,707; 5,758, 033; 5,839,091; 6,296,809; 6,352,861; and 6,783,733). In such staining instruments known in the prior art, microprocessors have a processing program which is "aware" of all the steps for each microscope slide in the staining process and which determines the correct time to activate a common processing device for a particular slide's use (i.e., reagent dispenser, rinses, air applications, etc.) This "thinking and reacting" approach to the microprocessor's involvement in processing a plurality of microscope slides is inefficient. A lagtime is produced when all the microscope slides are under the control of one program. This inefficient use of time causes increased time for processing just because of the requirement of the microprocessor to determine the next step for each microscope slide and determine any conflicts with two or more microscope slides needing to be processed by a common device at the same time. This type of microprocessing delays the completion of the processing of a microscope slide that would need a processing device at the same time as another microscope slide or multiple microscope slides.

Some staining instruments known in the art feature a "STAT RUN" option. With this type of processing, the user has already started a staining run and has decided that one or more additional microscope slides need to be placed on the instrument and processed because the processing of the "additional microscope slides" is more urgent. The user can put the "original" microscope slides on a lesser priority setting. The "new microscope slides" can then be placed on the instrument and would receive the priority use of the "new microscope slides" of all the processing devices (e.g., reagent dispensers). In between the priority staining protocol, the processing devices can then be used to treat the "original" or "non stat" microscope slides that were on the independently operable instrument initially. The requirement for this type of interrupted processing is eliminated due to the features of the present invention.

The advantages of the microprocessor of the present invention having a single or unique program for each reaction compartment (and/or slide support element and/or reagent dispenser) eliminates the need for a microprocessor which is able to plan the interdependent steps for a plurality of slides being processed, as required by prior art systems. A further advantage of having a separate microprocessing program unique to each reaction compartment (and/or slide support element, etc.), is that if the programs of one or several reaction compartments fail, there will be no effect on the operation of the other reaction compartments (or slide support elements). One advantage to the individualized microprocessing system contemplated above is that there is no appreciable downtime in the event of a failure in one or a few reaction compartments (or slide support elements). To the contrary, in the instruments of the prior art, if the microprocessor or operating system fails, then the instrument is completely inoperable and must be repaired.

In the present invention, in one embodiment, there can be a common "master" operating system that could be in communication with each individually unique program so that the user can open a separate program specific to any or all of the reaction compartments (and/or slide support elements) at anytime. The separate individual program running a specific reaction compartment (and/or slide support elements) would have all the protocols loaded therein for completely processing a microscope slide. The separate program could be updated and edited by the user and with the help of the master program could update all the other separate programs so that each reaction compartment (and/or slide support elements) could have the same protocols updates or edits. In the event of a master program failure, the separate unique programs to each reaction compartment (and/or slide support elements) would still be operational to process microscope slides; it just would lose the ability of communicate with the separate programs of the other reaction compartments (and/or slide support elements) for updating, downloading, or uploading information. In a variation of this, each reaction compartment (and/or slide support elements) may be individually separated and unique to itself with regard to its operating program with no link to the other reaction compartments (and/or slide support elements). A further advantage to having a master operating system is the ability to communicate with the other separate reaction compartment (and/or slide support elements) programs for diagnostic purposes, uploading, downloading, and general and specific communications between reaction compartments (and/or slide support elements).

In one embodiment of the present invention, all the motion control requirement necessary for operation of the system can be in the form of AC, DC, solar, and optionally other power sources like pneumatic and steam. The microprocessor can be run on AC, DC, and solar for example. The entire instrument is compact and can be configured with any amount or numbers of reaction compartments necessary. The instrument can be portable to be used in the field (research for example) or carried to an area of use. The number of reaction compartments (and/or slide support elements) typically would be 10-20 per chamber and are stackable or are joined linearly or are connected in any other manner which is appropriate (e.g., see FIG. 3B). A portable field unit could have as few as 1-5, or 5-10, reaction compartments (and/or slide support elements per chamber), for example, for less weight. Preferably the components are made from light weight, anti-corrosive materials. A further advantage of the present invention is that the instrument can be serviced in a modular approach. Each reaction compartment and/or slide support element and/or reagent pack support device in the module can be removed individually and serviced or discarded and replaced with an all new component. All the motion controls are preferably modular and either serviceable or completely replaceable. An advantage to this modular serviceability is that the other reaction compartments and/or slide support elements that are in use or could be used, are not affected during servicing of any device or part from a different reaction compartment and/or slide support element.

An advantage of the present invention, as explained previously, is that each microscope slide can be treated with a separate unique reagent, inferring that any microscope slide can have any reagent and be treated at pressures and for varying amounts of treatment times which are the same or different from any other microscope slide loaded into the apparatus. Examples of reagents which may be used in the present invention include, but are not limited to: antigen retrieval reagents, RNA and DNA probes, citrate buffer, EDTA, TRIS, PBS, with or without surfactants or detergents like SDS, Tween, Brij, ionic and non ionic detergents, and silicone additives, rinse buffers, immunohistochemical reagents, histochemical reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, and deparaffinizing compositions of water with one or more silicone surfactants or silicone additives. Another advantage with the present invention is that cross contamination from reagents or biological specimens on adjacent or nearby microscope slides is eliminated because each microscope slide is separated and treated with its own reagent in a separate reaction compartment or on a separate slide support element.

Another important advantage of present invention is that each individual reaction compartment and/or slide support element can be cleaned or repaired separately and automatically at the same time that other reaction compartments and/or slide support elements are being used to process microscope slides. Thus, there is no downtime or interruption for the other reaction compartments and/or slide support elements when a particular individual reaction compartment and/or slide support element is being cleaned or repaired. Each reaction compartment and/or slide support element can be separately cleaned and/or sterilized by steam, with or without a detergent or sterilizing reagent and dried with heated (below 100° C.) or super heated (above 100° C.) air. This type of sterilized cleaning could be used for example if a biological specimen that was being processed had infectious properties. Each reaction compartment essentially has the properties of an individual self-regulated and controlled miniature autoclave. Sterilization of each reaction compartment prior to use with the next biological specimen process can provide an inherent technical advantage due to the elimination of cross contamination and direct contact with infectious biological specimens. Sterilization can be performed using steam alone, or chemicals dispensed by a reagent pack or another dispensing element.

In a preferred embodiment of the invention, particular reagents are supplied to the reaction compartment and/or slide on the slide support element from a reagent pack (also referred to herein as a reagent dispensing strip or pack) individualized for a single reaction compartment and/or slide on the slide support element as described in more detail in FIGS. 1-22 and 39-78 of Published PCT application WO 2006/127852 and elsewhere herein (e.g., FIG. 40-42). Due to the extensive discussion of such reagent packs described therein, it is not considered necessary to provide further explanation in the present disclosure except to the extent that further embodiments or details of operation are newly presented herein.

While the invention is now described herein in connection with certain embodiments and examples so that aspects thereof may be more fully understood and appreciated, it is not intended to limit the invention to these particular embodiments and examples. To the contrary, it is intended to cover all alternatives, modifications and equivalents as may be included within the scope of the invention as defined by the claims below. Thus, these examples and embodiments, which include preferred embodiments, will serve to illustrate the practice of this invention, it being understood that the particulars shown are by way of example and for purposes of illustrative discussion of various embodiments of the present invention for providing various principles and aspects of the present invention.

Moreover while various systems, devices, components, and apparatuses of the invention are described herein in particular embodiments and examples, it is intended that all such systems, devices, components and apparatuses be interchangeable in regard to the various combinations thereof which may be envisioned as embodiments of the invention described and claimed herein as long as such other embodiments which are not explicitly herein function in accordance with the present invention. For example, the various types of reaction compartments, slide support elements, heating elements, reagent pack support devices, dispensers, plungers, closure and sealing means, chambers, pressurization apparatuses, and spreading devices, to list but a few, can replace each other in various alternative embodiments of the invention.

Embodiments of FIGS. 1-6

Turning now to the figures, shown in FIG. 1 is a microscope slide staining system designated by the general reference numeral 2. The microscope slide staining system 2 in one embodiment comprises a staining apparatus 10, a remote reagent source 4 operatively connected to the staining apparatus 10, a waste collection system 6 operatively connected to the staining apparatus 10, and a microprocessor operatively connected to the staining apparatus 10, and preferably to the remote reagent source 4 and waste collection system 6. The remote reagent source 4 of the microscope slide staining system 2 preferably has a self-contained D.I. water, buffer, and/or reagent liquid production and management module which is operatively attached to the staining apparatus 10. The remote reagent source 4 is also referred to elsewhere herein as a "reagent module" or as a "remote reagent source". This reagent module 4 can be plumbed to the staining apparatus 10 for "on-demand" efficient production of rinse buffers, antigen retrieval solution, or any type of liquid reagent used in treatment of microscope slides. The reagent module 4 can provide buffers or reagents like wash rinses, antigen retrieval solutions, fixation solutions hydration solutions, dehydration solutions, mineral oil solutions, surfactants solutions, ionic and or non-ionic additives solutions, buffer solutions, D.I. water rinses solutions, polyol additives solutions, alcohol solutions, xylene solutions, limonene solutions, Tween solutions, Brij solutions, and other reagents or solutions. The reagent module 4 can provide liquids for use in the staining apparatus 10 by filling a bulk bottle, bottles, or storage reservoir to be used by the staining apparatus 10. The bulk bottles would be operatively connected to each set of reaction components or to each reagent dispenser or to a dispenser of the X-Y-Z positioning device for use therein. The reagent module 4 can be connected to a known D.I. water source in the lab or can be plumbed to a tap water source to produce D.I. water in-situ. The regent module 4 may comprise reagent canisters (not shown) which are operatively connected in a series or parallel for different types of liquids to be dispensed in the staining apparatus 10.

Different types of reagent canisters can be employed by the reagent module 4 to produce different types of liquids for the staining apparatus 10. Each reagent canister can produce its own "type" of "liquid" for use. The reagent module 4 may have a plumbed water supply, an electrical connection, and conduits or plumbing to the staining apparatus 10 for a closed system of operation. The reagent canisters may contain chemicals in a solid, liquid, gel, semi-solid, colloidal, or any known physical state for treating a water source to produce a "ready to use" or "on demand" production of reagents for the staining apparatus 10. The reagent canisters of the reagent module 4 can be plumbed in a series or parallel to facilitate removal and replacement of the reagent canisters when the staining apparatus 10 is in operation. There can be two or more of one specific "type" of reagent canister plumbed in a series or parallel on the reagent module to facilitate the removal of one empty canister, while the other or others are still in operation. In one embodiment, operation of the staining apparatus 10 does not have to be stopped to add or replace a reagent canister while the reagent module 4 is in use. The microprocessor 8 of the staining system 2 or a microprocessor in the reagent module can alert the technician to replace or remove a used or empty reagent canister. In a preferred embodiment of the reagent module 4, the reagent module 4 is plumbed in line with a tap water source or DI water source to the staining apparatus 10. The staining apparatus 10 could use a salt-free rinse solution, for example, produced by the reagent module 4 comprising deionized water (DI water) with an ionic detergent, non-ionic detergent, cationic detergent or surfactant present. The tap water plumbed to the reagent module 4 can be deionzed, distilled, purified, and or sterilized by the reagent module 4 by UV irradiation, and/or chemicals present in one of the canisters in the reagent module 4. If DI water is initially plumbed to the reagent module 4, the DI water can be treated similar to non-DI water or tap water to produce a very high quality sterile DI non-salt rinse with a surfactant present. The reagent module 4 may also be constructed to provide antigen retrieval solutions with different types of salts or surfactants known in the art of antigen retrieval solution or antigen unmasking solutions. These chemical or solutions are well known in the art. Antigen unmasking solutions can be, for example, citrate buffer, EDTA, antigen retrieval solutions having a pH in the range of 1-14, urea, with or without surfactants or detergents like Tween, Brij, IGEPAL, SDS, glycols, polyols, alcohols, and other ionic or non-ionic surfactants or detergents known in the art or others described elsewhere herein. This is a very convenient and economical way of providing these buffers or reagents "on demand" and delivering the buffers or reagents to the individual reaction components of the staining apparatus 10 without stopping or interrupting the slide being processed on the staining apparatus 10. The microprocessor 8 can alert the technician that one or more reagent canisters in the reagent module 4 are to be removed or replaced. The fittings on the reagent module 4 and reagent canister therein can be of any type of "quick connect" or "quick disconnect" component know in the art for liquid distribution connections. This concept of removing or replacing the reagent canisters "on the fly" without stopping the slide staining processes, complements the "independent access" of the staining apparatus 10 of the present invention. All prior art automated slide strainers have to, at some time, stop the slide staining process to either replenish, replace, or add reagents to their staining apparatus 10 during slide processing or before starting a new staining protocol. This embodiment of the present invention eliminates the need to stop the staining apparatus 10 merely to replace, change, or refill reagents required to stain a biological specimen on a microscope slide while the staining apparatus 10 is in operation processing at least one biological specimen on a microscope slide.

In a further embodiment of the present invention, as indicated in FIG. 1, the microscope slide staining system 2 comprises a self-contained waste collection system 6 also referred to herein as a "waste module 6" or "waste management module". This waste module 6 is operatively connected to the staining apparatus 10 for treatment of hazardous wastes or biological wastes or other wastes produced therein. The waste module 6 treats "on demand" both solid and liquid wastes. The waste module 6 preferably can separate liquid waste from solid wastes. The waste module 6 can treat the solid and liquid waste to produce non-hazardous waste that can be disposed by the laboratory disposal services. The waste module 6 preferably can separate hazardous waste from non-hazardous waste. If a hazardous waste can't be decontaminated by the waste module 6, the module will place the solid or liquid non-treatable waste into a sealed container (not shown) that can be disposed by lab personnel without the need to place the removable and disposable hazardous waste container in any other container for disposal. The waste container to be disposed will have fitted on its self a "break-away" fitting to seal the waste container from the lab's environment. The waste module 6 is preferably plumbed in a series or parallel to provide waste management while the staining apparatus 10 is in operation. The waste module 6 can decontaminate several hazardous wastes like, but not limited to DAB, Fast Red, Special Stains, Xylene, alcohol, chromogens, reagents, buffers, infectious and biological waste, etc. Each hazardous chemical, liquid, gas, or solid can be decontaminated by its own decontaminating canister or non-treatable waste can be separated into disposable waste canisters. Each decontamination canister can be separately removed or replaced on demand without stopping the staining apparatus 10 during operation.

The schematic in FIG. 1 is intended to representative of any microscope slide staining system contemplated herein and may comprise components of any of the invention embodiments described or contemplated herein in any combination which functions in accordance with the treatment, staining, and pressurization aspects of the present invention.

Figure 2:
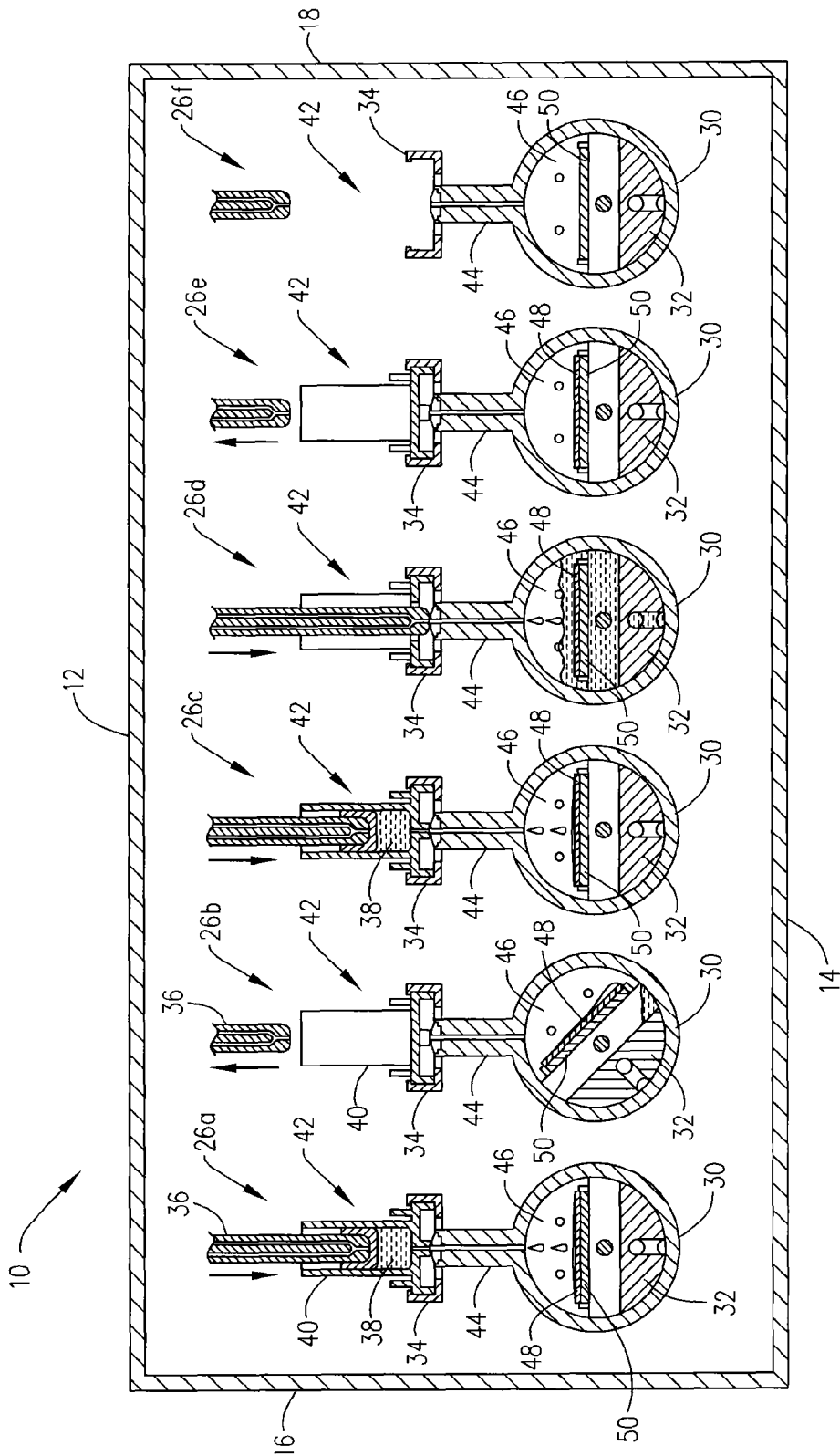
FIG. 2 is a front cross-sectional view of a staining apparatus of a microscope slide staining system of the present invention.

Shown in greater detail in FIG. 2 is the staining apparatus 10 of the microscope slide staining system 2 of the present invention. Staining apparatus 10, shown in FIG. 2, is substantially the same as the single chamber 282 shown in FIG. 85 of U.S. Ser. No. 11/439,722, comprises a top upper wall 12, a bottom wall 14, first side wall 16 and second side wall 18. The staining apparatus 10 further comprises a front wall 20 (FIG. 3A), a back wall 22 (FIG. 4), and an inner space 24. Contained within the inner space 24 are a plurality of sets of reaction components 26 (also referred to herein as reaction modules). FIGS. 2-6 and 34-36 show six sets of reaction components 26a-26f in the staining apparatus 10, but this is for illustration only. In other embodiments of the staining apparatus 10 any number of sets of reaction components 26 may be present, for example, less than or more than 6, such as 4 to 50 sets of reaction components 26.

Each set of reaction components 26a-26f comprises, in the embodiment of the invention of FIG. 2, a reaction compartment 30, a slide support element 32 for supporting a microscope slide 48, a reagent pack support device 34 for supporting a reagent pack 42, and a dispenser plunger 36 for causing expulsion of a reagent from a reagent container 40 of the reagent pack 42 onto the microscope slide 48. The dispenser plunger 36 (also referred to herein in some embodiments as a dispensing element) may move in an upward or downward direction for being positioned to dispense a reagent 38 onto the microscope slide 48. For example, in FIG. 2, reaction components 26a and 26c show the dispenser plunger 36 forcing the reagent 38 from the reagent container 40 of the reagent pack 42 which is positioned on a reagent pack support device 34. The reagent 38 is forced through a reagent conduit 44 of the reaction compartment 30 into an inner space 46 thereof onto a microscope slide 48 placed upon the slide support element 32. The dispenser plunger 36 is then withdrawn from the reagent container 40 (as shown for reagent components 26b and 26e). In some cases the dispenser plunger 36 is able to cause expulsion of a reagent 38 from the reagent pack 42, and is also able to separately dispense a reagent delivered from a remote reagent source 4. In other embodiments, these functions may be performed by separate devices such as the dispensers 319 and 320 described in further detail below in regard to FIG. 29A for example. The microscope slide 48 may be heated by a heating element 50 which is positioned on the slide support element 32 underneath the microscope slide 48. As is indicated in FIG. 2, each set of reaction components 26 can be in a different phase of operation independently of each other. For example, in FIG. 2, reagent 38 is being dispensed onto the microscope slide 48 in reaction components 26a and 26c. Reagent 38 is being removed from slide support element 32 by tilting thereof in reaction components 26b. In reaction components 26d, the inner space 46 of the reaction compartment 30 has been flooded with a reagent 38 for treating or rinsing the microscope slide 48. In reaction components 26e, the dispenser plunger 36 has been removed from the reagent pack 42, reagent 38 has been removed from the microscope slide 48 and the slide support element 32 is in an "upright"

position for allowing further treatment or disposition of the microscope slide 48. In reaction components 26f, the reagent pack 42 has been removed from the reagent pack support device 34 and the slide support element 32 is without a microscope slide 48.

Figure 3B:
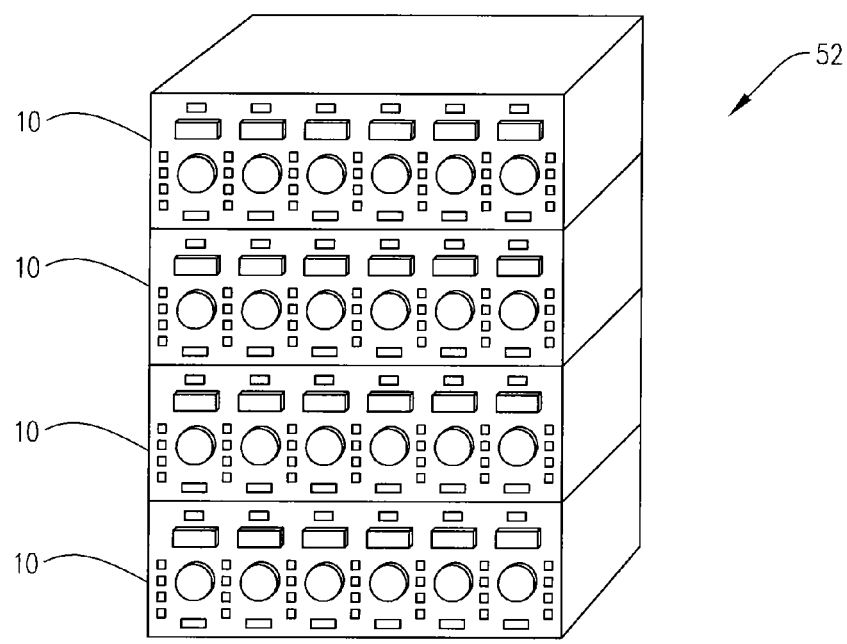
FIG. 3B is a perspective view of a microscope slide staining system of the present invention having four staining apparatuses such as the apparatus of FIG. 3A.
Figure 3A:
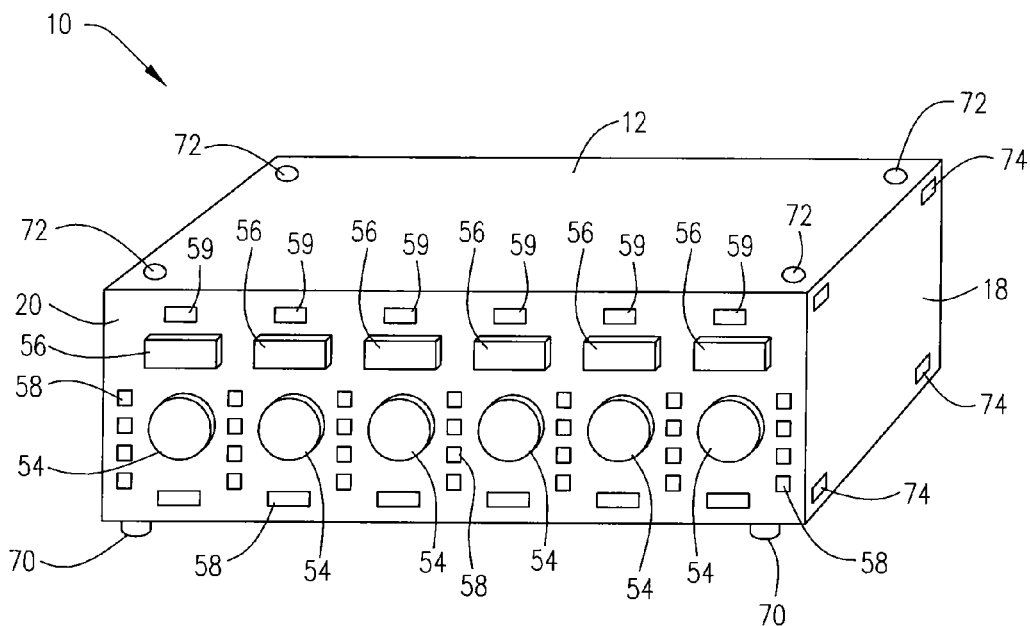
FIG. 3A is a perspective view of the staining apparatus of FIG. 2.

FIG. 3A shows a perspective view of the embodiment of the staining apparatus 10 of FIG. 2. The front wall 20 of the staining apparatus 10 comprises a plurality of slide support element doors 54 which can open (see FIG. 5) to allow the slide support elements 32 to be ejected from the staining apparatus inner space 24, or returned to the inner space 24. Similarly, the front wall 20 of the staining apparatus 10 comprises a plurality of reagent pack support device doors 56 which can open to allow the reagent packs 42 to be inserted into or ejected from the reagent pack support devices 34 for use in a treatment protocol, or after such use. Additionally, the reagent pack support device 34 can be constructed so as to be able to be ejected from the staining apparatus 10 through the door 56 (or without a door) for removal of a reagent pack 42 therefrom, or for placement of a reagent pack 42 thereon. The reagent pack support device 34 can then be returned (reinserted) into the inner space 24 of the staining apparatus 10 for treatment of the microscope slide 48 on the slide support element 32. The reagent pack support device 34 can, in an alternate embodiment, be positioned inside the staining apparatus 10 and only the reagent pack 42 is inserted into the reagent pack loading/removal opening (with or without an access door 56) wherein the reagent pack support device 34 "captures" or "grabs" the reagent pack 42 and pulls the reagent pack 42 into the staining apparatus 10 (like a CD-player in an automobile). When the reagent pack 42 is inside the staining apparatus 10 the microprocessor can recognize the reagent pack 42 and initiate the particular treatment protocol associated with that reagent pack 42. The reagent pack 42 may move outside and inside the staining apparatus 10 during staining to line up the desired reagent container thereon or can remain entirely inside the staining apparatus 10 during staining and only be moved outside of the staining apparatus 10 when ejected for disposal.

The staining apparatus 10 of FIG. 3A further comprises one or more of indicator lights, buttons, or gauges 58 and at least one display panel 59 which correspond to a particular slide support element, reaction compartment or reagent pack or reagent pack support device. For example, one indicator light, button (e.g., an eject/insert button), or gauge 58 may be used to cause a door 54 or 56 to open or close, or slide support element 32 to be inserted, or may indicate that the component is "on" or "off", or may indicate some physical parameter associated with the component, such as its temperature, pressure, or operational status. The display panel 59 may show the status or identify of the treatment protocol or reagent 38 to be used or currently in use in the reaction compartment 30.

Shown in FIG. 3B is a multi-staining apparatus version of the microscope slide staining system of the present invention designated by reference numeral 52 which comprises four staining apparatuses 10. Each staining apparatus 10 is indicated as containing 6 sets of reaction components 26. As noted above, the staining apparatus 10 may contain any number of sets of reaction components 26 (also referred to herein as reaction modules), for example from 4-50 sets and each microscope slide staining system of the invention may comprise one or more staining apparatuses 10. For example, in the microscope slide staining system 2 of the present invention, a single staining apparatus 10 may comprise the entire treatment unit of the staining system of the invention. The staining apparatus 10 may be arranged vertically of horizontally or in any configuration suitable for operating and the staining apparatus 10 may be constructed so that the sets of reaction components 26 are arranged in an arcuate pattern relative to one another within the staining apparatus 10 rather than linear.

Figure 4:
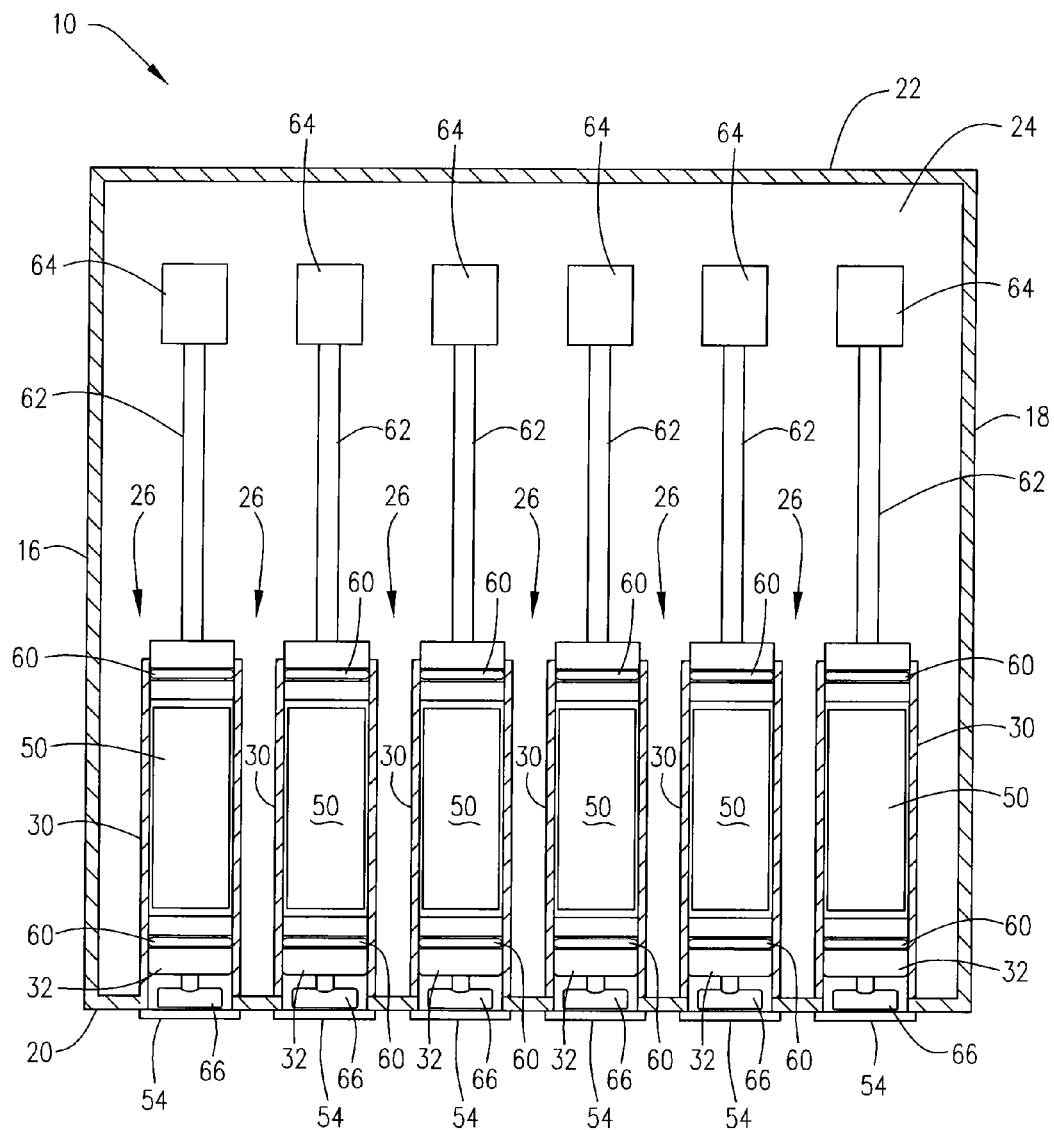
FIG. 4 is a top plan view of the staining apparatus of FIG. 3A.

Shown in FIG. 4 is a top plan view of the staining apparatus 10 of FIGS. 2-3B comprising reaction components 26 including reaction compartments 30, and slide support elements 32. Each slide support element 32 has sealing means 60 (such as O-rings or ground glass surfaces). Each slide support element 32 in this embodiment is connected by a shaft 62 to a motor 64 for pushing the slide support element 32 in a forward direction for ejection from the inner space 24 of the staining apparatus 10 and/or reaction compartment 30, for loading or removal of a microscope slide 48, or in a reverse direction for retracting the slide support element 32 into the staining apparatus inner space 24 and/or the reaction compartment 30 for treatment of the microscope slide 48. Optionally, each slide support element 32 may have a handle 66 for manually pulling or pushing the slide support element 32 into or out of the staining apparatus 10.

Figure 5:
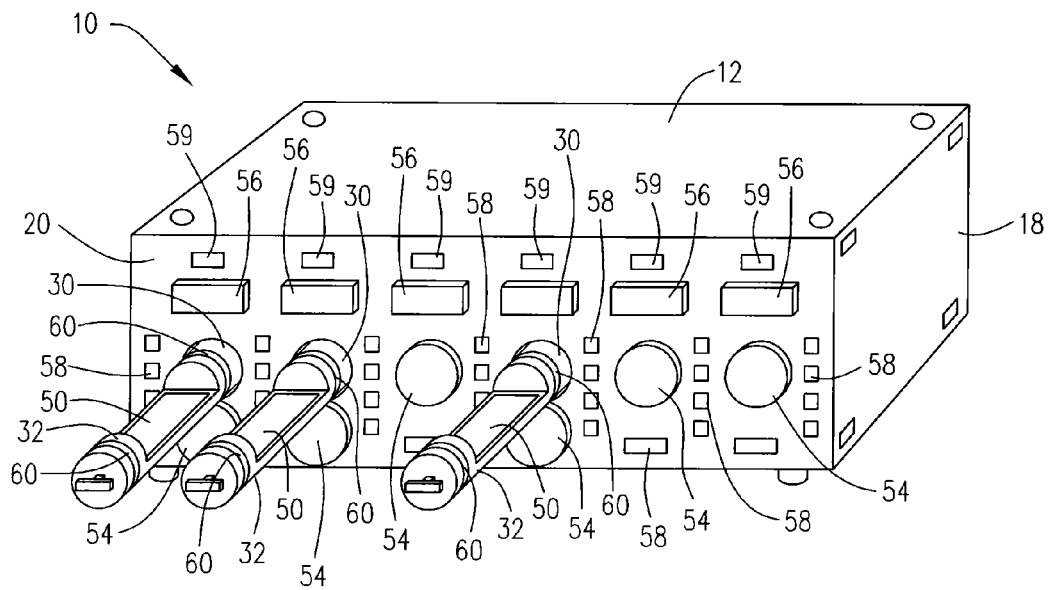
FIG. 5 is a perspective view of the staining apparatus of FIG. 3A shown as having three slide support elements ejected from the inner space of the staining apparatus.
Figure 6:
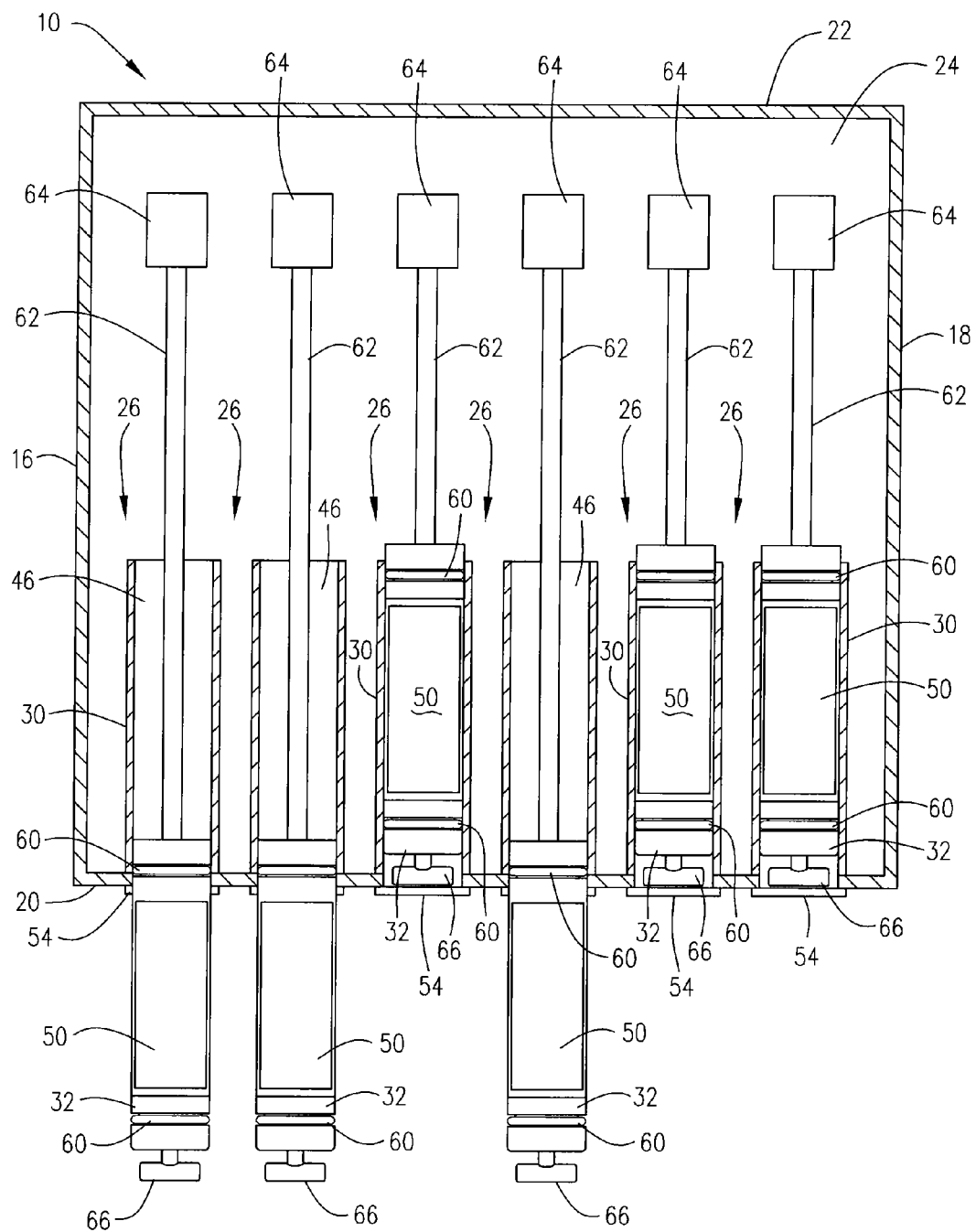
FIG. 6 is a top plan view of the staining apparatus of FIG. 5.

FIG. 5 shows the first, second, and fourth slide support elements 32 from the left ejected from the staining apparatus 10, in positions for placement of microscope slides 48 thereon. FIG. 6 is a top plan view of the staining apparatus 10 of FIG. 5 wherein the first, second and fourth slide support elements 32 from the left are shown in a placement or removal position outside of the inner space 24 of the staining apparatus 10. The motors 64 have caused extension of the shafts 62 causing expulsion of the slide support elements 32 from the corresponding reaction compartments 30, which in this embodiment are preferably open-ended.

The slide support elements of the invention preferably can be automatically moved in any position while the reaction compartment is pressurized (positively or negatively) with or without a heating means to heat the reagent under said positive or negative pressure. Said heating means can be a conductive, convective, and/or radiant heating element incorporated in or adjacent to the slide support element for heating the microscope slide and a biological specimen thereon. The slide support elements can be moved independently forward, backward, rotated along a longitudinal axis, and/or tilted, while the reaction compartment's inner space in under positive or negative pressure. Such movement of the slide support element, does not cause the positive or negative pressure to be expelled or otherwise "leak out" of the inner space of the reaction compartment since the slide support element is sealed therein. The seal of the slide support element to the reaction compartment causes retention of the pressure (positive or negative) held in the inner space of the reaction compartment during movement of the slide support element in within the reaction compartment. This movement, which does not alter the pressure in the reaction compartment, would be advantageous when it is desired for the microscope slide to be moved when the reaction compartment is under positive or negative pressure, e.g., during a treatment protocol. For example, the reagent contacting the biological specimen on the microscope slide present on the slide support element can be mixed or agitated by mechanical movement of the slide support element under positive or negative pressure. This movement for mixing the reagent on the microscope slide can be, for example, a forward and alternating backward movement along with a tilting from side to side movement to cause a circular rotation of the reagent on the microscope slide. Further, the microscope slide can be rotated completely or partially to an upside down position (0° to 180° from its original upright horizontal staining position, for example) and rinsed under pressure to remove the reagent on the microscope slide. Any protocol step requiring movement of the slide support element under positive or negative pressure is contemplated. The movement contemplated above can be employed for mixing, rinsing, or otherwise treating the microscope slide with a protocol that has at least one step which benefits from, requires, or otherwise needs the microscope to be moved or mobile under positive or negative pressure, for example, for rinsing the slide and retaining the slide to the main treatment position. It also preferred that the slide support element is moveable at any time under or not under pressure. The slide support element can be moved forward, backward, and rotated 360° in relation to the stationary reaction compartment. Alternatively, the reaction compartment can also move relative to the stationary slide support element in a forward, backward, or 360° rotational movement.

In the staining apparatus of any of the embodiments contemplated herein the chamber may be constructed so that a portion of the front wall, upper wall, bottom wall, back wall, and/or side walls, can be detached or opened to enable access to the inner space of the staining apparatus for removal, replacement, repair, or insertion of any of the reaction components therein. For example, a portion of the front wall in front of a slide support element or reaction compartment can be removed to enable replacement thereof, without having to access or disturb other sets of reaction components.

In an alternate embodiment of the invention, the apparatus is an automated biological processing instrument having a pressurizable common chamber (e.g., see FIGS. 35 and 36) that can hold a plurality of microscope slides on a plurality of independently movable slide support elements in the pressurizable common chamber, wherein the slide support elements are automatically and independently movable inside the processing chamber while the common chamber is under positive or negative pressure with or without heating means to heat reagents on the microscope slides while under said positive or negative pressure. Said heating means can be a conductive, convective, and/or radiant heating element incorporated in or adjacent to the slide support element. The movements of the slide support elements are independent of each other while in the pressurizable common chamber and microscope slides therein are under positive or negative pressure. In an alternate embodiment, the slide support elements are positioned on a common platform which is movable, wherein a plurality of slide support elements under positive or negative pressure are movable together with or without heating means to heat reagents disposed on the microscope slides.

The automated biological processing apparatus contemplated herein can have movable biological processing devices (e.g., reagent dispensers) that move over or around the microscope slides on the slide support elements whether the microscope slides and slide support elements are movable (or in movement) relative to the processing devices or are in a fixed position while being under positive or negative pressure (and with or without a heating means to heat a reagent associated with the microscope slide). As contemplated herein, said biological processing devices can be (but are not limited to) reagent-air mixing gas jets, rinse dispensers, air knives for blowing off reagents, reagent dispensers to dispense reagents (such as antibodies, stains, molecular probes, detection reagents, RNA probes, DNA probes, in-situ hybridization reagents, evaporation inhibition oils, or detection reagents or other reagent elements contemplated herein), Optical Recognition Characters (ORC) code readers, machine readable devices to read codes or symbols, reagent spreaders, or any other processing devices known in the art of processing biological specimens on biological supports.

In preferred embodiments, the present invention comprises automatically, independently, and/or simultaneously movable slide support elements and/or automatically, independently, and/or simultaneously movable biological processing devices and/or reaction compartments, under positive or negative pressure which are openable while a reagent associated with a biological specimen on the microscope slide on the slide support element is being heated by a conductive, convective, and/or radiant heating element incorporated into or adjacent to the moveable slide support element and/or movable biological processing devices and/or movable reaction compartments. All such movable components present inside the staining apparatus of the apparatus can automatically move under positive or negative pressure wherein a reagent associated with a biological specimen on the microscope slide on the slide support element is heated by heating means present in or adjacent to the slide support element or microscope slide. Preferably these movements of the movable components present in the staining apparatus (or reaction compartments) under positive or negative pressure, with or without heat, do not release or otherwise change the positive or negative pressure within the staining apparatus (or reaction compartments) while the components are in motion.

Figure 34:
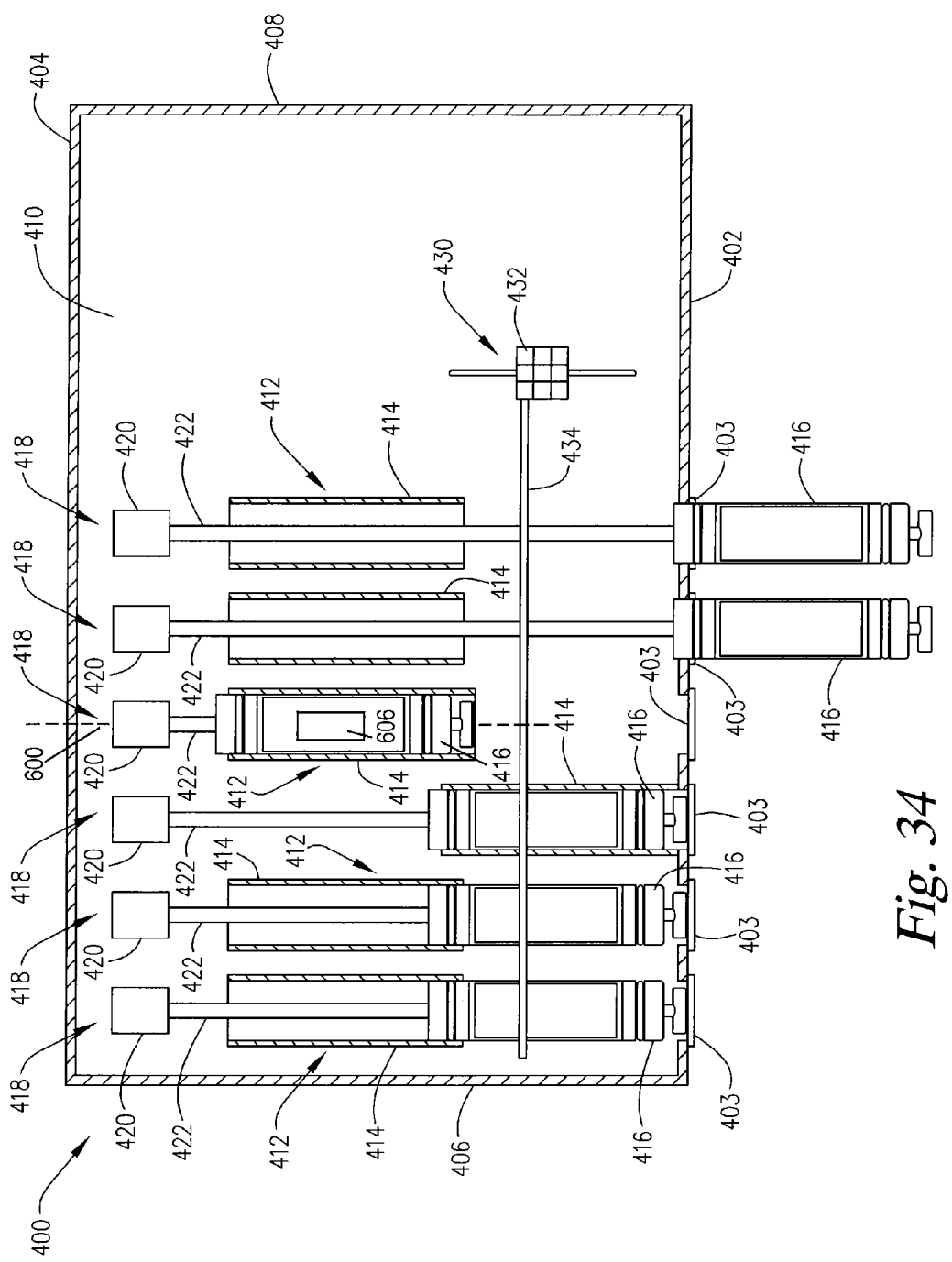
FIG. 34 is a top plan view of an apparatus of the invention similar to the apparatus of FIG. 4 except additionally having an X-Y-Z positioning apparatus comprising a dispenser head and a rotary reagent carousel comprising a plurality of reagent vials for dispensing reagents onto the microscope slides.
Figure 35:
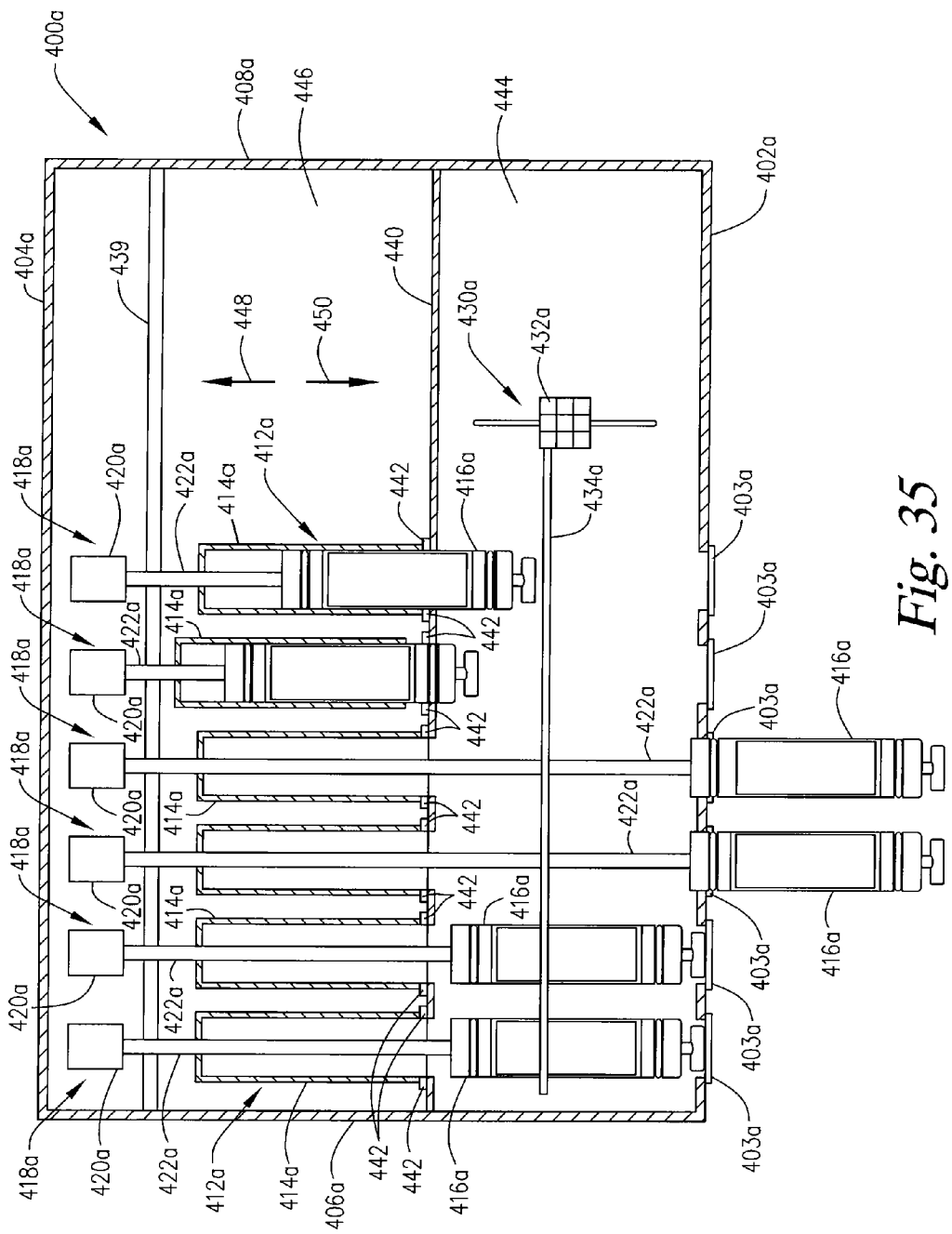
FIG. 35 is a top plan view of an apparatus similar to the apparatus of FIG. 34 except further having a separate pressurizable common chamber isolated from an application chamber in which reagents are applied to the microscope slides.

In an alternate embodiment of the invention, represented for example in FIGS. 34 and 35, the staining apparatus of the invention may comprise an X-Y-Z positioning device. X-Y-Z positioning devices are commonly used in the art of dispensing reagents to microscopes slides and other biological substrates. One commercially available X-Y-Z positioning device can be obtained from Tecan Group Ltd., 103 CH-8708 Mannedorf, Switzerland. The X-Y-Z positioning device comprises a movable head as a dispensing component and can be used to dispense reagents to the microscope slide on the slide support element outside or inside of the reaction compartment as described elsewhere herein. The X-Y-Z positioning device is able to move the movable dispensing component horizontally, laterally, or vertically to enable the movable dispensing head to be used as a dispensing device independently of the reagent pack or as an adjunct thereto.

In an alternate embodiment, the microscope slide staining apparatus may comprise a X-Y-Z microscope slide positioning device or a automated microscope slide positioning "robot" or a automated microscope slide positioning XYZ robot, referred herein as "robot" able to move a single microscope slide or a plurality of microscope slides as a group. A microscope slide positioning robot could be at least in part intergraded with the XYZ dispensing robot or be a stand alone robot. A microscope slide positioning robot can be configured like any automated robots know in the art of moving objects like microscope slides from one place to another in or around a microscope slide staining apparatus.

In another embodiment, a plurality of microscope slides can be transferred, translated, couriered, rotated, spun, or otherwise moved from any location around or in the microscope slide staining apparatus by a microscope slide positioning robot. A plurality or batch of slides can be transferred by a microscope slide X-Y-Z positioning robot or other positioning device to and from different zones or places in or around the automated microscope slide staining apparatus. One commercially available X-Y-Z positioning device that can be obtained, modified, and adapted for use is from Tecan Group Ltd., 103 CH-8708 Mannedorf, Switzerland. The X-Y-Z positioning device or robot comprises a movable head, device, lever, transfer head, or any other device that can capture, secure, and move a plurality or batch of microscope slides and move slides or batch of slides outside or inside of the microscope slide staining apparatus. A X-Y-Z positioning device is able to move the plurality of microscope slides horizontally, laterally, vertically, rotatably, or impart any other movement or motion to a plurality of microscope slides inside or outside the microscope slide staining apparatus. A microscope slide positioning device can move, rotate, spin, a plurality of microscope slides to and from zones associated with the microscope slide staining apparatus. An example of this embodiment is a plurality of microscope slides can be moved by the microscope slide positioning robot from a microscope loading zone or slide processing start zone, of the apparatus, to a flotation liquid removal zone, wherein the positioning robot would be able to spin the plurality of microscope slides at or in the liquid removal zone to remove the flotation liquid between a paraffin embedded biological specimen.

A microscope slide positioning robot can move at least one group of a plurality of microscope slides to any zone for processing the microscope slides. These processing zones, processing stations, or processing chambers, either in singular form or plural form, are here known as "zones," can be but are not limited to a microscope slide loading zone, flotation liquid removal zones, de-parffinizing zones, antigen unmasking zones, common pressure zones, common application zones, staining zones, cover-slipping zones, microscope storage zones, microscope slide removal zones, microscope slide finished zones, etc. A microscope slide positioning robot can move a plurality of microscope slides to and from any of the processing zones. A microscope slide positioning robot can impart all the motion movements (i.e., spin to remove flotation liquid from a plurality of microscope sides) necessary to produce a processed slide or the positioning robot can place a plurality of microscope slide in a position for another type of motion control device to impart the required motion to process a plurality of microscope slides. A microscope slide positioning robot can place a plurality of slides into a floatation liquid removal zone, for example, wherein a microscope slide positioning robot could move or translate the plurality of microscope slides to the liquid removal zone in such a way that the microscope slides are then captured and secured by a separate device associated with the floatation liquid removal zone to implement the required spinning of the microscope slides in the floatation liquid removal zone and once the floatation liquid is removed from the plurality microscope slides positioning robot could now capture, secure, and move the plurality of microscope slides to the next processing zone. There can be at least one microscope slide positioning robot(s) associated with the microscope slide staining apparatus. There can be at least one other motion control device associated with any processing zones if needed. A microscope slide positioning robot can do all the motions for processing a plurality of microscope slide or the microscope slide positioning robot can position or move the plurality of microscope slide to any processing zone where motion to the plurality of the microscope slides can be done by the motion device associated with a particular processing zone. A microscope slide positioning robot can move or translate a plurality of microscope slides being grouped or held by a microscope slide carrier, microscope slide rack, microscope slide tray, microscope slide holder, here known as a microscope slide rack. These microscope slide racks are known in the art for capturing, securing, or otherwise holding a plurality of microscope slides together as a group. A microscope slide rack, which can hold one or more microscope slides, can hold or orient a plurality of microscope slides vertically, horizontally, or any other microscope slide orientation needed for processing microscope slides in the staining apparatus. It is understood that a microscope slide rack (i.e., slide rack, slide tray, etc) can have at least one slide present in a slide rack, slide tray, etc. even though that slide rack, slide tray, etc. could hold more than one microscope slides at the time. A microscope slide positioning robot is moving the microscope slide holder.

This embodiment may use the reagent pack to dispense reagents in addition to reagents dispensed directly from the X-Y-Z positioning device. The dispensing head of the X-Y-Z positioning device can dispense reagents through conduits therein, as for the dispensing plunger which causes expulsion of reagents from the reagent pack. The dispensing head may comprise a distal portion forming a dispensing head which may have a pipette attached for dispensing reagents from an array of containers or the distal position could have disposable pipette tip attached that can be used and removed between application of each reagent. The dispensing head of the X-Y-Z positioning device can, in one embodiment, be used as the dispensing plunger to dispense reagents from the reagent pack or as an inkjet printer, an optical code reader, a scanner, or an aspirator.

All the heating elements of the present invention (e.g., the slide heater, reaction compartment heater, dispensing port heater, cavity heater, reagent strip holder heater, and the slide support heater (described below)) can be adapted to heat and sustain heating from about $1°$ C. to about $1000°$ C. The temperature of the reagent in the reaction compartment can be in the range of ambient, ($25°$ C.) or heated to $100°$ C. or greater. The reagent is preferably in the range of $25°$ C. to $400°$ C., and is more preferably in the range of $25°$ C. to $150°$ C. The temperature of the reagent when heated is preferably in the range of $100°$ C. to $160°$ C. More preferably, the temperature of the reagent is in the range of $101°$ C. to $150°$ C. More preferably, the reagent temperature would b in the range of $110°$ C. to $130°$ C. The reaction compartment can be pre-pressured by a separate gas source described in US Pat Applications 20060281116, 20060275889, and 20060275861 or the pressured gas can be produced by the compression of the "head space" of the reaction compartment described in detail below. The pre-pressure gas sent to the reaction compartment is also known as "pre-reaction pressure" The reaction compartment can have further pressure produced from the evaporation of the liquid reagent present on or around the microscope slide. An example being, the separate source of gas being brought to the reaction compartment to pre-pressurize the reaction compartment is say 25 psig. The heating source would heat the reagent around the microscope slide and/or heat the reagent on the microscope slide. The evaporating reagent around the microscope slide and/or the reagent on the microscope slide produced an additional 5 psig, for example. The total psig, for example, would be the initial 25 psig from the pre-pressure source plus the psig from the evaporated reagent totals 30 psig. This addition of the separate source of gas and the addition of the evaporated reagent total is known as the "total reaction pressure" or "TRP". The evaporating reagent producing pressure is directly related to the type of reagent being heated and its evaporation characteristics. The reagent evaporation pressure can be in the range of 0-10 psig, for example. Pressures for pre-pressurization, regular pressurization or in-situ pressurizations can be in the range of 0.01 PSIG to 1000 PSIG, more preferably in the range of 1 to 500 PSIG, and still more preferably, in the range of 10 to 150 PSIG.

In an alternate embodiment of the present invention, each of the slide support elements can support at least two microscope slides. Preferably each separate microscope slide would be heated by separate heating elements, but they could be heated by a common heating element. This slide support element which is able to hold at least two microscope slides would have a single reaction compartment for pressurized treatment of the at least two microscope slides on the single slide support element. This embodiment is optimally used in high volume microscope slide testing laboratories, wherein instead of one slide per slide support element and each slide support element having its own single reaction compartment, this embodiment would result in a decrease of the number of slide support elements which carry only a single microscope slide per slide support element. For example, in this embodiment, the staining apparatus could comprise 10 slide support elements each able to hold at least two slides. If the staining apparatus had 10 of these double slide support elements these 10 slide support elements would support 20 slides together if they were all in use for an initial treatment run of these 20 microscope slides. Preferably the staining apparatus would also comprise a plurality of slide support elements which support single microscope slides enabling the addition or removal of single slides onto and into the staining apparatus for independent access to the staining apparatus. Thus, individual single slides could be inserted or removed from the staining apparatus while the other double slide supports were already in operation. For example, in one embodiment of a staining apparatus able to treat 40 slides, there could be 10 double slide support elements holding 20 slides, and 20 single slide support elements for independent access to 20 slides enabling a total of 40 slides to be treated. The staining apparatus could comprise any combination of double, triple, (or more) slide support elements along with a plurality of single slide support elements in any combination of single or plural slide support elements. As stated above, if a slide support element is sized to support 2 or more microscope slides, this slide support element would have its own reaction compartment unique to itself for treatment of the slides thereon. If a movable slide support element, for example, held 3 microscope slides, this slide support element would be associated with its own reaction compartment for the pressurized treatment or treatment of the 3 slides present thereon. In an alternate embodiment, the staining apparatus may comprise separate reaction compartments that separately enclose or at least partially enclose the at least two or more microscope slides on the single slide support element, thereby enabling separate treatment of the at least two or more microscope slides even though they are movable together on the common slide support element. In an alternative embodiment the at least 2 microscope slide support elements can be moved into or out of a staining apparatus having a pressurizable common chamber for treatment of the microscope slides along with any single slide support element that is also capable of moving into or out of the staining apparatus with the pressurizable common chamber.

Embodiments of FIGS. 7-22B

Figure 7:
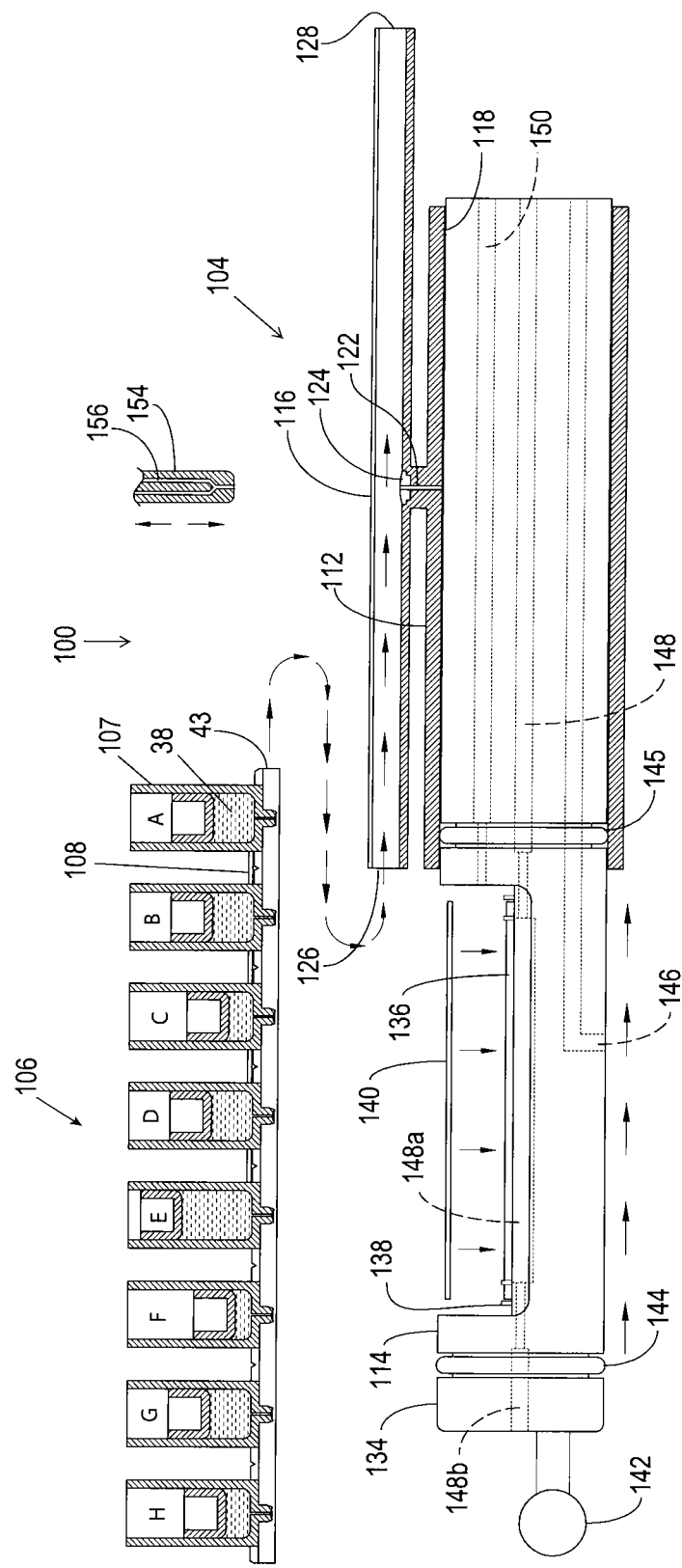
FIG. 7 is a cross-sectional side view of a set of reaction components (e.g., reaction compartment, slide support element, and reagent pack support device) in a staining apparatus of the present invention before the reagent pack has been inserted into the reagent pack support device, and before a microscope slide has been disposed on the slide support element. The walls of the staining apparatus are not shown for simplification.

Shown in FIGS. 7-22B are reaction components 104 of a staining apparatus 100 such as staining apparatus 10 of an analytic apparatus of the present invention having a cylindrical reaction compartment 112, a slide support element 114, and a reagent pack support device 116 for supporting a reagent pack, such as previously described elsewhere herein. A front wall 102 of staining apparatus 100 is shown in phantom. Preferably, the reaction compartment 112 has an inner diameter of 1.5-5 cm, and more preferably 2-3 cm, and more preferably 2.5-2.8 cm, and has a wall thickness of 2 mm to 3 mm. The length of the slide support element 114 is preferably 10-20 cm, and more preferably 12-15 cm. The length of the reaction compartment 112 is preferably 15-30 cm, and more preferably 18-22 cm. The reagent pack support device 116 in this embodiment is operatingly connected (e.g., attached at a top) to the reaction compartment 112 via a reagent conduit 122 in the reagent pack support device 116 or reaction compartment 112 which opens to an inner space 120 of the reaction compartment 112. There is an injector port orifice 124 in the reagent pack support device 116 which is adapted to receive an injector nozzle or port from a reagent container of a reagent pack 106. The reagent pack support device 116 has a front end 126 and a rear end 128. The reagent pack support device 116 functions to receive, support, move and eject a reagent pack 106 of the present invention and preferably can move upwardly and downwardly and forward and backward. The slide support element 114 has a base 134 which can reciprocatingly move into and out of the reaction compartment 112 and into or out of the staining apparatus 100. The slide support element 114 comprises a heating element 136 upon which a microscope slide 140 (like microscope slide 48) is placed. The slide support element 114 may optionally have a handle 142 which enables a technician to manually insert and withdraw the slide support element 114 from the reaction compartment 112 and staining apparatus 100. The slide support element 114 preferably further comprises a sealing means which in the embodiment of FIG. 7 is a front O-ring 144 and a rear O-ring 145 for providing a pressure resistant seal of the base 134 against the inner surface 118 of the reaction compartment 112. Other embodiments of sealing means which can be employed in the invention are described elsewhere herein. The slide support element 114 (and base 134) can be constructed from materials which include, but are not limited to, glass, quartz, Pyrex®, borosilicate, steel, metals, aluminum, composites, polymers such as polycarbonate and plastics or combinations thereof.

The slide support element 114 also preferably has a drainage port 146 for receiving and draining reagents and waste liquids from the reaction compartment 112. The slide support element 114 further preferably has one or more cooling ducts 148 which are operatively connected to a sub heating element cooling space 148a beneath the heating element 136, and one or more cooling duct exits 148b which evacuate the cooling air or liquid from the sub heating element cooling space 148a. The slide support element 114 preferably further comprises a first air/pressure duct 150 and a second air/pressure duct 152 for regulation of the pressure within the reaction compartment 112 as discussed elsewhere herein. The duct 150 and/or duct 152 or an additional duct (not shown) can be used for releasing and/or regulating pressure from the reaction compartment 112. The slide support element 114, as noted above, comprises a heating element 136 upon which the microscope slide 140 is placed for application of reagents thereon. The reaction components 104 may further comprise a thermocouple or other temperature measuring device for measuring temperatures of the slide or other components therein. Before operation the slide support element 114 is inserted by a sliding motion into the inner space 120 of the reaction compartment 112 (see FIG. 8A-8B). Also before operation the reagent pack 106 (or any other reagent pack described or enabled herein) is inserted into the reagent pack support device 116, for example, inserting a first end 43 of the reagent pack 106 into the front end of 126 of the reagent pack support device 116, wherein during operation the reagent pack 106 is moved in a direction toward the rear end 128 of the reagent pack support device 116. The reagent pack 106 may be advanced manually or automatically via a pulling or pushing device, including rollers or a track which incrementally advances the reagent pack 106 as instructed by a microprocessor. The reaction compartment 112 further comprises a reagent conduit 122 (like reagent conduit 44) for allowing passage of a reagent from the reagent pack 42 into the reaction compartment 112. The reaction components 104 also comprise a dispenser plunger 154 (also referred to herein as a dispensing element and similar to dispenser plunger 36 above), which has a dispensing canal 156 therein for allowing passage of another reagent or solution therethrough preferably from a remote source. The reagent pack support device 116 preferably has an injector port orifice 124 for receiving at least a portion of an injector nozzle 46 from a reagent container 107 of the reagent pack 106 during use thereof. The staining apparatus 100 may comprise a separate device (other than a dispensing element) for pressing reagents from the reagent pack 106 such as shown in the embodiments of FIGS. 29A-33H.

Figure 12:
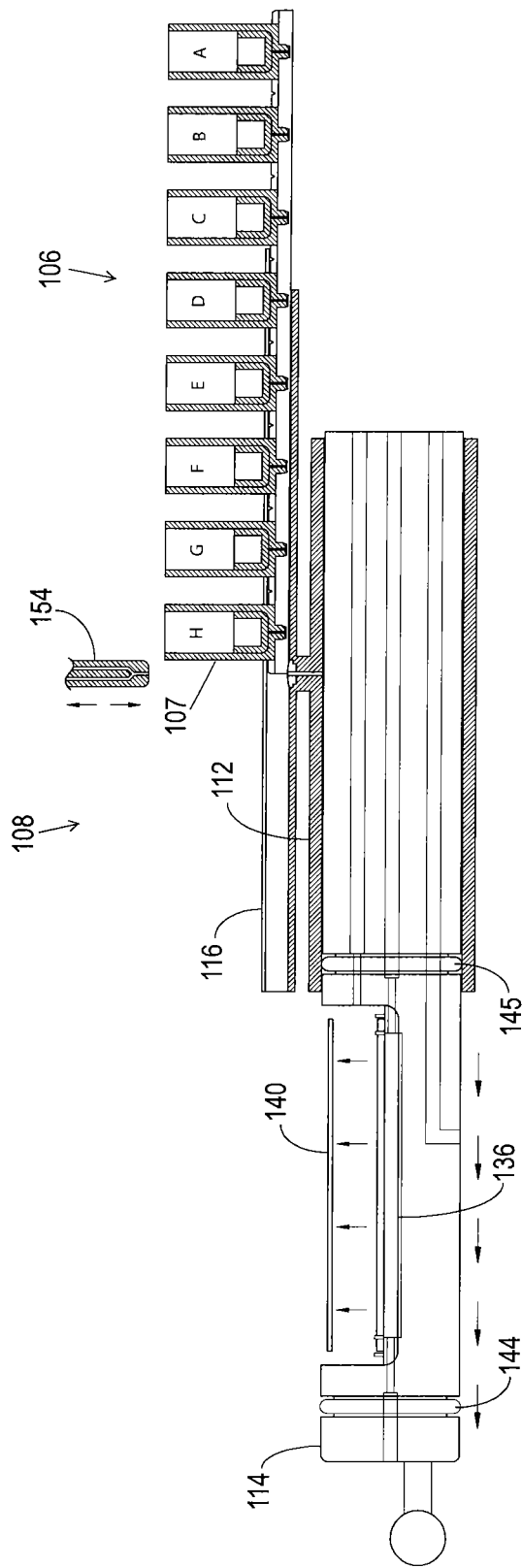
FIG. 12 is a cross-sectional view of the reaction components of FIGS. 7-11B after the reagent pack is completely used and the microscope slide is removed from the slide support element.
Figure 13:
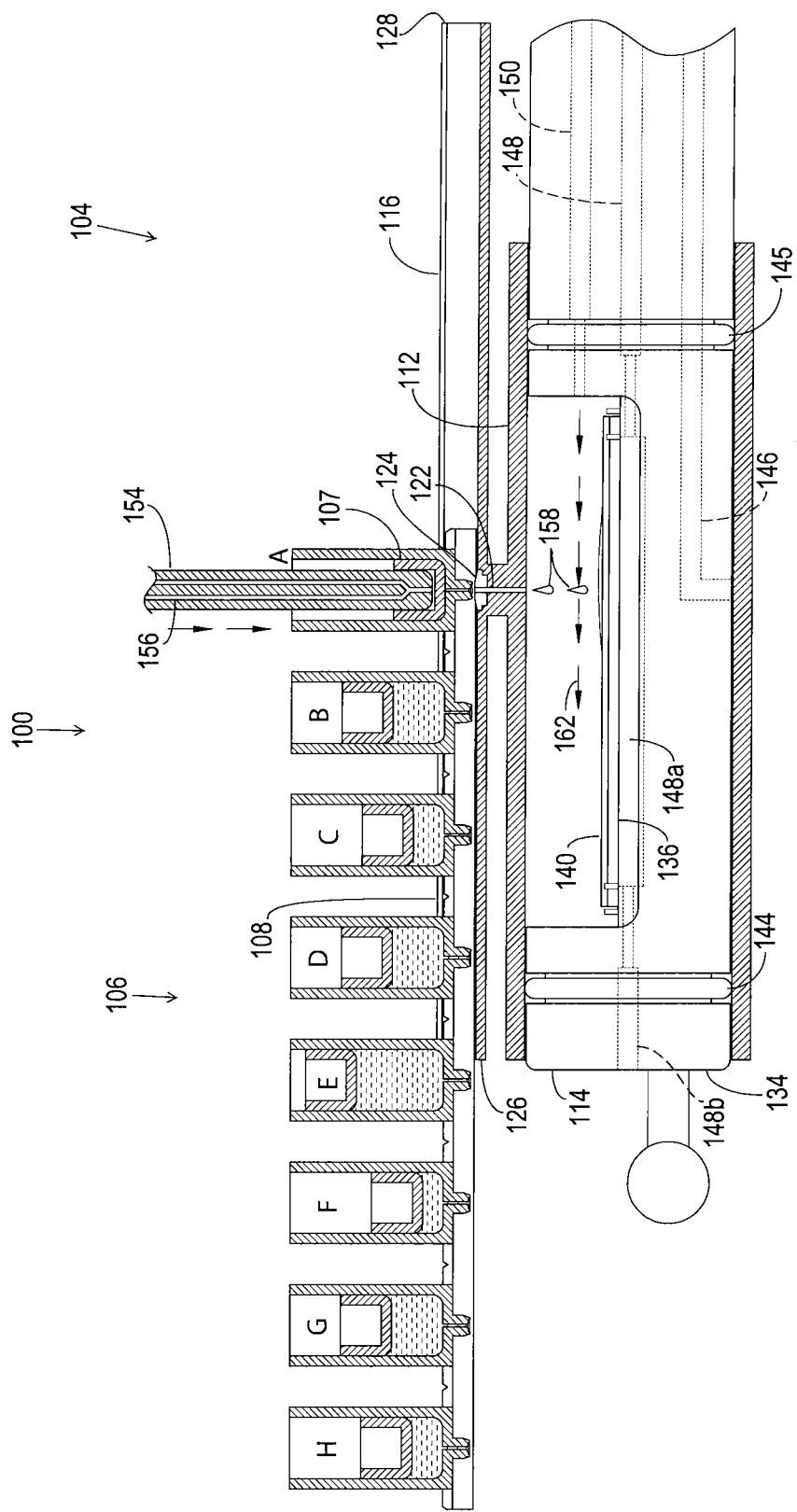
FIG. 13 is an enlarged version of FIG. 8A.
Figure 14:
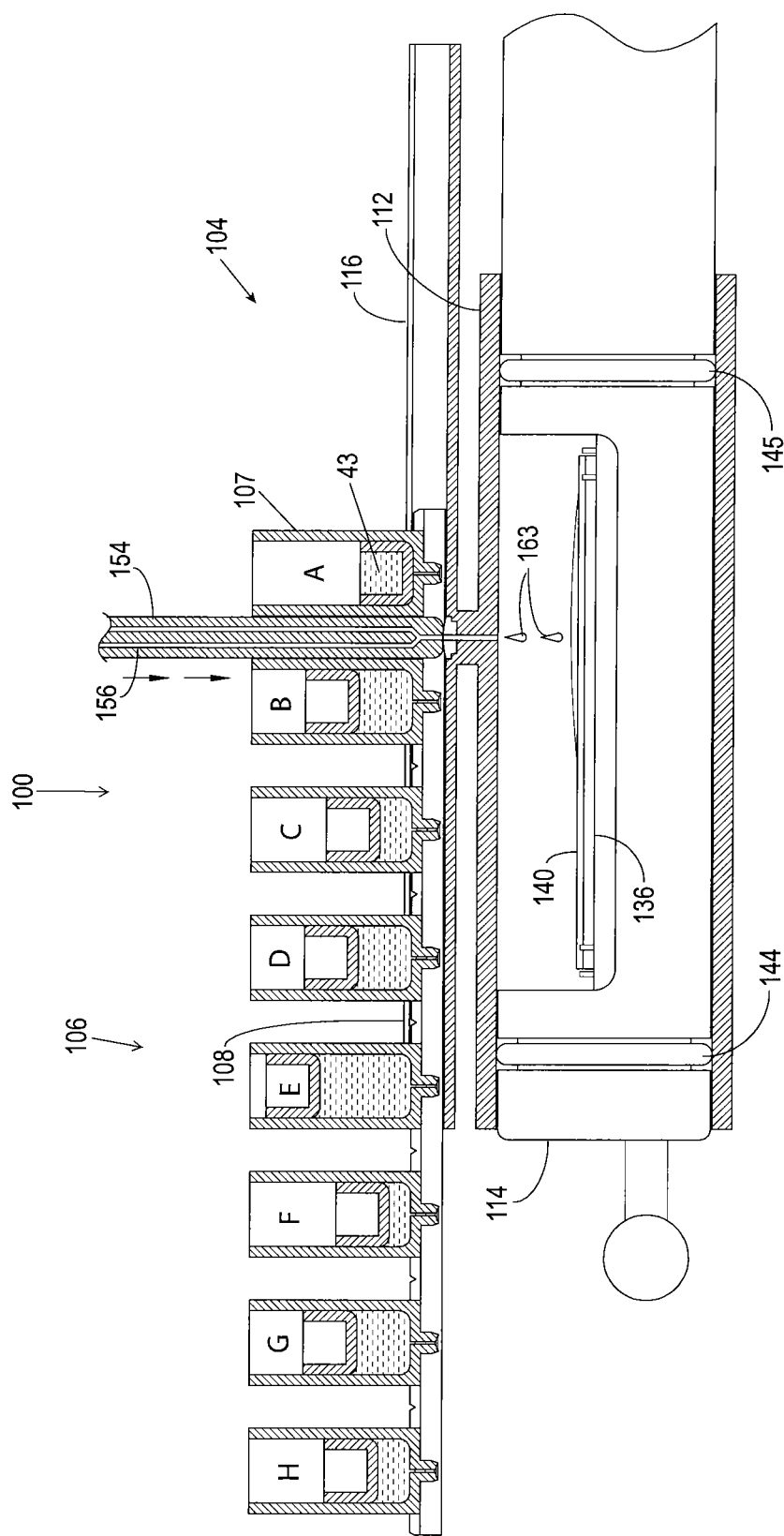
FIG. 14 is an enlarged version of FIG. 10A.

During operation, as shown in FIGS. 8A-8B and 13, a reagent pack 106 (or any other reagent pack described or enabled elsewhere herein) is inserted through a door not shown in front wall 102 into the reagent pack support device 116 as previously described and a reagent container 107 is positioned over the injector port orifice 124. The dispensing plunger 154 is extended downwardly into the reagent container 107 of the reagent pack 106 wherein it engages a piston, forcing the piston downwardly and causing ejection of the reagent 38 from the container 107 through the reagent conduit 122 and providing reagent 38 deposited onto the microscope slide 140. When the dispensing plunger 154 forces the piston 44 downwardly, a seal is maintained within the reagent container 107 and in a preferred embodiment enables maintenance of pressure within the reaction compartment 112. The reagent 38 can be mixed on the microscope slide 140, for example, by delivering bursts of air 162 through the first air/pressure duct 150 and the second air/pressure duct 152 as discussed in further detail below. In a subsequent step the dispensing plunger 154 may be withdrawn (FIGS. 9A-9B) and the base 134 of the slide support element 114 tilted within the reaction compartment 112 to allow the reagent 38 to drain from the microscope slide 140, forming a reagent drainage 160 which is collected in the drainage port 146, removed from the reaction compartment 112, and collected in a waste storage container (not shown). In a later step (FIGS. 10A-10B) the slide 140 is returned to an upright, horizontal position and the reagent pack 106 is advanced until the rinse port aperture 108 in the reagent pack 106 is positioned above the injector port orifice 124 wherein rinse solution 163 is delivered from a rinse solution reservoir (not shown). Furthermore, air or liquid may be delivered through the dispensing canal 156 in the dispensing plunger 154 to cause mixing of reagent 38 or to remove the reagent 38 from the microscope slide 140, or to enhance the rinsing of the reagent 38 or rinse solution 163 from the microscope slide 140 (e.g., see FIGS. 11A-11B). Finally as shown in FIG. 12, after all reagents from the reagent pack 106 have been dispensed, the portion of the slide support element 114 which carries the microscope slide 140 is withdrawn from the reaction compartment 112 wherein the microscope slide 140 is then removed from the slide support element 114. Note that FIGS. 13-14 are enlarged versions of FIGS. 8A and 10A, respectively and are provided herein for the purpose of more easily showing the steps therein.

FIGS. 15A-16B provide a more detailed description of how the bursts of air 162 delivered form the first air/pressure duct 150 and second air/pressure duct 152 can be used to cause mixing of the reagent 38 on the microscope slide 140. Preferably, the first air/pressure duct 150 and second air/pressure duct 152 are operated alternately to provide bursts of air 162 in alternating clockwise/counterclockwise directions to agitate the reagent 38. The first air/pressure duct 150 and second air/pressure duct 152 can also be used to pressurize the reaction compartment 112. At any desired time the heating element 164 can be used to heat the slide 140 and reagent 158 thereon as discussed in greater detail elsewhere herein. As shown in FIGS. 17-19B, after the microscope slide 140 is heated, it can be rapidly cooled by directing air or liquid via the cooling ducts 148 into sub heating element cooling spaces 148a which are located below the heating element 164 which in one embodiment is located below and is used to heat a hot plate 166 upon which the slide 140 is positioned. Air or liquid used for cooling can then pass through cooling duct exits 148b. In another embodiment, shown in FIGS. 20-22B a sub heating element cooling space 148c is similar to sub heating element cooling space 148a except the cooling air or liquid which passes through the sub heating element cooling space 148c is delivered via one of the cooling ducts 148 and exits the slide support element 114 via the outer cooling duct 148.

As shown in FIGS. 7-22B, each reaction compartment 112 of the staining apparatus 100 preferably comprises a hollow cylinder, preferably constructed of a thermoplastic resin or polymer (including but not limited to polycarbonate or any other polymeric material able to withstand elevated temperatures and pressures), glass, Pyrex®, quartz, other crystalline materials, and metals and metal alloys. The tubular nature of the reaction compartment 112 is preferred because the elevated pressures created within the reaction compartment 112 during its use are more evenly distributed therein.

The seal between the outer surface of the slide support element 114 and the inner surface of the reaction compartment 112 can be formed using O-rings, as shown in the FIGS. 23-38B or can be formed using an inflatable O-ring, a seal, or an inflatable seal depending on the shape of the mating surfaces. The sealing means can be constructed of plastic, polymer, thermoplastic, resin, ceramic, rubber, metal glass, or composite, for example.

Or in a preferred embodiment, sealing surfaces comprising an outer surface portion of the slide support element 114 and an inner surface portion of the reaction compartment 112 are made of a low tolerance ground or polished sealing surface. These sealing surfaces when engaged from a seal which replaces and eliminates the need for a ring seal or inflatable or seal raised above the mating surfaces. In this embodiment, the ground or polished mating surfaces alone, when joined together, produce a microscopic seal with a large surface area to seal the microscope slide within the reaction compartment 112 and which is able to maintain an elevated pressure therein (above atmospheric) even under high temperature conditions above 100° C. The material of the slide support element 114 and the tubular reaction compartment 112 can feature a very high tolerance ground or polished seal on the mating surfaces. In the preferred embodiment, the slide support element 114 and the reaction compartment 112 are made of a high tempered glass material like Pyrex®, or any material that can produce a ground or polished mating surface to form a seal which maintains a pressure above atmosphere pressure. The ground glass surface, or polished surface of the slide support element 114 against the ground or polished surface of the reaction compartment 112 yields an air-tight and pressure-tight seal when the two ground or polished surfaces are joined together, such that, there is no void space which must be filled by a raised surface such as an O-ring. This embodiment of the present invention thus eliminates the need for raised seals (e.g., O-rings) thus reducing maintenance cost for the replacement of separate seal components such as O-rings and increases simplicity and efficiency and seals the reaction compartment even under pressures above atmospheric levels (e.g., above 14.7 psig (101.325 kPa), i.e., above 0 psig (101.325 kPa)) and high temperature conditions above 100° C.

As noted herein, the staining apparatus (e.g., staining apparatus 10 or 100) of the staining apparatus of the present invention preferably comprise a plurality of sets of reaction compartments 112, such as shown in FIG. 7. Each set of reaction components 110 comprises a tubular reaction compartment 112 (although the reaction compartments may not be tubular, but may be rectangular, a slide support element 114 and in a particularly preferred embodiment a reagent pack support device 116. The reaction compartment 112 has an inner surface and an inner space into which the slide support element 114 can be moved for treating a biological sample on a microscope slide 140 thereon. The slide support element 114 is able to slide into and out of the reaction compartment 112 in a manner similar to a piston within a cylinder. When the slide support element 114 is withdrawn from the reaction compartment 112 and/or from the staining apparatus 100, a microscope slide 140 can be placed thereon or removed therefrom. The slide support element 114 can be inserted into the reaction compartment 112 for treatment of the biological sample on the microscope slide 140 as described elsewhere herein. As shown below, the slide support element, in a preferred embodiment) can be turned (tipped or rotated) within the reaction compartment 112 for facilitating the removal of reagents or fluids from the microscope slide 140 after the microscope slide 140 has been treated, as shown in the figures (e.g., see FIG. 9B). Reagents or fluids on the microscope slide 140 can be mixed by air circulation as shown in FIGS. 15A-16B for example or by rotational movement of the slide support element 114. After heating, the microscope slide 140 can be cooled by circulation of air or fluid thereunder, for example as shown in FIGS. 18A-22B. In another embodiment, the microscope slide 140 could be cooled by using a circulating liquid such as a reagent that becomes pre-heated by passing under the heated slide thus transferring heat to the circulating reagent which could then be dispensed onto the microscope slide 140.

The reaction compartment 112 of the present invention (or other reaction compartments) can be constructed of any material known in the art of high temperature and pressure compatible devices. These materials also include, but are not limited to, plastics, polymers, composites, ceramics, glass, quartz, metals and coated metals. The components of the reaction components 112 can be coated for resistance to porosity, to increase hydrophobic and hydrophilic properties, for ease of cleaning, chemical resistance, and stain resistance. These coatings could be, for example, Teflon®, fluoropolymers, any other known coating that would impart these desirable properties to all surfaces of reaction compartment 112 and slide support elements 114 and surrounding structures with a different coating being present on different portions of the apparatus. In one embodiment, for example, the inner surface of the reaction compartment 112 and outer surface of the slide support element 114 may be coated with a hydrophobic, chemical, and stain resistant coating to aid in the draining of the condensed reagents on the inner surface of the reaction compartment 112 or outer surface of the slide support elements 114 and ease of removal of reagents therefrom.

The slide support element 114 preferably has incorporated therein a heating element 136, and a hot plate (which may be one and the same) and which may include guide clips or pegs or elements to position and secure the microscope slide thereon. The tops of the clips may be positioned to be below an upper surface of the microscope slide, so as to prevent reagent on the slide 140 from being wicked off by the clips by capillary action.

In a particularly preferred embodiment, underneath the heating element 136 is one or more recessions (sub-heating element cooling spaces 148a) which are connected via cooling ducts 148 to a gas or liquid supply source to quickly cool the heating element 136 thereby quickly cooling the microscope slide and the reagent thereon.

The slide support element 114 and reaction compartment 112 can be constructed of any material suitable for use under pressurized conditions and resistant to corrosion by laboratory reagents, including but not limited to stainless steel, metals, plastics (clear or opaque), polymers (e.g., polycarbonate), tempered glass, and Pyrex® or other materials mentioned herein.

Containment of waste and used reagents from the staining apparatus will be now briefly discussed, (see further discussion above).

In a preferred embodiment the staining apparatus of the present invention (e.g., as represented in FIG. 1) has a waste collection system 6 which is operatively connected to the reaction components of the staining apparatus 10 by one or more fittings that can join multiple tubes or conduits. In a preferred embodiment of the present invention, this main fitting (not shown) can be joined to the waste container of the waste collection system (waste module) 6 (which may be disposable or non-reusable) by a breakable joint present on the waste container. This fitting on the waste container snaps together with the main fitting of the instrument. This attachment is secure and will not leak under pressure. When detached, this fitting on the waste container partially "breaks away" and leaves behind on the waste container an airtight, leakproof, tamper proof, non-removable seal. The residual piece that was detached from the waste container is removed by the technician and then is ready to be reattached to a new waste container. The waste container is now ready to be disposed of in its entirety by a technician or medical waste personnel. The tamper proof seal of the separated fitting protects the medical waste personnel from coming in contact with any of the waste in the sealed waste container.

In an alternate embodiment the detachable fitting on the waste container may not have any residual piece on the main instrument fitting but rather "breaks" or "snaps" away form the detachable piece on the disposable waste container cleanly.

In an alternate embodiment, the waste module 6 could comprise two or more waste containers wherein it is possible to remove one full waste container while retaining one or more other waste containers attached to receive waste from the working reaction modules. The microprocessor could alert the technician that a waste container is in need of replacing by a sensor located in the waste container. If the technician chooses to ignore the alert from the instrument, it could divert the waste to another waste container until the time is convenient to replace the full waste container. Since the staining apparatus operates each set of reaction components independently, the waste containers are set-up to receive waste from any one or more of the reaction components during operation thereby eliminating the need to stop operation of the instrument just to change any full waste container. The waste containers can be hooked up in a series or in parallel, as explained above) to keep at least one waste container active while any other waste container is being changed. The microprocessor is preferably in direct communication with all the waste containers and will shut down any waste route that leads to a fitting that has been detached and is in the process of replacement, repair, or cleaning.

In an alternate embodiment, the staining apparatus could have one main waste container which when full would alert the technician to start the waste recovery procedure. The main waste container could be drained to a secondary waste container to be disposed. The waste container can be charged with activated charcoal or other neutralizing chemicals to aid in decontamination. The waste container can have a vent that has a neutralizing filter to release the build up of pressured vapors.

Turning again to the figures, it will be shown in greater detail how the sets of reaction components 104 (and others described herein) operate.

As explained above, an exemplary operation sequence of the reagent pack 106 with the sets of reaction components 104 is generally shown in FIGS. 7-22B.

The microscope slide 140 is loaded onto the heating element 136 of the slide support element 114 and positioned by location clips 138 or guide pegs or other orientation elements to verify proper location of the microscope slide 140 on the slide support element 114. The slide support element 114 and microscope slide 140 is then moved into the reaction compartment 112 wherein it is sealed via the O-rings 144 and 145 (or other sealing means contemplated herein). The reagent pack 106 is placed onto the reagent pack support device 116. The protocol is entered either automatically or manually (described elsewhere herein) and the apparatus or staining apparatus 100 with the plurality of reaction components 104 is instructed to start. Depending on the protocol the heating element 136 can start to heat the microscope slide 140 or the protocol instructs the dispensing of a reagent from the reagent pack 106 or from another source (e.g., a remote bulk source or X-Y-Z positioning device as discussed elsewhere herein) via the dispensing plunger 154.

If an individual reagent container 107 located on the reagent pack 106 is selected, that particular reagent container 107 will be positioned over the injector port orifice 124 (over the microscope slide 140 outside of the reaction compartment 112), and the dispensing plunger 154 and depresses the piston within the reagent container 107 to expel the reagent 38 therefrom onto the microscope slide 140. The reagent pack 106 would then be moved to position the rinse port aperture 108 in the reagent pack 106 (e.g., generally located between adjacent reagent containers 107) over the injector port orifice 124 wherein the dispensing plunger 154 would be lowered to seal the injector port orifice 124 or, additional air or reagent could be injected into the reaction compartment 112. Once the reagent 158 which has been applied to the microscope slide 140 is removed from the microscope slide 140 by tilting the microscope slide 140 or by rinsing, the microscope slide 140 can be further rinsed with a reagent or treated with pressurized air from the dispensing plunger 154.

As discussed elsewhere herein, the reaction compartments of the present invention can be pressurized (positively or negatively) during heating of the reaction compartment or can be pressurized without heating, or pre-pressurized (positively or negatively) before the microscope slide or other reaction component is heated. The reaction compartment can be pre-pressurized, then heated, then repressurized to maintain a preferred pressure level within the reaction compartment. The reaction compartment can be pressurized either by vapor, gas, or steam produced by a reagent, solution, or liquid within the reaction compartment or by air, steam, inert gases, $N_2$ or any other gas typically used for pressurizing vessels, which is provided from an external source and is supplied via air/pressure ducts or conduits or vacuum lines into the reaction compartment, or by any other method described herein, such as by in situ pressurization.

Embodiments of FIGS. 23-28

Figure 23:
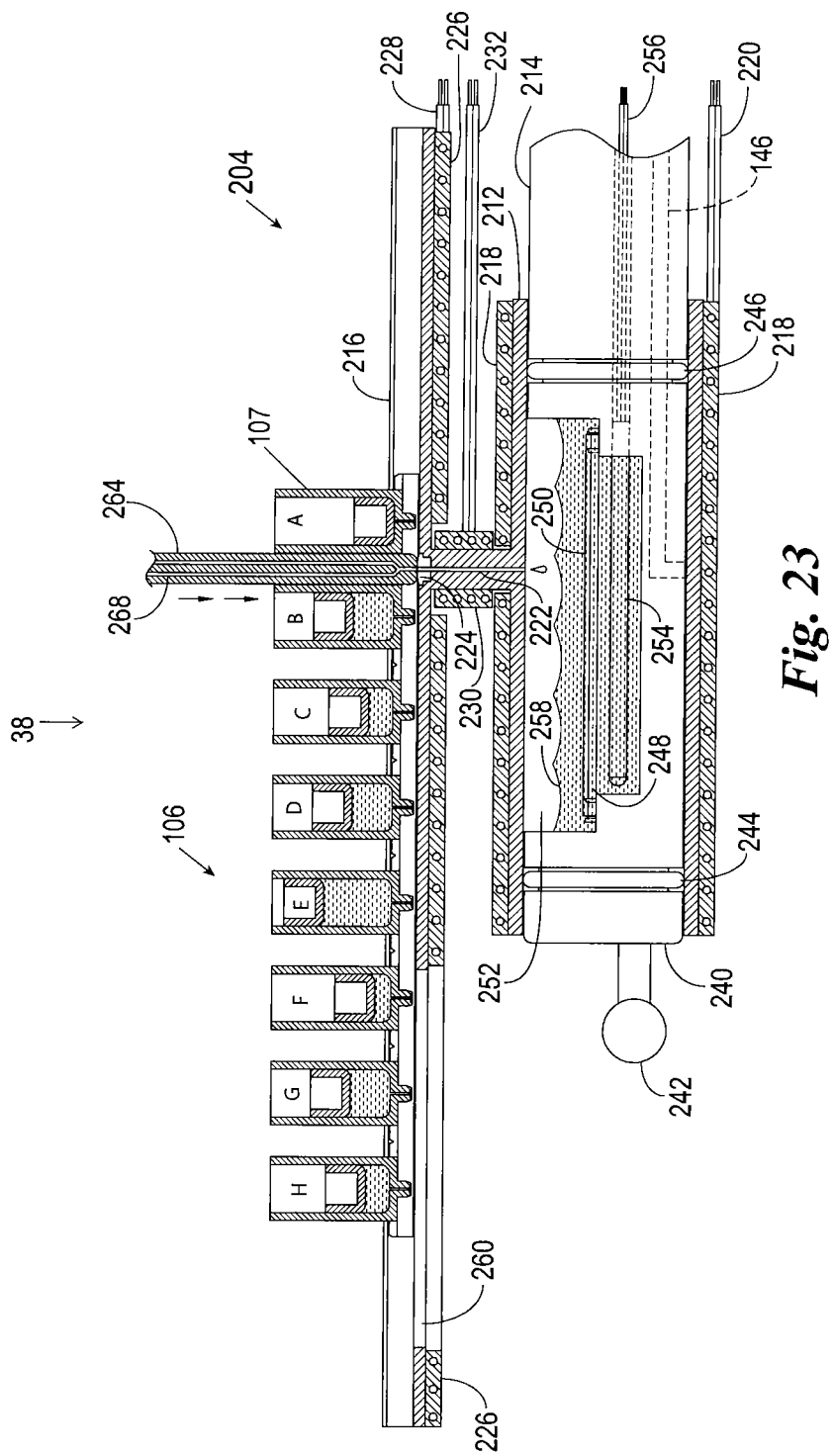
FIG. 23 is a cross-sectional side view of an alternate embodiment of the reaction components, particularly the slide support element, of the present invention.
Figure 24:
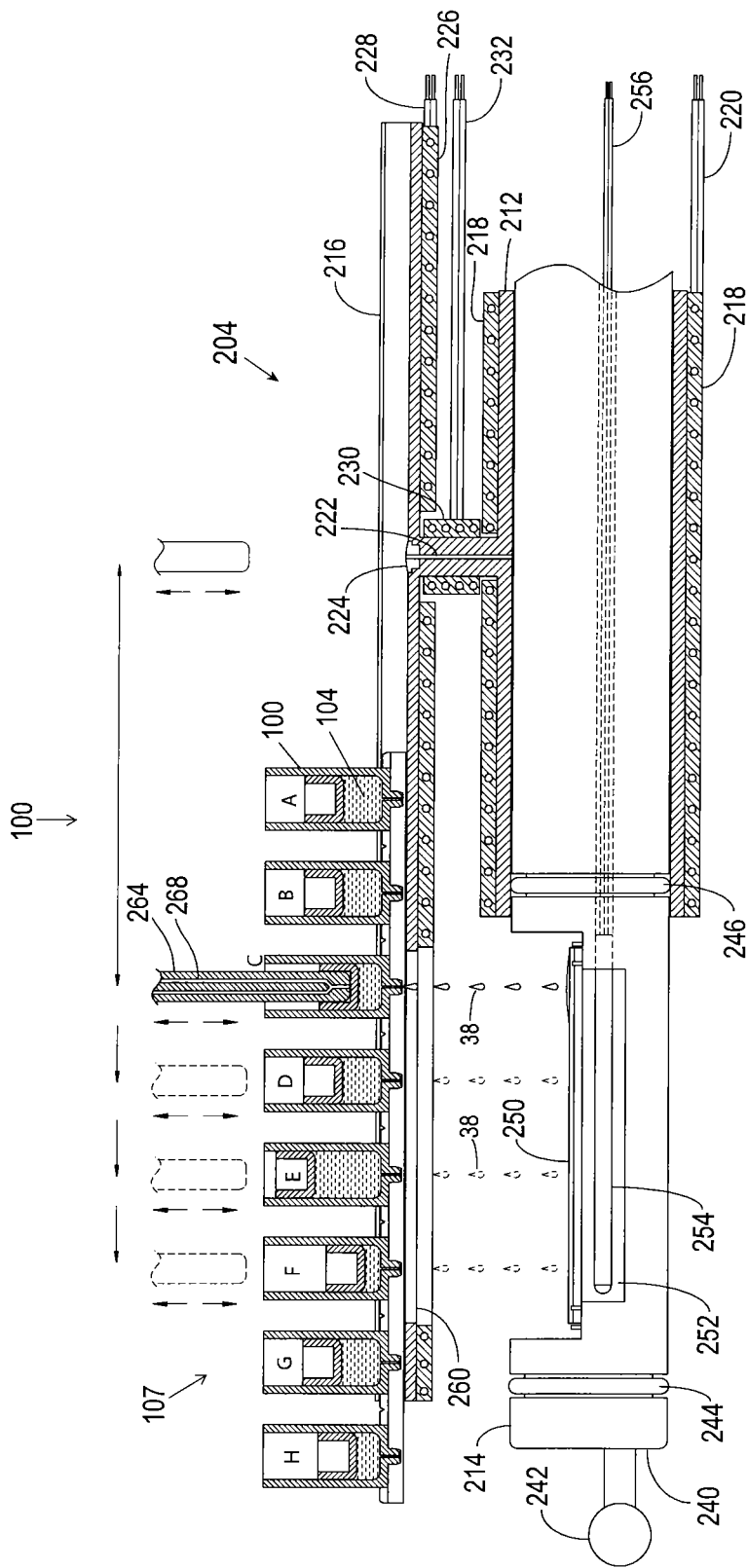
FIG. 24 is a cross-sectional side view of the reaction components of FIG. 23 in an alternate processing configuration wherein a reagent of the reagent pack is applied to the microscope slide outside of the reaction compartment.
Figure 25:
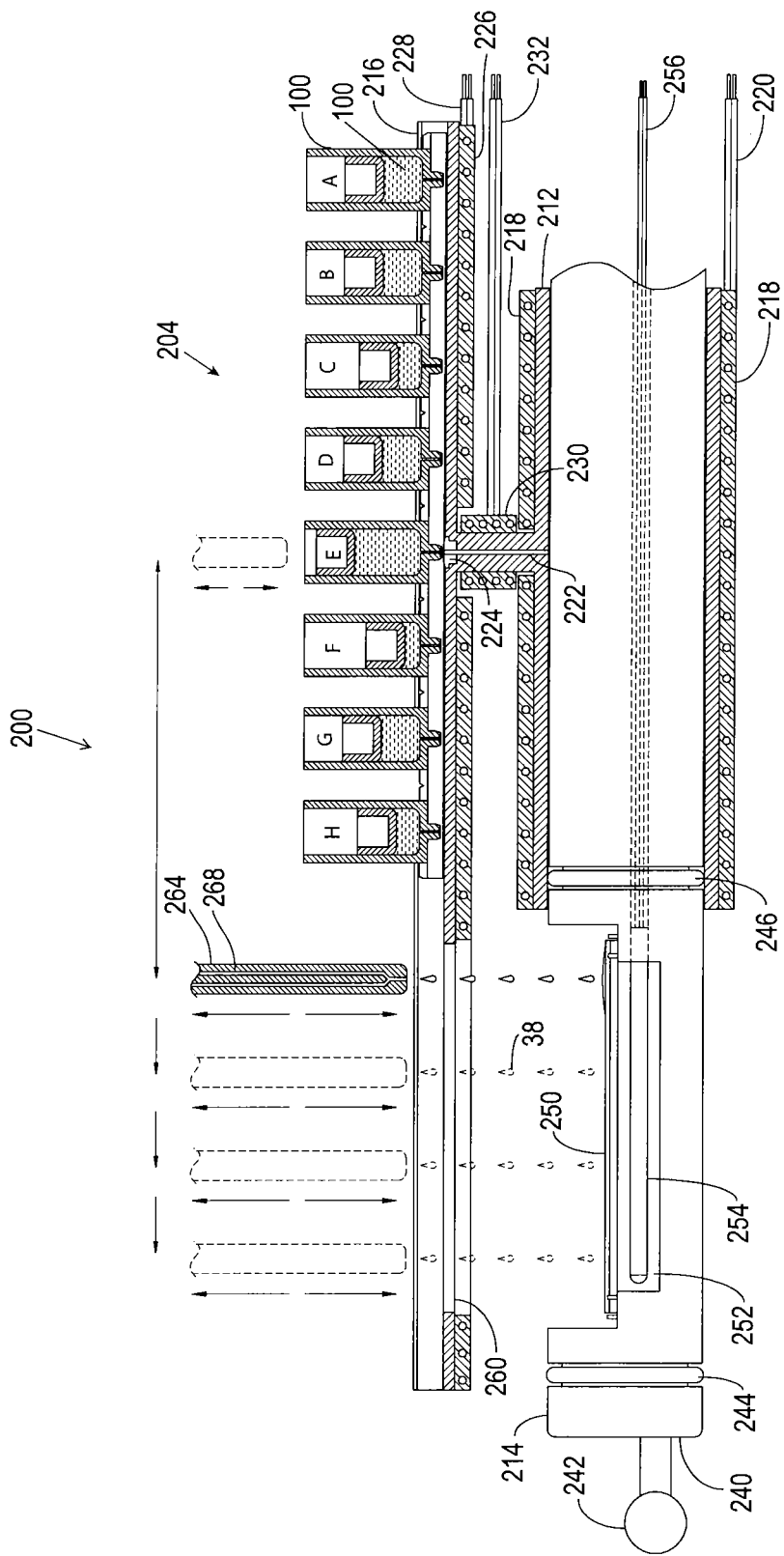
FIG. 25 is a cross-sectional side view of the reaction components of FIG. 23 in another alternate processing configuration wherein a reagent from a remote source is applied to the microscope slide outside of the reaction compartment.
Figure 26:
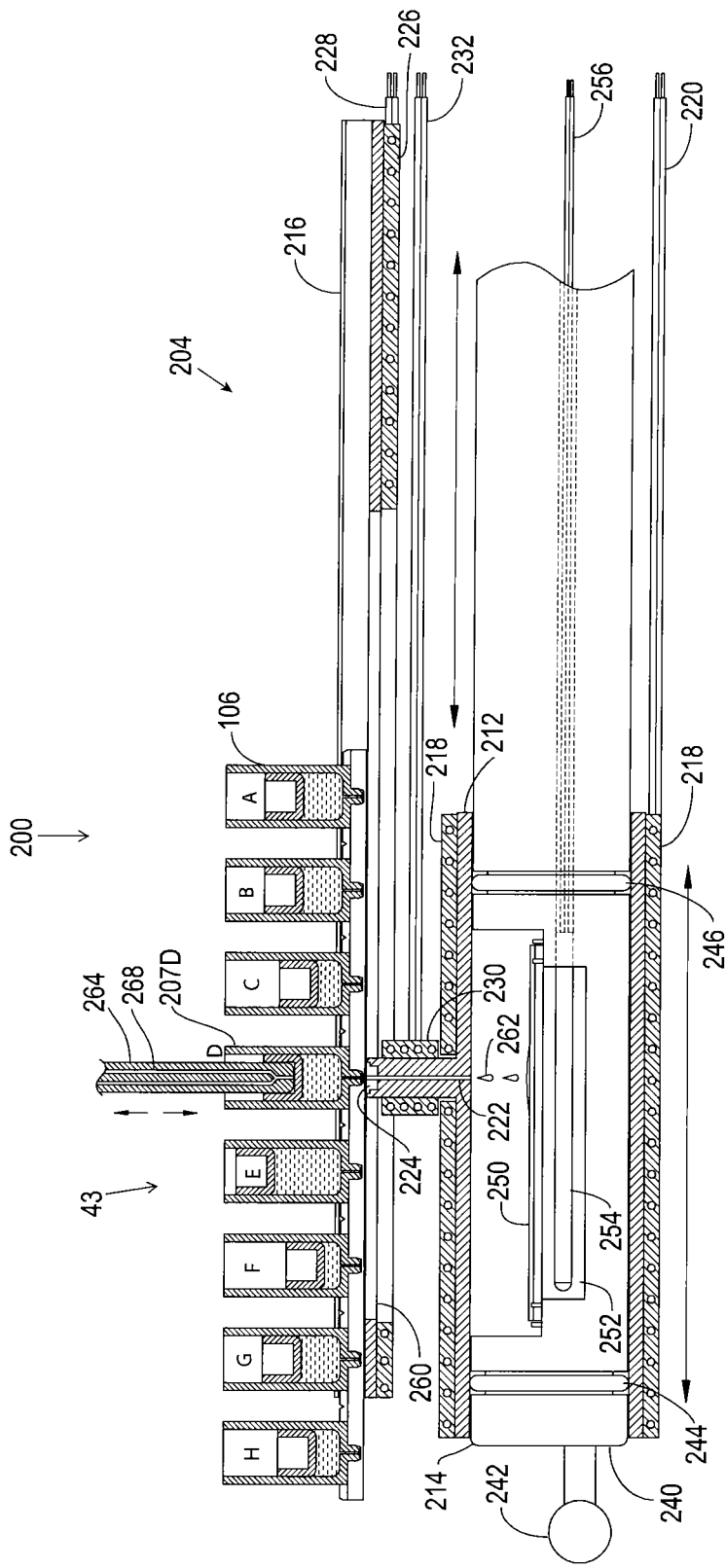
FIG. 26 is a cross-sectional side view of the reaction components of FIG. 23 in an alternate processing configuration.
Figure 27:
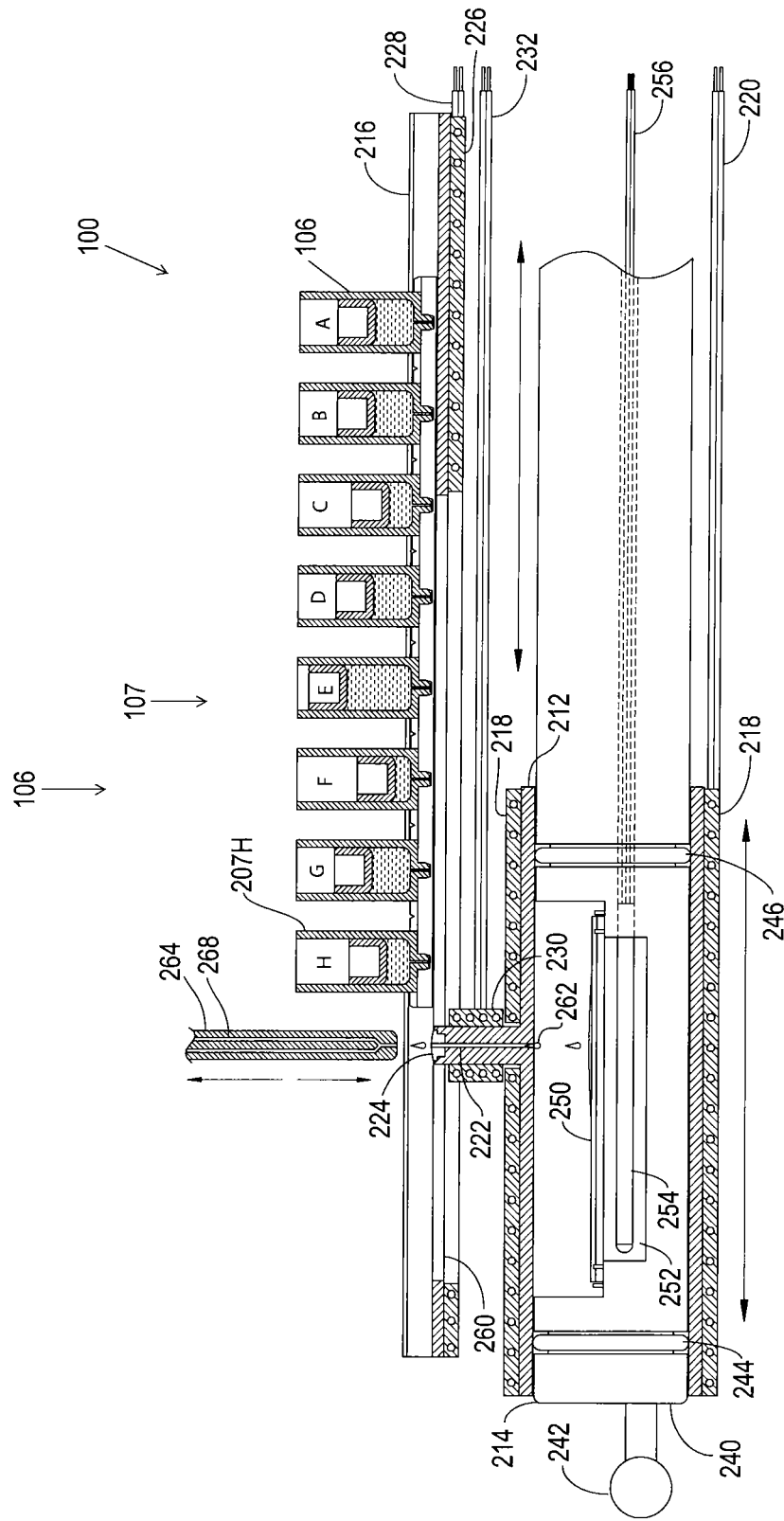
FIG. 27 is a cross-sectional side view of the reaction components of FIG. 23 in an alternate processing configuration.
Figure 28:
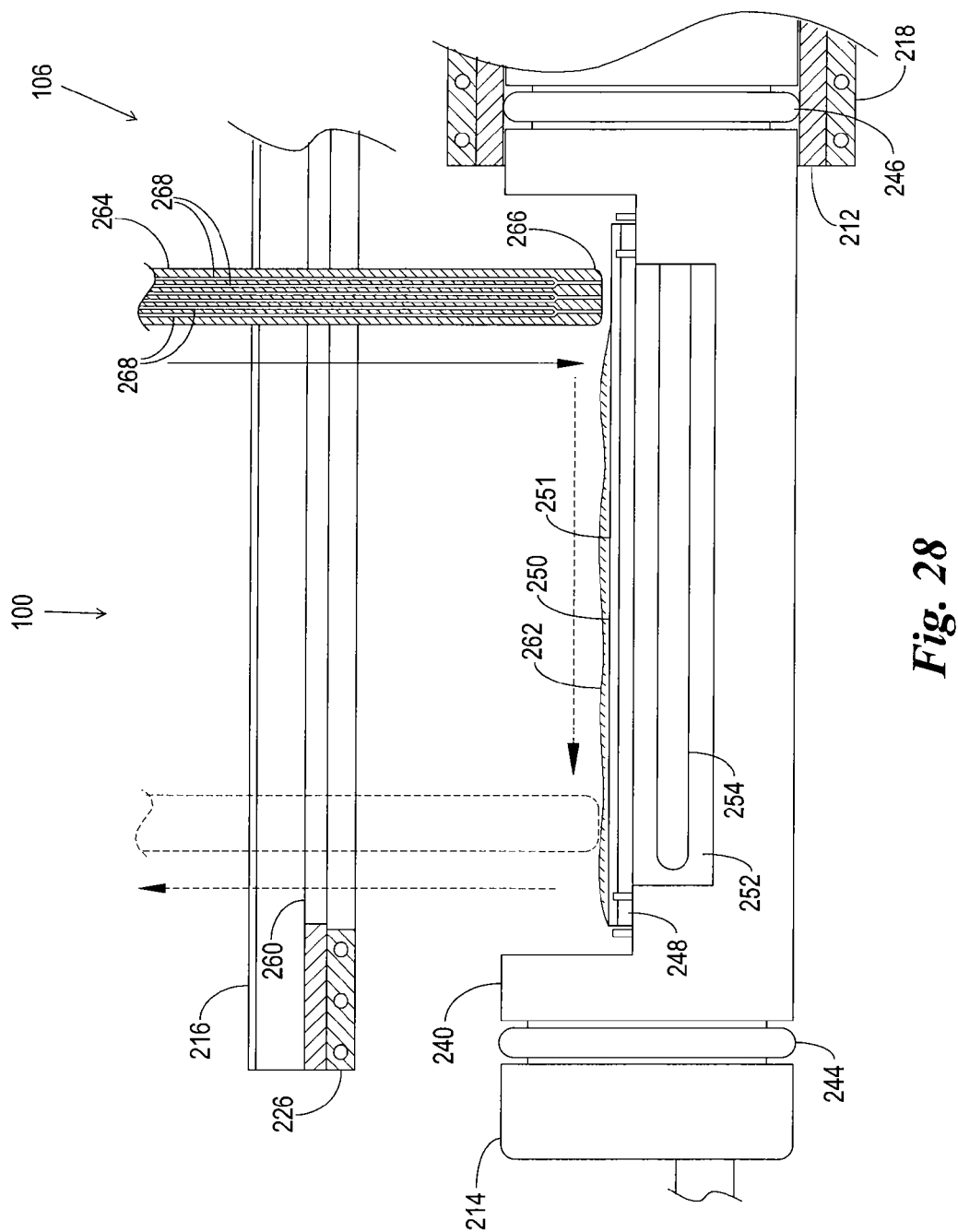
FIG. 28 is an enlarged fragmented cross-sectional side view of the reaction components of FIG. 23 in an alternate processing configuration.

As shown in FIGS. 23-28 in an alternate version of the present invention, a staining apparatus 200 having a front wall 202 (shown in phantom) contains reaction components 204 are similar to reaction components 104 in comprising a reaction compartment 212 similar to reaction compartment 112, a slide support element 214 similar to slide support element 114, and a reagent pack support device 216 similar to reagent pack support device 116. Reaction compartment 212 comprises a reaction compartment heater 218 for heating the reaction compartment 212 and optionally the slide support element 214 when disposed therein or other gases or liquids therein. The reaction compartment heater 218 has leads 220 thereto for connecting to an electric power source (not shown). The reaction compartment 212 further comprises a reagent conduit 222 and an injector port orifice 224 for delivering a reagent or other solution into the reaction compartment 212. The reaction components 204 further comprise a reagent strip heater 226 incorporated into the reagent pack support device 216 for heating a reagent pack 206 (such as any of the reagent packs disclosed herein) disposed thereon. Leads 228 connect the reagent strip heater 226 to an electric power source (not shown). The reaction compartment 212 further comprises a reagent conduit heater 230 for heating the reagent conduit 222 thereby functioning to heat a reagent as it passes through the reagent conduit 222 into the reaction compartment 212 or merely onto a microscope slide 250 if the reagent is applied when the microscope slide 250 is outside of the reaction compartment 212. Leads 232 connect the reagent conduit heater 230 to an electric power source (not shown). The slide support element 214 comprises a base 240 and, a handle 242, and a front O-ring 244 and a rear O-ring 246 for sealing the base 240 and microscope slide 250 within the reaction compartment 212. The slide support element 214 further comprises a microscope slide platform/heater 248 and in operation has the microscope slide 250 disposed thereon, the microscope slide 250 having an upper surface 251. The base 240 further comprises a base cavity 252 positioned below the slide platform/heater 248 and has a base cavity heater 254 positioned therein and connected via lead 256 to an electric power source (not shown). The base cavity heater 254 functions to heat a reagent 258 disposed within the base cavity 252 to a temperature sufficient to heat the microscope slide 250 and biological specimen and reagent 258 disposed thereon as described elsewhere herein for other embodiments of the invention. The reagent 258 in one preferred embodiment completely immerses the microscope slide 250 as shown in FIG. 23. The reagent pack support device 216 in this embodiment comprises a slot 260 (which may also be included in the reagent pack support device 116) therein for enabling a dispenser plunger (i.e., dispenser element) 264 to deliver a reagent 262 directly upon the microscope slide 250 either when it is positioned within the reaction compartment 212 (FIGS. 23, 26, 27) or outside of the reaction compartment (FIGS. 24, 25). As shown in FIGS. 24, 25, and 28 reagents may be applied to or removed from the microscope slide 250 when the microscope 250 slide is positioned outside of the reaction compartment 212 on the slide support element 214 and potentially outside of the staining apparatus 200. Reagent may be removed from the microscope slide 250 by the dispenser plunger 264 by moving the tip 266 of the dispenser plunger 264 over the microscope slide 250 and aspirating the reagent therefrom. Reagent may be delivered to or removed from the microscope slide 250 through one or more conduits 268 in the dispenser plunger 264 (FIG. 28). The conduits 268 may function to provide reagents or solutions, to remove reagents (via aspiration for example), or may provide air, gases, or liquids under pressure.

In other embodiments, reaction components 204 of the present invention may have any one or any combination of slide heating elements 136 or 248, reaction compartment heater 218, reagent strip heater 226, reagent conduit heater 230, and base cavity heater 254, and when present any of the heating systems described herein may function individually and independently of one another. The slide support element 214 may further optionally comprise one or more drainage and/or supply conduits which lead to the base cavity 252 for supplying the base cavity 252 with a liquid or other solution and for draining used liquid from the base cavity 252 after its use (e.g., by aspiration). Other supply ports, conduits, and ducts may supply the reaction compartments of the present invention such as are described in U.S. Pat. Nos. 6,534,008 and 6,855,292.

In a preferred embodiment, the reaction compartment and/or slide support element of the present invention may be exposed to sterilization conditions which may include high heat (e.g., above 100° C., or more preferably above 130° C., and may use steam and/or chemicals to remove, or denature pathogens or residual chemicals or materials such as nucleic acids, antibodies, toxins or other proteins which remain in the reaction compartment and slide support element after the reaction components are used. In a preferred embodiment, the reaction compartment and/or slide support element after heating is quickly cooled to near room temperature or to below 50° C. within 3 sec, 5 sec, 10 sec or 20 sec for example to further denature or inactivate residual proteins or substances.

Further, although the various reaction components are shown herein as components in discrete embodiments, it is contemplated that various components described herein can be assembled in any combination which functions in accordance with the present invention.

Embodiments of FIGS. 29A-29F

Shown in FIGS. 29A-29F is a staining apparatus 300 which is at least one of one or more of such chambers of a microscope slide staining apparatus of the present invention. The staining apparatus 300 has an inner space 302, a front wall 304, a slide support element 310 having a heating element 312, and an optional handle 314, a reaction compartment 316, such as other reaction compartments described herein, a reagent pack support device 318, a reagent plunger 319, and a reagent dispenser 320 each of which is movable upwardly and downwardly in direction 321 and which may be movable laterally as well. When the slide support element 310 is inserted into the inner space 302, an end portion of the slide support element 310 is preferably aligned flush with an outer surface of the front wall 304 as shown in FIGS. 29B-29E.

Figures 29E, 29F:
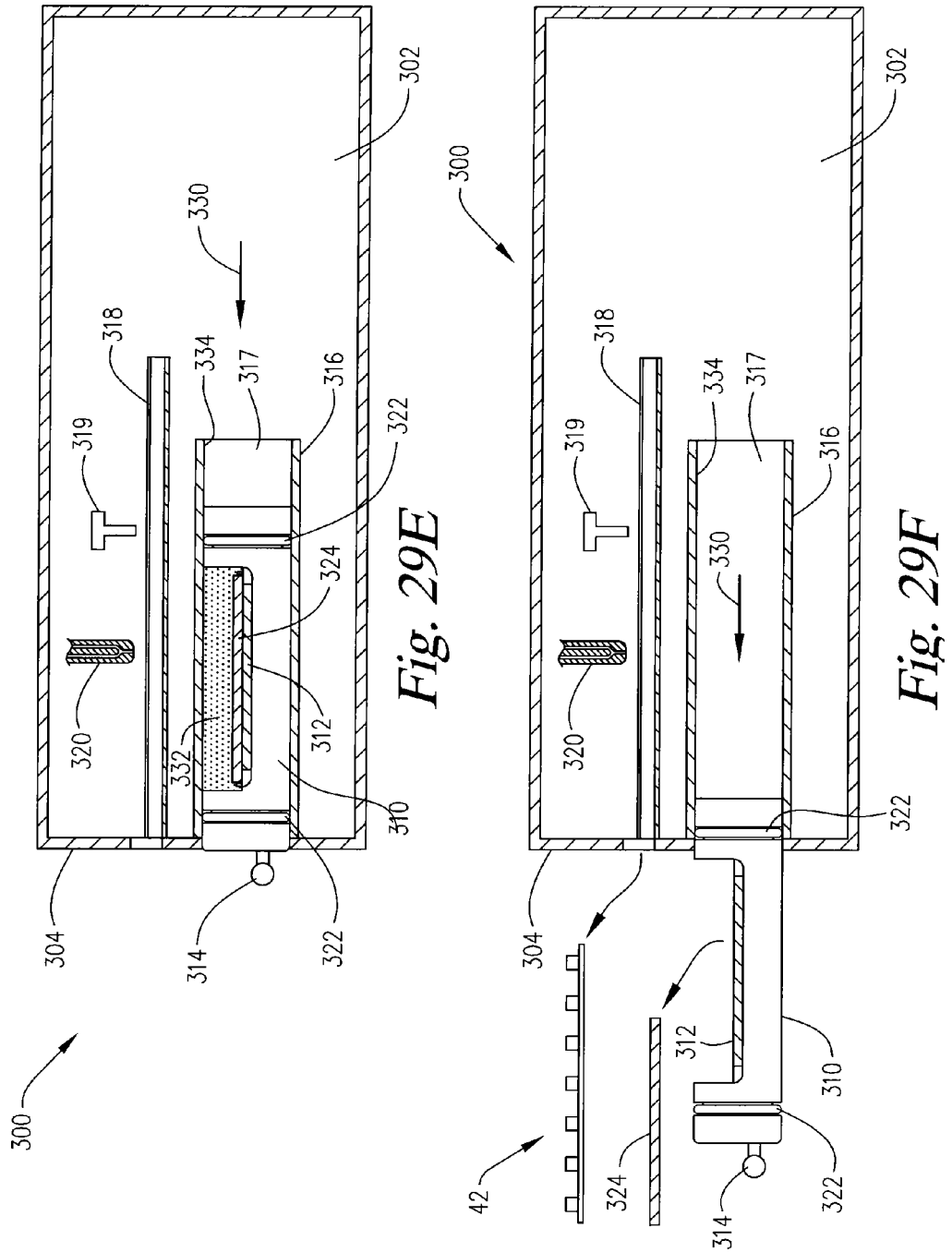

The slide support element 310 is similar to other slide support elements described herein and has sealing means 322 such as described elsewhere herein for enabling a microscope slide 324 to be sealingly enclosed on the slide support element 310 within the reaction compartment 316. A reagent pack 42 (such as any reagent pack contemplated herein) can be inserted through an opening in the front wall 304 into the inner space 302 of the staining apparatus 300 where it is secured on the reagent pack support device 318 for dispensing a reagent 328 onto the microscope slide 324 via the reagent plunger 319 or by reagent dispenser 320 in a manner similar to that described for other such dispensers and plungers discussed elsewhere herein (in an alternate embodiment, the reagent pack support device 318 (or any support devices contemplated herein) may be ejected through an opening in the front wall 304 such that the reagent pack 42 can be loaded outside thereof of the staining apparatus 300. Shown in FIG. 29A the microscope slide 324 is initially in a placement position outside of the reaction compartment 316 and inner space 302 of the staining apparatus 300. A microscope slide 324 is positioned on the heating element 312 of the slide support element 310 which is retracted in direction 326 into the reaction compartment 316 (FIG. 29B). A reagent 328 is delivered to the microscope slide 324 via the reagent plunger 319 (from the reagent pack 42) on the reagent pack support device 318 or from a remote reagent source via reagent dispenser 320 after the reaction compartment 316 has been retracted from the slide support element 310 in direction 326 (FIG. 29C). After the reagent 328 has been applied to the microscope slide 324, the reaction compartment 316 is moved in direction 330 back over the slide support element 310 wherein the sealing means 322 causes the slide support element 310 to be sealed against the inner surface 334 of the reaction compartment 316 so the microscope slide 324 is sealed therein (FIG. 29D) within a pressurizable treatment space 332 within the reaction compartment 316. The pressurizable treatment space 332 is then pressurized via pressurizing means as described elsewhere herein (FIG. 29E). The microscope slide 324 is heated by the heating element 312 to a predetermined temperature which causes the reagent 328 on the microscope slide 324 to be heated to an elevated temperature above that which could be obtained absent the elevated pressure of the pressurizable treatment space 332. The heated reagent 328 causes the desired biochemical/physical reaction within the biological sample on the microscope slide 324 within the pressurizable treatment space 332. After the reaction is completed, the pressure level within the pressurizable treatment space 332 of the reaction compartment 316 is returned to a normal (pre-pressurization) level and the reagent 328 is removed therefrom by means such as those discussed elsewhere herein. The slide support element 310 is then ejected from the reaction compartment 316 and/or inner space 302 of the staining apparatus 300 via direction 330 wherein the microscope slide 324 can be removed therefrom (FIG. 29F). This can occur immediately after the heating step, or after one or more additional steps or procedures has been performed on the microscope slide 324. For example the steps of FIGS. 29B-29D (and optionally FIG. 29E) can occur several times before the microscope slide 324 is removed in the step of FIG. 29F.

Embodiments of FIGS. 30A-30F

Shown in FIGS. 30A-30F is a staining apparatus 340 which is at least one of one or more of such chambers of a microscope slide staining apparatus of the present invention. The staining apparatus 340 has an inner space 342, a front wall 344, a slide support element door 346 (shown open), a reagent pack door 348, a slide support element 350 having a heating element 352, an optional handle 354, a reaction compartment 356, such as other reaction compartments described herein except having a closed end 364, a reagent pack support device 366, and a reagent dispenser plunger 368.

Reaction compartment 356 further comprises an inner space 362, a pressure equalization conduit 358 between a forward portion of the inner space 362 and a rear portion of the inner space 362 and a rear portion of the inner space 362. A conduit valve 360 is present in the pressure equalization conduit 358 for opening and closing the conduit 358 when desired or for preventing backflow.

The slide support element 350 is similar to other slide support elements described herein such as shown in FIGS. 29A-29F, and has sealing means 370 such as described elsewhere herein for enabling a microscope slide 324 to be sealingly enclosed within the reaction compartment 356. A reagent pack 42 can be inserted through the opened reagent pack door 348 into the inner space 342 of the staining apparatus 340 where it is secured on the reagent pack support device 366 for dispensing a reagent 328 onto the microscope slide 324 via the reagent plunger 367 or via a reagent dispenser 368 in a manner similar to that described for other such dispensers or plungers discussed elsewhere herein. In this embodiment, the microscope slide 324 is initially in a placement position outside of the reaction compartment 356 and the inner space 342 of staining apparatus 340. A microscope slide 324 is positioned on the heating element 352 of the slide support element 350 which is retracted in direction 372 into the reaction compartment 356 (FIG. 30B). A reagent 328 is delivered to the microscope slide 324 from the reagent plunger 367 (from the reagent pack 42) on the reagent pack support device 366 or from a remote reagent source via reagent dispenser 368 after the reaction compartment 356 has been retracted from the slide support element 350 in direction 372 (FIG. 30C). After the reagent 328 has been applied to the microscope slide 324, the reaction compartment 356 is moved in direction 376 back over the slide support element 350 wherein the sealing means 370 causes the slide support element 350 to be sealed against the inner surface 357 of the reaction compartment 356 so the microscope slide 324 is sealed therein within a pressurizable treatment space 378 within the reaction compartment 356. The pressurizable treatment space 378 (also referred to herein a pressurization treatment space 378) is then pressurized (FIG. 30D) via "in situ pressurization" as explained below.

The microscope slide 324 is heated by the heating element 352 to a predetermined temperature which causes the reagent 328 on the microscope slide 324 to be heated to an elevated temperature above that which could be obtained absent the elevated pressure in the pressurizable treatment space 378. The heated reagent 328 causes the desired biochemical/physical reaction within the biological sample on the microscope slide 324 within the pressurizable treatment space 378. After the reaction is completed, the pressure level within the pressurizable treatment space 378 and head space 380 of the reaction compartment 356 is returned to normal and the reagent 328 is removed therefrom by means such as those discussed elsewhere herein. The slide support element 350 is then ejected from the reaction compartment 356 and/or inner space 342 of the staining apparatus 340 via direction 384 wherein the microscope slide 324 can be removed therefrom (FIG. 30F). This can occur immediately after the heating step, or after one or more additional steps or procedures has been performed on the microscope slide 324. For example the steps of FIGS. 30B-30E can occur several times before the microscope slide 324 is removed in the step of FIG. 30F.

In a preferred embodiment of the reaction compartment 356 (and of other reaction compartments contemplated herein), the sealing means 370 comprises a ground or polished glass seal in a surface portion of the reaction compartment 356 which can hold pressure from a separate bulk source of pressure to pressurize the pressurization space 378 of the reaction compartment 356 or, in an alternative embodiment this polished seal (or other seals described herein) can also produce and hold pressure inside the pressurization space 378 of the reaction compartment 356 without the need for a separate bulk pressure source being sent to each reaction compartment 356.

This method of pressure generation, operationally represented in FIG. 30E, is referred to herein as "in-situ pressurization". The very effective sealing means 370 of the present invention can form a pressurization treatment space which is sufficiently sealed to produce and/or increase and/or decrease the pressure of atmospheric pressure conditions inside the pressurization treatment space 378 of the reaction compartment 356. After the slide support element 350 and slide thereon is sealed within the reaction compartment 356 the slide support element 350 is moved further into the inner space 362 of the reaction compartment 356 to produce pressure therein by forcing the trapped residual atmospheric air in the pressurization space 378 surrounding the microscope slide 324 in the reaction compartment 356 and inside a head space 380 of the reaction compartment 356. For example, in one embodiment the reaction compartment 356 (e.g., having a length of 8 inches can have the slide support element 350 inside the first 5 inches of its length. The head space 380 comprises the remaining 3 inches of space within the reaction compartment 356. The reagent 328 has been added to the microscope slide 324 present on the slide support element 350. The slide support element 350 is then moved farther into the head space 380 of the reaction compartment 356, for example 0.01 to nearly 3 inches. This movement, further into the reaction compartment 356 causes the gas (e.g., air) in the head space 380 between the closed end 364 of the reaction compartment 356 and a distal end 351 of the slide support element 350 to compress. This compression of the air in the head space 380 produces pressure above the original pressure in the reaction compartment 356. This pressure is diverted to the pressurization treatment space 378 by conduit 358 through valve 360. The head space 380 is only in contact with the pressurization treatment space 378 about the microscope slide 324, and vice versa, by the conduit 358 or other means to connect the head space 380 with the pressurization treatment space 378.

This connection with the head space 380 to the pressurization treatment space 378 may include as noted a one-way or two-way conduit valve 360 or other means of transferring the pressure in the compressed head space 380 to the pressurization treatment space 378 without allowing the contents of the pressurization treatment space 378 to be communicated or moved toward or into the head space 380 for possible contamination of the head space 380 or vice versa.

The pressurization conduit 350 is shown in FIGS. 30A-30F as a conduit between proximal and distal portions of the reaction compartment 356, however the conduit may instead be wholly within a distal portion of the slide support element 350 (e.g., see FIGS. 33A-33H).

Although the pressured gas or air produced from the compressed head space 380 can move into the pressurization treatment space 378 there is a need to stop any contamination of the gas or air in the compressed head space 380 with the contents of the pressurization treatment space 378 and vice versa. Valves or other systems known in the art can be used to inhibit or stop this potential backflow and/or cross-contamination. These conduit valves 360 can be, but are not limited to, in line water or gas dedicators, one-way valves, two-way valves, a one way pressure opening valves, metered ports, or any other device able to be used to prevent the contents from one compartment or area being contaminated with the contents of another compartment or area.

The amount of pressure in the pressurization treatment space 378 is proportional to the degree of movement of the slide support element 350 into the head space 380 of the reaction compartment 356. The pressure produced is directly related to the length and outer diameter of the slice support element 350 and the length and inner diameter of the reaction compartment 356 along with the total travel length of the slide support element 350 or the reaction compartment 356 with the movement to compress the head space 380 with a normal atmospheric pressure trap between the front of the reaction compartment 356 and the closed end 364 of the reaction compartment 356 to produce the increased pressure by compressing the air or gas trapped in the head space 380. The pressure in the head space 380 for example could be 20 psig caused by compressing the residual air trapped in the head space 380 and the now pressurized air could be delivered via the conduit 358 to the pressurized treatment space 378 containing the microscope slide thereby equilibrating the pressure of the pressurized head space with the pressure in the pressurized treatment space 378. Evaporation of reagents associated with the biological specimen, under heat could also contribute to the pressure in the pressurized treatment space 378. As noted above, a conduit valve 360 can be present for preventing contents of the pressurization treatment space 378 from moving into the head space 380 through the conduit 358. The pressure in the head space 380 can be increased or decreased before, during, or after the heating element 352 heats the reagent 328 in contact with the microscope slide 324. Since the reaction compartment 356 may have a heating device in its walls, in one embodiment of the invention, a liquid could also be added to the head space 380 to produce steam or gas to be sent through the conduit 358 to pressurize the pressurization treatment space 378 of the slide support element 350.

In summary, the head space 380 can be used to cause pressurization of the pressurization treatment space 378 (above or below atmospheric pressure) before, during, or after the heating elements 352 are turned on without having an external source of pressure used to pressurize the pressurization treatment space 378. Further, the presently described in situ pressurization of the pressurization treatment space 378 can occur without use of heat from heating elements. Alternatively, as noted, liquid could be added to the head space 380 to induce pressurization by steam or vapors or add further pressure to the pressurization treatment space 378 in the reaction compartment 356 whether the head space 380 is compressed or not. This apparatus could also be able to draw a vacuum into the pressurization treatment space 378, for example by reversing the movement of the slide support element 350 and pulling the reaction compartment 356, the slide support element 350, or both, in opposite directions to produce a vacuum in the conduit 358 and thereby placing the vacuum in both the head space 380 and pressurization treatment space 378. This method can also be used to regulate the pressure inside the pressurization treatment space 378 regardless of the source of the pressure by moving the reaction compartment 358 and slide support element 350 together or separately to cause a pressure or vacuum environment to regulate the pressure or vacuum conditions within the reaction compartment 356. In one example, if the pressure is desired to be maintained at 30 psig in the pressurization treatment space 378, the regulation can come from the pressurized or depressurized head space 380. This regulation is available no matter how the pressure was or is originally being maintained. For example, if the microprocessor senses the pressure in the pressurization treatment space 378 exceeds the desired temperature or is too low, the position of the slide support element 350 or reaction compartment 356 could be adjusted slightly to change the pressure level. Or the microprocessor could use this head space pressure regulation process to quickly reduce or add pressure to the pressurization treatment space 378 for a condition that might become dangerous to the limits of the strength and integrity of the reaction compartment 356 as a failsafe option. The change in pressure in the head space 380 can be a fine adjustment or coarse adjustment to the pressure in the pressurization treatment space 378. The adjustment increments can be of any measurable amount. The adjustment can be as little as 0.001 psig above or below atmospheric pressure. Preferably the adjustment is in 0.5 psig increments either above or below atmospheric pressure.

In this embodiment of the present invention, as noted "in-situ" pressurization and vacuum (above atmospheric or below atmospheric pressure) is caused by compressing the head space 380 in the portion of the reaction compartment 356 between the closed end 364 thereof and the distal end 351 of the slide support element 350. An individual reaction compartment 356 can move in relation to the slide support element 350 or the slide support element 350 can move in relation to the corresponding individual reaction compartment 356. The individual reaction compartment 356 and the slide support element 350 can move independently of each other and/or simultaneously with each other to compress the head space 380 present between the individual reaction compartment 356 and the distal end 351 of the slide support element 350. In the preferred embodiment of the "in-situ" production of pressure described herein, in which a single individual reaction compartment 356 is sealed about a single slide support element 350, both are independently movable in relation to each other under pressure and wherein pressure is produced by the relative movement of each other and the sealed head space 380 in relation to the sealed individual reaction compartment 356 and the single slide support element 350. As noted previously, the reaction compartment 356 can be modified to hold more than one microscope slide per slide support element (e.g., 2 or more) if desired and still be able to produce "in-situ pressurization". A reaction compartment 356 could be sized to hold multiple slide support elements 350 moving on a single platform that can be joined with a reaction compartment 356 which is complementary with the larger slide support platform. In situ pressurization via compression of the headspace 380 of the reaction compartment 356, can be performed without addition of additional pressurization from a remote pressurization means thus reducing the complications inherent in using such a remote source for example the requirement of tubes, valves, and conduits able to tolerate above-atmospheric or below-atmospheric pressures.

Embodiments of FIGS. 31A-31F and 32

Shown in FIGS. 31A-31F and 32 is a staining apparatus 300a which is at least one of one or more of such chambers of a microscope slide staining apparatus of the present invention. The staining apparatus 300a has an inner space 302a, a front wall 304a, a slide support element door 306a (shown open), a reagent pack door 308a, a slide support element 310a having a heating element 312a, an optional handle 314a, a reaction compartment 316a, a reagent pack support device 318a, a reagent plunger device 319a and a reagent dispenser 320a.

The staining apparatus 300a is substantially the same as staining apparatus 300 of FIGS. 29A-29F except that the reaction compartment 316a differs from reaction compartment 316 of FIG. 29A in that it has an open portion or "window" 317 through which the reagent 328 can be applied to the microscope slide 324 from or by the reagent plunger 319a or via the reagent dispenser 320a. In this embodiment with "windows", the window 317 is advantageous in enabling the reagent to be dispensed upon the microscope slide 324 without having to be passed through a narrow reagent conduit. Further, a dispenser element associated with the X-Y-Z positioning device (e.g. such as reagent dispenser 320a) does not have to be adapted for use with a reagent pack to be able to be used with the reaction compartment window 317.

The reaction compartment 316a can be rotated about the slide support element 310a to close the window 317 to form a pressurizable treatment space 332a around the microscope slide 324 in the reaction compartment 316a. In this embodiment, preferably, the sealing means 322a is a ground and polished glass surface that can be easily rotated to open and close the window 317. Reaction compartment 316a with window 317 is shown in a perspective view in FIG. 32. The rotational movement in this embodiment of the reaction compartment 316a can be a few degrees or can be 180° or more in relation to the microscope slide 324. Thus, the window 317 of the reaction compartment 316a can be positioned directly above the microscope slide 324 (in a 0° position or "open" position) or can be rotatingly moved through a range of positions to be directly under the microscope slide 324 (180° position or "closed" position), rotating in either direction from the 0° home (open) position to the closed position wherein the window is covered by a lower surface of the slide support element 310a. The sealing means 322a can be of any type known in the art of sealing pressurized vessels. The preferred sealing means 322a is a ground and polished glass seal. This type of seal is known in the art of ground and polished seals for glass hypodermic syringes for example which are manufactured and sold under the trade name Micro-Mate® by Popper and Sons, Inc. New Hyde Park, N.Y., and thus such ground and polished glass seals are known in the art.

Figure 31C:
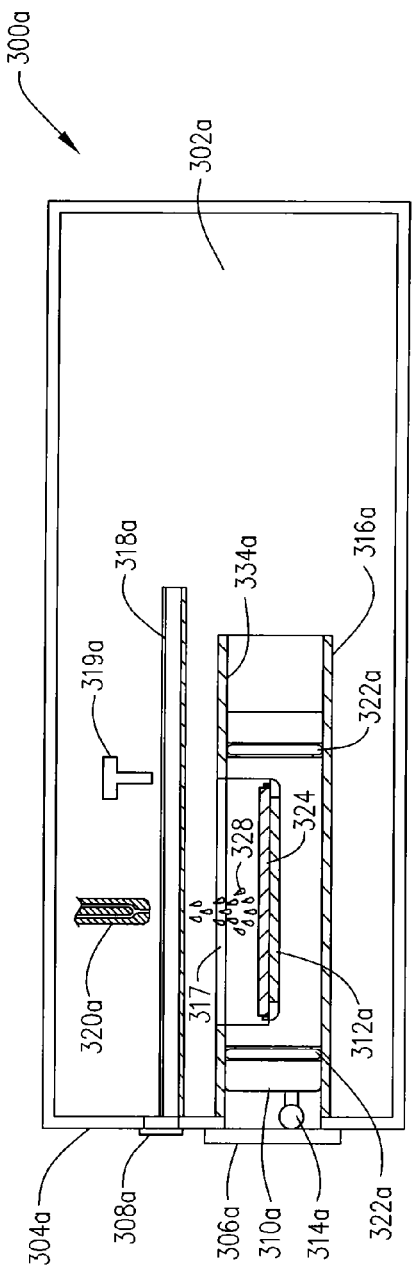
Figure 31D:
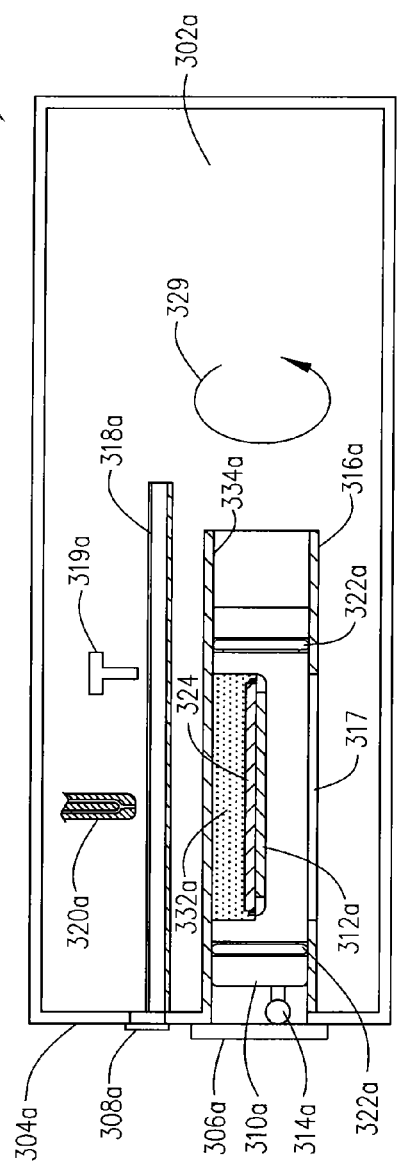
Figure 31E:
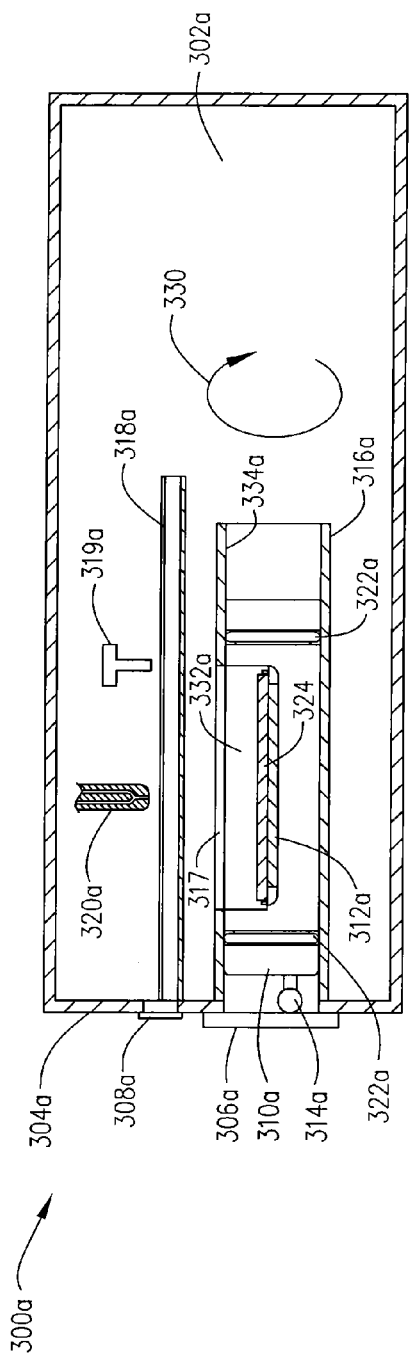

The slide support element 310a is similar to other slide support elements described herein and has sealing means 322a such as described elsewhere herein for enabling the microscope slide 324 to be sealingly enclosed within the reaction compartment 316a. A reagent pack 42 can be inserted through the opened reagent pack door 308a into the inner space 302a of the staining apparatus 300a where it is secured on the reagent pack support device 318a (or otherwise positioned thereon) for dispensing a reagent 328a onto the microscope slide 324 via the reagent plunger 319a or via reagent dispenser 320a in a manner similar to that described for other such dispensers or plungers discussed elsewhere herein except that the reagent 328 is preferably disposed through the window 317 of the reaction compartment 316a. In this embodiment, the microscope slide 324 is initially in a placement position outside of the reaction compartment 316a and inner space 302a of the staining apparatus 300a. The microscope slide 324 is positioned on the heating element 312a of the slide support element 310a which is retracted in direction 326a into the reaction compartment 316a (FIG. 31B). A reagent 328 is delivered to the microscope slide 324 from the reagent plunger 319a (from the reagent pack 42) on the reagent pack support device 318a or from a remote reagent source via reagent dispenser 320a (FIG. 31C). Then the reaction compartment 316a is rotated 180° (or other equally effective amount) about the slide support element 310a in direction 329 (FIG. 31D), thereby closing the window 317 wherein the sealing means 322a causes the slide support element 310a to be sealed against an inner surface 334a of the reaction compartment 316a so the microscope slide 324 is sealed therein within the pressurization treatment space 332a.

Figure 31F:
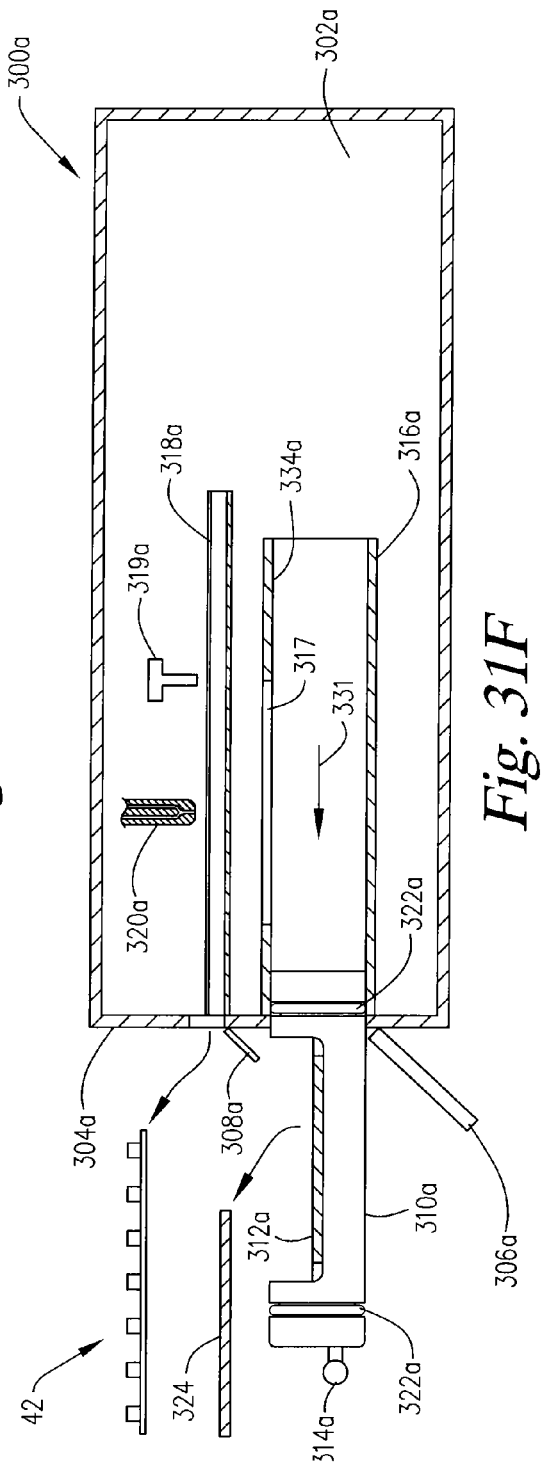
Figure 32:
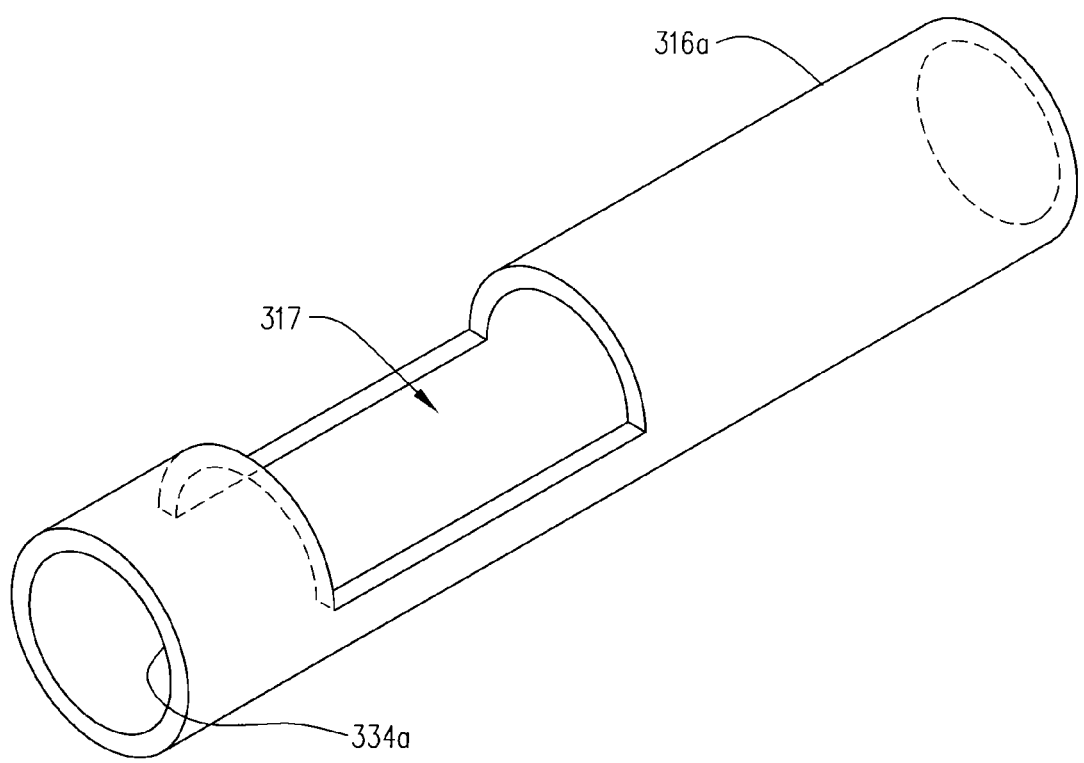
FIG. 32 is a perspective view of a reaction compartment having a window, such as is used in the embodiment of FIGS. 31A-31F.

The pressurization treatment space 332a is then pressurized (FIG. 31D) via pressurizing means as described elsewhere herein. The microscope slide 324 is then heated by the heating element 312a to a predetermined temperature which causes the reagent 328 on the microscope slide 324 to be heated to an elevated temperature above that which could be obtained absent the elevated pressure in the pressurization treatment space 332a. The heated reagent 328 causes the desired biochemical/physical reaction within the biological sample on the microscope slide 324 within the pressurization treatment space 332a. After the reaction is completed, the pressure level within the pressurization treatment space 332a of the reaction compartment 316a is returned to normal, the reaction compartment 316a is rotated to the home (open) position (FIG. 31E), and the reagent 328 is removed therefrom by means such as those discussed elsewhere herein. The slide support element 310a is then ejected from the reaction compartment 316 and/or inner space 302a of the staining apparatus 300a via movement in direction 330 wherein the microscope slide 324 can be removed therefrom (FIG. 31F). This can occur immediately after the heating step, or after one or more additional steps or procedures has been performed on the microscope slide 324. For example the steps of FIGS. 31C-31E can occur several times before the microscope slide 324 is removed in the step of FIG. 31F.

Embodiments of FIGS. 33A-33H

Shown in FIGS. 33A-33H is a staining apparatus 340a which is at least one of one or more of such chambers of a microscope slide staining apparatus. The staining apparatus 340a has an inner space 342a, a front wall 344a, a slide support element door 346a (shown open), a reagent pack door 348a, a slide support element 350a having a heating element 352a, a distal end 351a, an optional handle 354a a reaction compartment 356a, which combines the elements of other reaction compartments described herein such as reaction compartments 316a and 356, a reagent pack support device 366a, a reagent plunger 367a, and a reagent dispenser 368a.

In particular, the reaction compartment 356a has a closed end 364a, and inner surface 357a, an inner space 362a, and a window 365 through which a reagent 328 can be applied in the manner shown in FIGS. 31A-31F. The slide support element 350a comprises a pressure equalization conduit 358a which is similar to the pressure equalization conduit 358 of FIGS. 30A-F in that the conduit 358 allows pressure equalization between a forward portion of the inner space 362a (which constitutes a pressurization treatment space 378a where the microscope slide 324 is positioned) and a rear portion which constitutes a head space 380a of the reaction compartment 356a, but which is different therefrom in that conduit 358a is positioned in a distal portion 351a of slide support element 310a rather than in reaction compartment 356a.

Figure 33C:
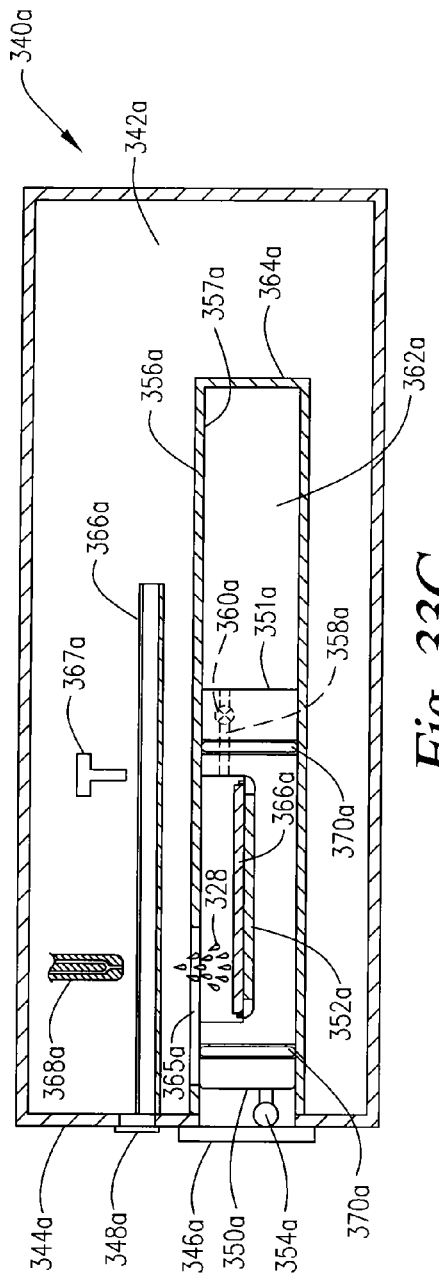
Figure 33D:
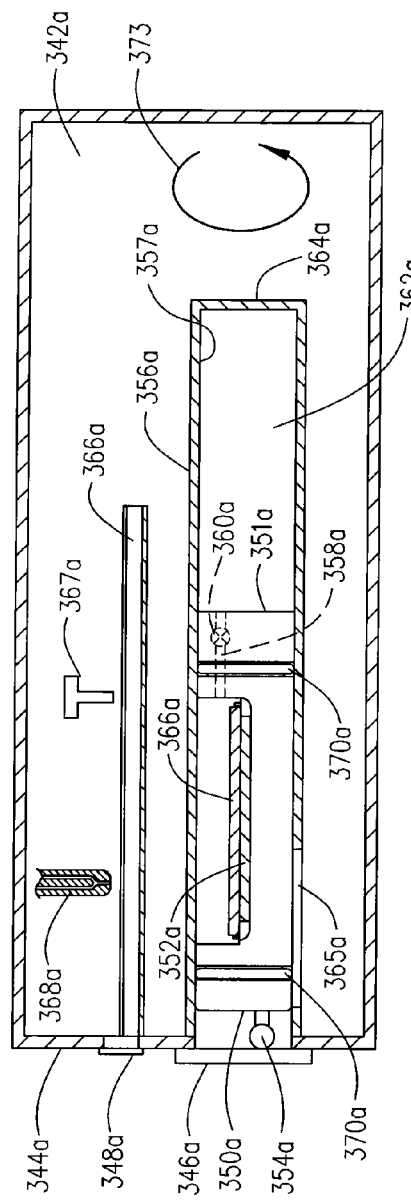

The slide support element 350a is similar to other slide support elements described herein and has sealing means 370a such as described elsewhere herein for enabling a microscope slide 324 to be sealingly enclosed within the reaction compartment 356a. A reagent pack (not shown) can be inserted through the opened reagent pack door 346a into the inner space 342a of the staining apparatus 340a where it is secured on the reagent pack support device 366a for dispensing a reagent 328 onto the microscope slide 324 via the reagent plunger 367a or via reagent dispenser 368a in a manner similar to that described for other such dispensers and plungers discussed elsewhere herein. In this embodiment, the slide support element 350a is initially in a placement position outside of the reaction compartment 356a and staining apparatus inner space 342a (FIG. 33A). A microscope slide 324 is positioned on the heating element 352a of the slide support element 350a which is retracted in direction 372 into the reaction compartment 356a (FIG. 33B). A reagent 328 is delivered through window 365 to the microscope slide 324 from the reagent plunger 367a (from the reagent pack (not shown)) on the reagent pack support device 366a or from a remote reagent source via reagent dispenser 368a after the reaction compartment 356a has been retracted from the slide support element 350a in direction 372 (FIG. 33C). After the reagent 328 has been applied to the microscope slide 324, the reaction compartment 356a is rotated 180° (or other appropriate amount) in direction 373 wherein the sealing means 370a causes the slide support element 350a to be sealed against the inner surface 357a of the reaction compartment 356a in the same manner as in FIG. 31D wherein the microscope slide 324 is sealed therein (FIG. 33D) within a pressurization treatment space 378a. The pressurization treatment space 378a is then pressurized as shown in FIGS. 33E-33F in the same "in situ pressurization" method shown and described in regard to FIGS. 30D-30E. The microscope slide 324 in the pressurization treatment space 378a is heated by the heating element 352a to a predetermined temperature which causes the reagent 328 on the microscope slide 324 to be heated to an elevated temperature above that which could be obtained absent the elevated pressure in the pressurization treatment space 378a. The heated reagent 328 causes the desired biochemical/physical reaction within the biological sample on the microscope slide 324 within the pressurization treatment space 378a (FIG. 33F). After the reaction is completed, the pressure level within the pressurization treatment space 378a of the reaction compartment 356a is returned to normal (FIG. 33G) and the reagent 328 is removed therefrom by means such as those discussed elsewhere herein. Additional reagent can then be applied to the slide through the window 365 if desired. The slide support element 350a is then ejected from the reaction compartment 356a and/or inner space 342a of the staining apparatus 340a via direction 384 wherein the microscope slide 324 can be removed therefrom (FIG. 33H). This can occur immediately after the heating step, or after one or more additional steps or procedures has been performed on the microscope slide 324. For example the steps of FIGS. 33C-33G can occur several times before the microscope slide 324 is removed in the step of FIG. 33H.

Shown in FIG. 34, an alternate embodiment of the invention is represented as the staining apparatus 400. The staining apparatus 400 has a front wall 402, a back wall 404, a first side wall 406, a second side wall 408, and an inner space 410. Inside the staining apparatus 400 are a plurality of sets of reaction components 412 (six are shown but more or less may be included) similar to the reaction components of any of 1-6 and 29A-33H. In particular, each set of reaction components 412 comprises a movable reaction compartment 414 and a movable slide support element 416 each which is independently movable of each other reaction compartment and slide support element respectively. The slide support element 416 is moved forwardly, backwardly, and rotatingly by a motor assembly 418 comprising a motor 420 and a shaft 422. A motor assembly for moving the reaction compartment 412 forwardly, backwardly and preferably rotatingly is not shown. The staining apparatus 400 is operable in any of the configurations represented in FIGS. 1-6 and 29A-33H and as contemplated elsewhere herein and further as described herein. For example, slide support elements 416 can be moved into and out of the inner space 410 of the staining apparatus 400, and into and out of reaction compartments 412; similarly, reaction compartments 412 can be moved over and sealed about slide support elements 416 or retracted to expose the slide support elements 416. Staining apparatus 400 is further shown as having an X-Y-Z positioning device 430 having as a movable head 432 discussed elsewhere herein which is positioned in the inner space 410 such that the movable head 432 can be moved laterally and vertically over the slide support elements 416 on a rail 434. The movable head 432 in one embodiment of the X-Y-Z positioning device 430 comprises a dispensing element for dispensing a reagent or other dispensable material, such as a cover slip or a bonding material for attaching a cover slip. The movable head 432 may comprise a bar code reader or other mechanism for obtaining information from the microscope slide or from the reagent pack. The movable head 432 may comprise an inkjet printer or laser etching device or other light emitting device for imparting or printing a pattern, symbol, or label on the microscope slide or other device described herein. The movable head 432 may comprise an aspirator for removing a reagent or solution from the microscope slide or slide support element. The staining apparatus 400 may comprise multiple X-Y-Z positioning devices 430 and/or multiple movable heads 432, each separate movable head 432 able to perform one or more of the functions contemplated herein. For example, in one non-limiting example, the staining apparatus 400 may comprise one X-Y-Z positioning device 430 comprising a movable head 432 which is an inkjet printer, another X-Y-Z positioning device 430 comprising a movable head 432 which is an optical code reader and/or scanner, and another X-Y-Z positioning device 430 comprising a movable head 432 which is reagent dispenser and/or reagent aspirator.

In the staining apparatus 400, the reagents are applied to the microscope slide and/or slide support element 416 within the same chamber compartment that contains the reaction compartments 414. In one embodiment of the invention, the optical scanner of the X-Y-Z positioning device may scan the microscope slide on the slide support element to identify and record the location of the biological (tissue) specimen thereon. This information can be used to optimize the placement of the reagent on the microscope slide so that it is deposited directly upon the biological specimen or in a preferred location on the microscope slide for mixing or treatment purposes.

FIG. 35 shows a staining apparatus 400a which is similar to staining apparatus 400 except that staining apparatus 400a comprises (1) a pressurizable common chamber 446 wherein microscope slides on independent slide support elements 416a are exposed to the same pressurization level therein, and (2) a common application chamber (treatment chamber) 444 wherein reagents are applied to the microscope slides. Microscope slides are first inserted into a non-pressurized common application chamber 444 where a reagent is applied thereto by a reagent pack, and/or an X-Y-Z positioning device 430a. After application of the reagent to the microscope slide 446, the slide support element 416a passes into the pressurizable common chamber where each slide support element 416a is first sealed within the corresponding reaction compartment 414a also referred to herein as a corridor or enclosable compartment until the opening through which the slide support element 416a passes into the pressurizable common chamber 446 is closed or sealed. Once the slide support element 416a has been sealed within the pressurizable common chamber 446, the reaction compartment can be retracted to expose the microscope slide to the common pressure level established therein. The advantage of the embodiment of FIG. 35 is that there are fewer components necessary in comparison to the embodiment of FIG. 34, since in FIG. 34 each reaction compartment 414 is separately pressurized, wherein in FIG. 35 each "reaction compartment" 414a is not individually pressurized. Further explanation is provided below.

In the pressurizable common chamber 446 of the present invention such as is shown in FIG. 35, the slide support elements 416a can be moved into and out of the pressurizable common chamber 446 while said chamber is under pressure that is exceeding or is below atmospheric pressure while said pressure is maintained in the pressurizable common chamber 446 even when the independently moving side support elements 416a are moving into the pressurizable common chamber 446 to be treated or are being moved out of the pressurizable common chamber 446 for removal of the treated slide or for placement of a new slide on the slide support element 416a to be moved into the pressurized pressurizable common chamber 446 for treatment under pressure. The slide support elements 416a can be moved into and out of the pressurizable common chamber 446 with changing or releasing or diminishing the pressure therein. The movement is such that each slide support element 416a is moved through a corridor or reaction compartment 414a that is sealed when the reaction compartment 414a is sealed at seals 442 to the wall 440 which separates the pressurizable common chamber 446 from the application chamber (treatment chamber) 444 that isolates the slide support element 416 from the inner space of the pressurizable common chamber 446. The individual corridor or reaction compartment 414a is able to be sealed at its proximal end to seal the proximal end against the wall 440 of the pressurizable common chamber 446 having openings through which the slide support element can pass. This seal 442 can be any sealing means contemplated herein or any other sealing means able to function in accordance with the invention. The individual independently moving slide support element 416a within the corridor or enclosable compartment 414a could now move through an opening in the wall 440 of the pressurizable common chamber 446 while inside the sealed inner space of the sealed compartment 414a. Even after the slide support element 416a has moved through the access opening of the pressurizable common chamber 446, the enclosable compartment 414a or corridor remains sealed over the opening in the wall to maintain pressure within the chamber 446.

FIG. 36 shows a staining apparatus 400b which is similar to staining apparatus 400a in that staining apparatus 400a comprises (1) a pressurizable common chamber 446b wherein microscope slides on independent slide support elements 416b are exposed to the same pressurization level therein, and (2) a common application chamber (treatment chamber) 444b wherein reagents are applied to the microscope slides. Microscope slides are first inserted through a door or sealing means 403b into the non-pressurized common application chamber 444b where a reagent is applied thereto from a reagent pack, and/or optionally an X-Y-Z positioning device (not shown) supplied from a remote source. After application of the reagent to the microscope slide 446b, the slide support element 416b passes through a door 441b into the pressurizable common chamber 446b where each slide support element 416b is sealed therein upon closure of the door (or sealing means 441b. Once all slide support elements 416b have been sealed within the pressurizable common chamber 446b, the common pressure level can be established therein and the treatment protocol can proceed. In the embodiment of FIG. 36 all microscope slides are exposed to the same pressure level.

Referring now to FIGS. 37A-39B, the present invention is further directed to a novel method of applying (spreading) a reagent to a microscope slide or analytic plate or substrate having a biological specimen attached thereto. In one embodiment of the invention, the reagent is a DNA or RNA "probe" but may be any reagent described herein, including a liquid adhesive material. Such probes are well known in the art. Probes or "probe mixtures" (and other reagents) are expensive and it is an object of the present invention to provide a technique that efficiently applies the reagent mixture to the microscope slide to optimize coverage thereover yet which uses only a minimum amount of the reagent mixture. The amount of a reagent, such as a probe, that is routinely used to perform manual in-situ hybridization is 10 µl under a standard 22 mm×22 mm cover slip. The present invention contemplates utilization of the similar volume of reagent (e.g., 10 µl) but can evenly spread this quantity of probe mixture across a surface area greater than 22 mm×22 mm.

Referring in particular to FIGS. 37A-37F, an example of such a spreading device is shown. The spreading device 500 has a gap 502 that, for example, is 3-25 µm deep (but may be deeper). Typically, a tissue specimen (biological specimen) 504 used for in-situ hybridization is placed on a microscope slide 506. The microscope slide 506 has a label end 508 and a treatment surface 510. The thickness of the tissue specimen 504 is typically between 2-7 µm and more preferably between 4-5 µm. Thus the gap 502 of the spreading device 500 preferably has a depth that is 1-23 µm higher than the tissue specimen 504; or 2-15 µm, or 3-10 µm, or 5-7 µm above the tissue specimen 504. The spreading device 500 can be, for example, one inch wide and have end blocks 512 that are up to 1 inch in length and generally 0.01-5 µm in width. These end blocks 512 thus touch the microscope slide 506 0.01-5 µm from the edge of the microscope slide 506. The space between the two end blocks 512 and the microscope slide 506 encompasses the gap 502 of the spreading device 500. Preferably the dept of gap 502 extends at least 0.01 µm-50 µm above the highest point of the tissue specimen 504 on the microscope slide treatment surface 510. Preferably the depth of gap 502 is 0.1-5 µm, or more preferably 1-3 µm above the tissue specimen 504 to be covered by the reagent 514 disposed thereon.

The depth of the gap 502 of the spreading device 500 determines the thickness of a layer 516 (also referred to herein as a film or coating) of the reagent 514 that can be spread across the microscope slide 506 evenly. The thickness of the layer 516 is important so the reagent 514 forms a film or coating that is distributed evenly across the treatment surface 510 and the tissue specimen 504 thereon with the predetermined thickness of the gap 502 of the spreading device 500. The length of the spreading device 500 (measured from across the width of the slide 506) can be any size to accommodate the tissue specimen 504 on the slide 506. Tissue specimens 504 can be of any size in the art that can be placed, for example on a microscope slide 506 or other appropriate analytic plate. Even a very tiny tissue specimen 504 can have a thin coating of reagent 514 spread across its surface by the spreading device 500 of the present invention. For example, the total length of the spreading device 500 could be as little as 3-5 mm, wherein the length of the gap 502 across the length of the spreading device 500 is generally about 1-4 mm. In this version, the width of the layer 516 would be 1-4 mm, and the thickness would be the depth of the gap of the spreading device 500. In an alternate embodiment (FIG. 37B), a spreading device 500a is like spreading device 500 except it comprises block portions 512a which extend about a portion of the underside of the slide 506. The spreading device 500a may have a handle 518 to enable it to be moved manually. The spreading device 500 may be moved across the microscope slide 506 along a track 520 which may be operatively associated with a motor or other means of causing movement of the spreading device 500.

In one example, the tissue specimen 504 is a prostate or breast biopsy sample which is 1 mm wide and 1.2 cm long. A very small spreading device 500 as described above could be used to lay a thin layer 516 of reagent 514 over the entire tissue specimen's width and length. The spreading device 500 (or 500a) of the above example could be about 3 mm wide and have a gap depth of 6-7 µm in gap 502. A 2-4 µl drop of reagent 514 could then be used to lay the thin layer 516 over the tissue specimen 504 by movement of the spreading device 500 (or 500a) thereover without any waste of reagent 516. The spreading device 500 (or 500a) of the present invention can be of any size that is necessary to lay a thin layer 516 of reagent 514 over a biological (tissue) specimen 504 on a substrate such as a microscope slide 506. Other biological testing substrates are known and can be used with the present invention such as Petri dishes, plates of glass or plastic, and others as discussed elsewhere herein.

The spreading device of the present invention preferably has a gap 502 preferably is at least 0.01-20 µm above the tissue specimen 504. The thickness of the tissue specimen 504 is between 3-7 µm and more preferably between 4-5 µm. The spreading device 500 (or 500a) of the present invention may have a gap that is 4-10 µm and more preferably between 6-7 µm or just one, two, or three µm above the biological specimen. The gap depth of the spreading device can be, for example, 0.01 µm, to 0.1 µm, 0.1 µm to 1 µm, 1 µm to 20 µm, 20 to 50 µm above the microscope slide's 506 surface. Preferably the thickness of gap 502 is 1-3 µm above the specimen 504 to be covered by the reagent or solution film. The thickness of the gap 502 determines the thickness of the layer 516 or film of reagent 514 that can be spread across the slide 506 evenly. The thickness is important so the reagent 514 forms a layer 516 that is distributed evenly across the microscope slide 506 and specimen 504 with a thickness of the gap of the spreading device 500 (or 500a). The length of the spreading device 500 (or 500a) can be any size to accommodate a biological specimen. The reagent 514 that can be spread by the spreading device 500 (or 500a) can be any reagent used in a laboratory setting including, but not limited to: stains, probes, DNA and RNA molecular probes, immunoreagents, histochemical reagents, antibodies, in-situ reagents, mineral oils, ionic or non-ionic reagents additives, SDS, Tween, Brij, detergents, alcohols, polyols, glycols, de-waxing solutions, hydrating solutions, fixatives, detection reagents, thermoplastic resins, plastic polymers, cover slip mountants for coverslipping the specimen without the need for plastic or glass cover slips, fixatives, etc.

When using the spreading device 500 (or 500a) of the present invention on a microscope slide 506, the initial position of the spreading device 500 (or 500a) could be at either terminal end of the treatment surface 510 of the microscope slide 506. The distal end away from the label end 508 of the microscope slide 500 (the non-label end) is a preferred initial starting position (FIGS. 37C-37D). The reagent 514 is placed as a drop in front of the spreading device 500 (or device 500a) (FIGS. 37C-37D), then the spreading device 500 is moved over the drop of reagent 514, over the tissue specimen 504, and to the label end 508 of the slide 506 thereby depositing the layer 516 of reagent 514 evenly across the slide (FIG. 37E). Once the spreading device 500 (or 500a) has touched the drop of reagent 514, the reagent 514 spreads across the gap 502 of the spreading device 500 (or 500a) by capillary action and the spreading device 500 (or 500a) is moved slowly toward the label end 508 of the microscope slide 506. The end blocks 512 (or 512a) pass lengthwise over the peripheral side edges of the microscope slide 506. The reagent 514 is thus spread evenly under the gap 502 of the spreading device 500 (or 500a) across the microscope slide 506. The spreading device 500 (or 500a) is then retracted to the starting position on the slide (FIG. 37F). The thickness of the layer 516 of reagent 514 deposited is dependent on the viscosity of the reagent 514 and the depth of gap 502 of the spreading device 500 (or 500a). The viscosity of the reagent 514 can be of any viscosity known in reagents for laboratory testing. In one example, the viscosity may be that of mineral oil at ambient room temperature. Molecular probe dilutions have similar viscosity to mineral oil and this is a viscosity that can be used by this method of the present invention.

The spreading device 500 (or 500a) of the present invention can be disposable or reusable. The spreading device of the present invention can be molded out of plastic, thermoplastics, polymers, metal, glass, ceramic, and/or rubber, or combinations thereof, and can be labeled or color-coded to indicate the thickness the gap of the spreading device. The spreading device may be constructed of metal and coated with a polymer or plastic. In one example, a spreading device may be rated as having a gap of 6 µm, and has that numerical number stamped thereon, and has a particular color such as blue. This "blue" applicator when used would lay down a reagent layer with a thickness of up to 6 µm across the microscope slide for example. In an alternate embodiment, the spreading device can have a handle attached thereto for manual use (see FIG. 37B), or other appendages for the attachment to an automated instrument described in further detail below. The spreading device can spread a layer of a film or any reagent used in the laboratory setting such as, but not limited to: stains, probes, DNA and RNA molecular probes, immunoreagents, histochemical reagents, antibodies, detection reagents, thermoplastic resins and mountants for coverslipping the specimen without the need for plastic or glass cover slips, or fixatives.

As noted above for FIGS. 37-39, the spreading device is preferably automatically movable. The spreading device may comprise a plastic or polymer coated metal gap applicator which can be moved by a moving magnet present in the slide support element. The reagents used with the spreading device can have detergents present to help the spreading out of the reagents. These detergents are ionic or non-ionic detergents, glycols, polyols, etc.

As explained elsewhere herein, in one version of the method of using the spreading device 500, a microscope slide is placed on the slide support element, the correct spreading device is loaded onto the slide support element and rests on the slide, the microscope slide is moved into the staining apparatus to the treatment and application position, a reagent is either dispensed by the reagent pack, X-Y-Z dispenser, dispensing element, a remote source, or the reagent is dispensed from the dispenser integrated into the spreading device, the spreading device moves across the microscope slide and over the biological specimen to lay down an exact thickness of reagent equal to the thickness of the gap of the spreading device, the microscope slide is incubated and rinsed, and another reagent then can be dispensed onto the slide or the dispensed reagent can be spread again by the spreading device until the protocol is complete. If the slide is to be coverslipped by the spreading device the final reagent would be applied to the dried microscope slide and a coverslip mountant would be applied to front of the spreading device which would move across the slide to lay down an exact thickness of coverslip mountant to the slide. The slide is then heated to dry and harden the coverslip reagent and the slide is then removed and can go directly to the microscope for evaluation by a technician.

In reference to FIGS. 38A, 38B, 39A, and 39B, the slide support elements and associated reaction compartments contemplated herein (such as, but not limited to, slide support element 310, and reaction compartment 316) can be modified to incorporate the spreading device 500 (or 500a) described herein. The spreading device 500 for example, can be attached to a portion of an automated push-pull mechanism 522 which could pull and/or push the spreading device 500 over the microscope slide 506 to automate the entire spreading process (FIG. 39A, 39B). The spreading device 500 may have pins or some means to attach the spreading device 500 to the track 520 on the slide support element 310 or adjacent thereto or elsewhere around the slide support element 310 to move the spreading device 500 over the treatment surface 510 of the slide 506. The spreading device 500 or 500a may be attached to the extendable push-pull mechanism 522 via a pin 524 for example. Each reaction slide support element 310 and/or reaction compartment 316 of the staining apparatus 300 (or other staining apparatus contemplated herein) can have the ability to utilize these spreading devices to spread reagents upon the microscope slides 506 positioned thereon.

Shown in FIGS. 39A-39B is an embodiment of an automated push-pull mechanism 522 for moving the spreading device 50. When the microscope slide 506 is placed on the slide support element 310 before testing is started, the technician could position the spreading device 500 to the instrument and at the appropriate time a reagent 514 could be deposited on the microscope slide 506 and the spreading device 500 could then be moved over the microscope slide 506 to evenly apply the reagent 514 over the tissue specimen 504. Once the entire staining process (the entire treatment protocol) is complete the technician could remove the microscope slide 506 and spreading device 500 and discard or clean the spreading device 500. In a preferred embodiment the spreading device 500 is color coded and is disposable.

In an alternate embodiment, the spreading device 500 (or 500a) described herein can have the reagent already contained within a reservoir in the spreading device 500 (or 500a) and dispensed therefrom onto the microscope slide 506. When loading the staining apparatus 300, the technician could remove a protective cover or closure device on the spreading device to expose the reagent to be applied to the microscope slide 506. In accordance with the invention, the technician can place the microscope slide and spreading device onto the slide support element 310. Once the slide support element 310 and microscope slide 506 thereon is inside the reaction compartment 316, the reaction compartment 316 can be depressurized or held in a vacuum. This vacuum environment can pull the reagent out of the spreading device reservoir and onto the microscope slide and the spreading device can then move and spread the reagent over the microscope slide as described above. In an alternate embodiment, the reaction compartment 316 can be under pressure to expel the reagent from the spreading device reservoir. In an alternate embodiment, the spreading device is attached to an armature on the X-Y-Z positioning device and is movable thereon, rather than on the slide support element or on a reagent pack.

Shown in FIGS. 40-42 is an alternate embodiment of a reagent pack of the present invention designated therein by the general reference numeral 550. Reagent pack 550 has round configuration such as a disk shape. The reagent pack 550 comprises a plurality of "pie-shaped" container portions 552 each having a reagent container 554 thereon, and a central aperture 556 through which a pin or other holding device on a reagent pack support device of the invention can engage the reagent pack 550. The reagent pack 550 operates by being rotated to an application position wherein a reagent in the reagent container 554 can be expelled onto a microscope slide on a life support element of the invention. Reagent pack 550 is shown as comprising eight container portions 552 but it will be understood by a person of ordinary skill in the art that the reagent pack 550 could comprise 1, 2, 3, 4, 5, 6, 7, 8 9, 10, 11, 12 or more container portions 552 rather than the eight shown herein. FIG. 41A shows reagent pack 550 taken through line 41A-41A of FIG. 40. In this embodiment, the container portion 552 comprises a "blister" or "bubble" container 554a which is designated to be "crushed" open. FIG. 41B shows an alternative version of container portion 552 taken through line 41B-41B of FIG. 40 showing a "piston" type container 554b wherein the reagent in the container 554b is expelled by compression of a "piston" in the container 554b which causes expulsion of the reagent therein through an aperture 560 therebelow. Represented by the reference number 558 in an embodiment of a spreading device 558 such as described elsewhere herein which can be used to spread the reagent over the microscope slide.

Shown in FIG. 42 is a single container portion 552 of reagent pack 550 and tab slots 568 into which the connecting tabs 566 can be inserted wherein the plurality of container portions 552 can be connected into the reagent pack 550, or could be disconnected and rearranged and reconnected together. The tabs 566 are not the only connecting means to connect the container portions 552 together and indeed any connecting device known in the art for use as a connecting means could be used as long as the resulting reagent pack 550 functions in accordance with the invention. Further, the circular reagent pack may be of integral, unitary construction, that is, the reagent pack may not be constructed of separable "pie" portions but may be constructed of a solid base.

Shown in FIGS. 43A-43B in cross-section is a staining apparatus 580 which is the same and other staining apparatuses contemplated herein except as described below. Staining apparatus 580 has a front wall 582, an inner space 584, and a slide support element 586 having a sealing end 590 and sealing means 596. The slide support element 586 is sized to fit into a reaction compartment 588 in a manner similar to other slide support elements and reaction compartments described herein except that when slide support element 586 is inserted into reaction compartment 588 (for sealing a microscope slide therein), the sealing end 590 of the slide support element 586 sealingly engages with a mating surface on the front wall 582 to form a seal between the end portion 590 of the slide support element 586 and the front wall 582 as indicated in FIG. 43B. An advantage resulting from this embodiment of the invention is that a separate door is not necessary to close the aperture in the front wall 582 through which the slide support element 586 is passed. A reaction pack support device of the invention could have a similar sealing means in an end portion thereof. Preferably the sealing end 590 is a ground or polished glass surface as is the mating surface on the front wall 582, or it could be any similarly ground or polished surface in the material from which the sealing end 590 of the slide support element 586 is constructed. The opposite end of the slide support element 586 could have a similarly configured sealing end portion and in an alternate embodiment, the sealing end 590 of slide support element 586 could be designed to form a seal in a mating portion of an inner wall of an embodiment of the present invention wherein the staining apparatus comprises a pressurizable common chamber such as inner wall 440 of staining apparatus 400a or inner wall 440b of staining apparatus 400b. For example in staining apparatus 400b, the slide support element 416b could have a sealing end such as sealing end 590 which sealingly engages wall 440b for forming a seal therebetween, and which replaces the door 441b therein.

In one embodiment of the present invention, a microscope slide is placed on the corresponding slide support element when it is in a position outside of the staining apparatus. The reagent pack specific for that particular microscope slide similarly would be placed on the corresponding reagent pack support device (wherein the loading position for the reagent pack support device is inside or outside of the staining apparatus). The reagent pack preferably would feature a bar code, OCR symbol, machine readable symbol or code that can be read by an optical scanner or scanners associated with the staining apparatus to determine what type of treatment protocol is to be performed on the corresponding microscope slide.

Once the microscope slide has been placed on the corresponding slide support element the technician can place the appropriate reagent pack on its reagent pack support device and press a button nearby the slide support element or reaction compartment or front wall of the staining apparatus or on the screen of the microprocessor to start the treatment process. Since the lab technician knows what particular protocol that is required for each microscope slide positioned, in an alternative embodiment the tech would place the microscope slide on the slide support element corresponding thereto and place the reagent pack on its reagent pack support device and push the reagent pack or reagent pack support device gently into the staining apparatus. Once the reagent pack support device is moved about 0.1 to 1.5 cm manually towards the staining apparatus, the reagent pack support device will recognize this movement and will automatically continue movement of the reagent pack into the staining apparatus without further assistance from the technician. The independently movable slide support element can, at this time, automatically move into the staining apparatus when the reagent pack support device begins to automatically move into the staining apparatus or shortly thereafter.

Once the slide support element and the reagent pack support device (and reagent pack) are inside the staining apparatus, the microprocessor will recognize that a new reagent pack has been moved into the staining apparatus and the staining apparatus will position a movable optical recognition character reader or scanner over the reagent pack's optical character recognition (OCR) code and that particular code with be identified as a new protocol for the microscope slide associated with that reagent pack. Preferably, there is no further assistance needed from the technician once the reagent pack support device is automatically moved into the staining apparatus. The microprocessor will take over and all the information from the OCR code on the reagent pack will be deciphered to start a new treatment protocol to the corresponding new microscope slide. Since the microprocessor recognizes the OCR code present on the reagent pack, the staining process will then be carried out by all the automated processing devices under its control. Preferably, there is no need to have an OCR code on the microscope slide to link the slide with its reagent pack. This one step identification, of the present invention, is preferred versus the prior art identification of slides and reagent container where both the slide and the reagent container need to have OCR code present thereon to locate and dispense the right reagent to the right slide. This saves money and time by not placing an OCR code on the prior art microscope slide to be processed by automation.

An alternate version of identifying the reagent pack is the reagent pack can have any wireless device know in the art of recognizing wireless devices by a microprocessor. The reagent pack can have, for example, a wireless device embedded or on the reagent pack. The reagent pack can have embedded information in the form of microchip or other device to store the protocol information that can be recognized and deciphered by the microprocessor. When the protocol and slide processing is completed, the microprocessor will alert the technician that the microscope slide is ready to be removed from the staining apparatus. This alert can be is form of a sound and/or visual effect either near the particular slide support element or front wall of the staining apparatus or on the microprocessor's screen. The notification that the treatment protocol is completed and the slide can be removed from the staining apparatus can be provided by any known device or devices both audible and/or visually known in the art of notification of microprocessor controlled devices. A preferred notification is both an audible alert, which can be of different sounds or pitches relating to the entire process from start to removal of the microscope slide, along with a visual alert on the staining apparatus or on the screen of the microprocessor.

Each slide support element of the present invention may have a slide support eject button associated therewith, and each reagent pack support device may have a reagent support eject button associated therewith. Each set of reaction components may comprise a protocol status indicator light or lights, "quick code" buttons, and a LCD or LED screen for visual information regarding the protocol, reagent(s), and or microscope slide.

The regent pack, strip, or individually contained reagent or reagents preferably features a bar code, OCR symbol, machine readable symbol or code or other similar symbol that can be read by the apparatus's optical scanner or scanners to determine what type of protocol is to be performed on the corresponding microscope slide. The reagent pack, strip, or individually contained reagent or reagents or the microscope slide can also have a "quick code" that corresponds to a "quick key" or "hot key" on the apparatus that can be entered into the apparatus manually to identify the treatment protocol for a particular slide. Once the microscope slide is placed on its slide support the technician would place the desired reagent pack on its reagent pack support device and press a button nearby the slide support element or reaction compartment on the front wall of the staining apparatus front panel or microprocessor screen to start the treatment process. Since the lab technician knows what particular protocol that is required for each microscope slide positioned on its independently moving slide support element, in an alternative embodiment the technician would place the microscope slide on its slide support element and place the reagent pack on its reagent pack support device and push the start button on the apparatus to initiate the automatic independent movement of the slide support element and reagent pack support device into the inner space of the staining apparatus of the apparatus. The apparatus would then read the OCR code or symbol on the reagent pack to program the microprocessor for that particular treatment protocol for the microscope slide on the slide support element. The microprocessor with take over and all the information from the OCR code on the reagent pack will be deciphered to start a new treatment protocol to the corresponding new microscope slide. The apparatus can also read the slide's OCR code or symbol, if present, to confirm that the reagent pack selected by the technician correlates to that particular microscope slide. In an alternative embodiment, the reagent pack's OCR code can be manually scanned by a wired or wireless hand held scanner for the manual programming of the treatment protocol. The user would place the microscope slide onto a slide support element and either scan the OCR code of the reagent pack prior to putting the reagent pack on the reagent support or after the reagent pack is placed onto the reagent pack support device. The apparatus would then start the protocol by automatically moving the slide and reagent pack into the apparatus. In an alternate embodiment, the user programs the apparatus for a particular treatment protocol by entering into the apparatus or staining module a "quick code" that is present on the reagent pack. This "quick code" can be a number, symbol, letter, or identified by a particular color code. For example, a number "2" can be present on the reagent pack, or the letter "C" or particular color code like "blue". The user would place the microscope slide on the corresponding slide support element then place the required reagent pack on the reagent pack support device and press the "quick key" on the apparatus that has the same number, letter, or color code that is present on the reagent pack. These quick codes can also be on the microscope slide and/or the reagent pack. The "quick codes" are useful when common or repetitive protocols are used. This speeds the time of programming the apparatus for a particular repetitive protocol. For example, if the user has five "estrogen receptor" protocols to be analyzed at one time, the user would place the five slides onto their corresponding slide support elements and place the 5 reagent packs for the "estrogen receptor" protocol onto their reagent pack support devices. The user would then press or activate the individual "quick code" button or icon for that staining module that corresponds to the estrogen receptor protocol's "quick code" for each microscope slide. For example, the "estrogen receptor" protocol is part of a staining protocol class known in the art as a "prognostic" test. Since all prognostic tests could have the same incubation times, the "prognostic class" of antibodies could all have the same "quick code". The user can now program all the "prognostic" protocols for each "prognostic" slide by pressing or activating the single "quick code" button to program the apparatus for a "prognostic" protocol. Seven slides for a "prognostic" panel could have, for example, seven prognostic antibodies like estrogen receptor, progesterone receptor, Ki-67, Her-2, bcl-2, p-glycoprotein, and p53. The user would place each microscope slide on its corresponding slide support element and then place the reagent pack for that "prognostic" antibody test and then press or activate, for each of the sets of reaction components, the "quick code" button. The programmed incubation times would be the same for each module even if the antibody test was different for each slide. Because this class of antibodies being used, in this example the "prognostic" antibodies, all have the same "quick code" on their reagent pack or slide, different prognostic reagent packs can have different prognostic antibodies present but all have the same protocol when it relates to the incubation times for the whole class.

Another class known in the art is the "core" antibodies. These antibody protocols also have different primary antibodies in each reagent pack, but the incubation times can be the same. The "core" antibodies can all have the same "quick code" presented on their reagent pack. They can all be a different antibody test or protocol only they all have the same incubation times for each step. An example of this type of class of antibodies tests can have the letter "A" on their reagent pack. The user would then press or activate the "A" button associated with the staining module and the test would start. The "quick code" buttons can be pre-set at the factory or can be user manipulated depending on the user preference. Each "quick code" button can be programmed with a different protocol incubation time or any other variant relating to protocol method and stored for future use with that "quick code" button. It would be known that any variant to this method can be used. Whether the slide is placed first and the reagent pack is placed second or vice versa is anticipated. Also whether or not the slide support element or reagent pack support device are moved into or are outside of the apparatus before operation is contemplated. Any step of moving of the slide support element or reagent pack support device, either semi-automatically or completely automatically is contemplated.

The steps of placing the microscope slide on the slide support element, the placement of the reagent pack on the reagent pack support device, automatic scanning of the OCR code, manual scanning of the OCR code, and pressing or activation of the "quick code" buttons can all be used in any combination, method and or sequence. Each individual slide support element can automatically move outside the staining apparatus to place a microscope slide thereon or for removal of the microscope slide when a test is complete by pushing the slide support eject button on the apparatus. The slide support element and reagent pack support device can also be semi-automatically moved outside or inside the staining apparatus by manually moving the slide support element or reagent pack support device about 0.1 to 1.5 cm thereby activating their automatic movement mode. Once the slide support and/or the reagent support is manually moved about 0.1 to 1.5 cm inwards towards the staining apparatus or moved towards the front wall thereof, the slide support element and/or the reagent pack support device would recognize this manual movement and the apparatus will take over by automatically moving the slide support element and/or reagent pack support device into or out of the staining apparatus. This movement is operationally similar to the mode of operation of a computer CD-ROM drive door or drawer of DVD machine drawer. In an alternate embodiment, the slide support element and the reagent pack support device can move totally automatically and independently by pushing a button on the staining apparatus to initiate said movement. A button for insertion or ejection of the slide support element and reagent pack support device can be present for each set of reaction components on the front panel (front wall) of each staining module. The insertion/ejection button can be a single button for moving both or may comprise separate buttons for each movement.

As explained elsewhere herein, the slide support element and the reaction compartment can be made out of glass with a polished seal matingly sealing the inner surface of the reaction compartment and the outer surface of the slide support element. For example, a glass syringe commercially available from Popper and Sons can be modified for this embodiment. A Perfecktum™ glass hypodermic syringe (cat no: 5159, 50 cc syringe) or equivalent could be modified to produce a glass slide support element (constructed from the inner barrel or plunger of the syringe) and a glass reaction compartment (constructed from the outer barrel of the syringe). The sealing means is the polished glass between the inner barrel (the slide support element) and the outer barrel of the syringe (the reaction compartment). This polished glass mating seal between the slide support element and the reaction compartment enables the slide support element to be easily moved into and out of, and rotated within, the reaction compartment. For example, the slide support element can be tilted, spun, or otherwise rotated within the reaction compartment as well as be moved laterally forward and backwards while in the reaction compartment. The advantage of this design is that the slide support element, inside the reaction compartment is able to move forward, backwards, and in a circular motion (rotated) while forming and maintaining a pressure tight seal inside the reaction compartment formed by the polished glass seal between the slide support element and reaction compartment. The circular, rotational, motion is ideal to "spin" the slide support element to cause removal of a reagent or wash solution from the slide by centrifugal force. The reagent is "spun" away from the microscope slide and drained from the reaction compartment and is then ready for the next reagent or can be "spin dried" prior to remove of the microscope slide from the slide support element. The slide support element, because of the polished glass seal, is very easily moved within the reaction compartment. For example, in one version, a simple twist of the slide support element can cause the slide support element to make several revolutions within the reaction compartment even if the reaction compartment is under positive (or negative) pressures that exceed (or are below) atmospheric pressure. The microscope slide can be in any position to be washed by a wash reagent dispenser and then, if necessary blown off by a gas pressure dispenser, with the slide at any angle on the slide support element. The home position for the microscope slide is when the upper surface of the slide faces upward (the "12:00 o'clock" position or 0°). The slide could be washed at the 12:00 o'clock position, the 3:00 o'clock position (90° from home position), the 6:00 position (180° from home position), 9:00 position o'clock (270° position) or any degree position between the home position (0°) and 360° from home position. The preferred positions for washing the slide would be between the 0° position (home position) and 180° (6:00 position). Slide processing devices can be positioned anywhere around the slide support elements to dispenses reagents, gas, or other processing device proposes at any angle the microscope slide is positioned on the movable slide support element. For example, the staining reagents (antibodies, molecular probes, biological stains, detection reagents, pretreatment reagents, antigen retrieval solutions, or other reagent or solution described herein) could be dispensed to the microscope slide from above the slide support element in the home position ("12 o'clock" or "0 degree" position) and then the microscope slide could be rinsed at the "6:00 o'clock" position (180° position) by a rinse wash reagent dispenser and then spun dried to remove the wash reagent and then drained from the reaction compartment.

In one embodiment, the use of individual and independently mechanized spinning or centrifugal force producing slide support elements that support only a single analytic plate is contemplated. In one embodiment of the present invention, the microscope slide is rotated or spun to effect centrifugal force movement or centripetal motion for removal of reagents, water, liquids, solutions, buffers, aqueous and non-aqueous liquids present in-vivo, in-vitro, and or in-situ in, around, or associated with the biological specimen, in particular paraffin embedded biological specimens floated by water onto microscope slides, including water trapped between the paraffin embedded tissue and the microscope slide from floating a tissue section from a histological water floatation water bath or during the production of placing a biological specimen onto a microscope slide with a aqueous or non-aqueous reagent or solution.

In one embodiment, the inventive concepts disclosed herein are directed to the automated removal of the histological water floatation water bath water away from at least one recently mounted "wet" paraffin embedded biological specimen that was floated onto at least one microscope slide. The present invention method comprises floating at least one hydrophobic paraffin embedded biological specimen section onto at least one functionalized microscope slide with an aqueous medium like the water from a histological floatation water bath or other floatation liquid from a histological floatation bath or other floatation liquid method know in the art to float a paraffin section onto a microscope slide and then placing the wet microscope side with the wet paraffin biological section thereon onto the automated apparatus of the present invention such that once the apparatus is initiated to start the floatation liquid removal process the microscope slide support element with the microscope slide and biological specimen thereon is rotated so as to cause the microscope slide and the paraffin embedded biological specimen to move in a way that causes the water or floatation liquid disposed between the microscope slide and the paraffin embedded biological specimen to be completely removed or drawn from or substantial removed or drawn from between the microscope slide and the paraffin embedded biological specimen and to remove any water or floatation liquid on the microscope slide on any surface of the microscope slide and removing substantially all the water or floatation liquid from under the paraffin embedded biological specimen without dislodging, tearing, folding, or otherwise damaging the delicate biological specimen while the water or flotation liquid is being removed or drawn from the microscope slide and drawn from under and away from the paraffin embedded biological specimen. This water or flotation liquid removal method is completed prior to an optional step of heating the microscope slide to melt the paraffin and/or before a required step of de-waxing or deparaffinizing the paraffin from the paraffin embedded biological specimen prior to treating the de-waxed or depraffinized biological specimen with a staining protocol.

Figure 34A:
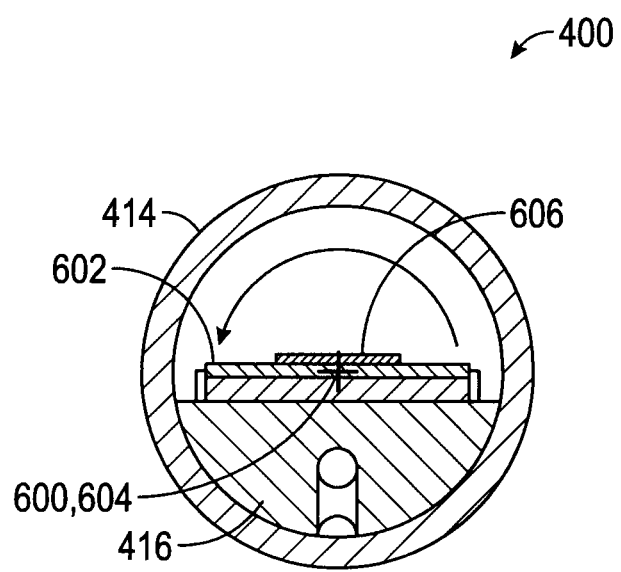
FIG. 34A is cross-sectional view illustrating the apparatus of FIG. 34 for use in removing floatation liquid.

In one embodiment, the slide support element, such as the slide support element 416 illustrated in FIGS. 34 and 34A, has a longitudinal axis 600. Similarly, the microscope slide, such as the microscope slide 602 depicted in FIGS. 34 and 34A, has a longitudinal axis 604. The microscope slide 602 is illustrated with a paraffin embedded biological specimen 606 floated thereon. In one embodiment, the slide support element 416 is configured to be rotated about the longitudinal axis 600 and to support the microscope slide 602 with the longitudinal axis 604 of the microscope slide 602 axially aligned with the longitudinal axis 600 of the slide support element 416. As such, the slide support element 416 and the microscope slide 602 rotate about a common axis.

Because the microscope slide is centrifugally rotated about the microscopes slide's longitudinal axis (i.e., long length (approximately 3 inches) vs. short width (approximately 1 inch), the centrifugal force or tangential acceleration or lateral acceleration of the water is relatively low since the axis of rotation forces incurred or subjected on the biological specimen is low due to the close proximity of the biological specimen to the axis of rotation. The paraffin embedded biological specimen remains intact due to the low forces generated on the water under the paraffin section to move from underneath the paraffin section and therefore move the trapped water under the paraffin section toward the edges of the microscope slide in a rather slow, calm, steady, controlled, reproducible, and orderly fashion vs. a violent pulling of the water away from the underneath of the paraffin section by rotating the slide in a different orientation or different axis of rotation or spinning that could possible tear, move, or damage the fragile paraffin embedded biological specimen if the microscope slide with paraffin specimen attached was centrifugally spun on an axis other than the microscopes slides long axis.

The controlled movement of the water from under the paraffin section as well as water on the microscope is due to the very low forces placed on the water and paraffin biological specimen during the spinning of the microscope slide and biological specimen in the orientation of the spinning being in the center of the microscope slide. The forces placed on the water during spinning is low anywhere on a microscope slide because the axis of rotation is in the center of the microscope slide and the paraffin section can only be slightly off center due to the fact that the functional surface area to place a paraffin section on a microscope side is always going to be very close to the midline or center of rotation of the microscope slide because the slide in spinning along the longitudinal axis of the microscope slide. The paraffin section will generally not be any further than 0.5 inches of center in either direction from the midline since the width of a standard microscope slide is 1 inch wide.

In another embodiment, the microscope slide may be supported by the slide support element with the longitudinal axis of the microscope slide in a spaced apart, parallel relationship to the longitudinal axis of the slide support element, or a perpendicular relationship, or at any angle relative to longitudinal axis of the slide support element (i.e., center of rotation). In another embodiment, the slide support element may be configured to support a plurality of microscope slides. Further, the slide support element may be rotated about an axis spaced a distance from its longitudinal axis whereby the slide support element and the microscope slide are caused to revolve about a center of rotation.

In another embodiment, at least one microscope slide support can be positioned during rotation at any orientation, angle, grade, position, or spacing from or on a center of rotation regardless of the axis of rotation [i.e.—axis of rotation being horizontal, vertical, tangential, angular, parallel, perpendicular, etc] to the relationship of the at least one microscope slide support. Any orientation, angle, grade, position, or spacing of the at least one microscope slide support with microscope slide thereon in relation to a center of rotation is contemplated.

The types of microscope slides that may be used for the present invention are known as positive charged slides. These positive charged slides are commercially available or derived from U.S. Pat. No. 7,731,811.

All the motion controls and devices contemplated for the motion or movement by spinning, rotating, or producing centrifugal force may be devices well known in the art of mechatronic systems, such as the motor assembly 418 depicted in FIG. 34. Such mechatronics devices and systems are featured in *Mechatronics An Introduction*, Robert H Bishop, 1957, ISBN: 0849363586, Taylor & Francis Group. Mechatronics is the worldwide interpretation of use of electrical and mechanical device(s) in an automated system. Mechatronic systems are highly advanced electrometrical systems using advanced electrometrical devices and sensors. These known mechatronic systems or electromechanical means can use a combination of power sources and devices like AC, DC, pneumatics, steam, compressed gases, high and low pressure gases, high and low pressured liquids, electric motion systems, electric stepper motors, pneumatic stepper motors, pneumatic motion systems, and hydraulic motion systems, electrical valves, electric operated pneumatic valves, pneumatic valves, air, gas, and electric pinch valves, sensors, micro-sensors, controllers, microcontrollers, PID controllers, microprocessors, computer interfaces, and any combination of these listed electrometrical or mechatronic systems or devices.

Examples of reagents, buffers, solutions, chemicals, and liquids, that can be removed by centrifugal force or spinning, are, but are not limited to, antigen retrieval reagents like citrate buffer, EDTA, TRIS, PBS, with or without surfactants or detergents like SDS, IGEPAL, Tween, Brij, ionic and non ionic detergents, and silicone additives, rinse buffers, immunohistochemical reagents, histochemical reagents, H/E reagents, in-situ hybridization reagents, PCR reagents, coverslipping reagents, silicone oils, mineral oils, detection reagents and processing reagents, liquid reagents, reconstituted dry reagents, biological reagents and aqueous and non-aqueous reagents, aqueous and non-aqueous antigen retrieval reagents or solutions, dry, desiccated, or lyophilized reagents, deparaffinizing solutions (de-waxing solutions), deparaffinizing solutions of D.I. water, deparaffinizing compositions of water with one or more silicone surfactants or silicone additives, stains, probes, DNA and RNA molecular probes, immunoreagents, histochemical reagents, ionic or non-ionic reagents additives, SDS, Tween, Brij, detergents, alcohols, polyols, glycols, aqueous and non-aqueous de-waxing solutions, hydrating solutions, fixatives, detection reagents, thermoplastic resins, plastic polymers, cover slip mountants for coverslipping the specimen without the need for plastic or glass cover slips, fixatives, biological adhesives, coatings, silicone additives and silane coupling agents as described in U.S. Pat. No. 7,731,811; activated or hydrolyzed biological adhesive (i.e., products and reactants form silane coupling agents hydrolysis) as described in U.S. Pat. No. 7,731,811; hydrolyzed biological adhesive by-products like alcohol produced from the hydrolysis of the silane coupling agent coating method describe in U.S. Pat. No. 7,731,811; water from the histological flotation water bath, D.I., water from the histological flotation water bath, water with or without adhesives added to the histological flotation water bath. Other methods known in the art for applying paraffin sections onto microscope slides using liquids other than a histological flotation water-bath, and any other liquid or solution that is known in the art for processing biological specimens mounted onto microscope slides including any type of dry or desiccated reagent, semi-solid reagent or solution, colloidal solution or reagent, residual desiccated reagent, emulsions, or any other substance present on a microscope slide or biological specimen attached thereon that needs to be removed from the microscope slide and/or the biological specimen attached thereto, etc. The revolutions per minute for the rotation, turning, spinning, etc. is in the range from at least 1 rpm up to about 3000 rpm. The revolutions per minute for the rotation, turning, spinning, etc. can also be in the range from at least 250 rpm up to 3000 rpm. The revolutions per minute for the rotation, turning, spinning, etc. can also be in the range from at least 500 rpm up to 3000 rpm.

The inventive concept of "spin drying" or "centrifugal spinning", and "removal spinning" the microscope slide and recently floated or "wet" paraffin embedded biological specimen thereon eliminates this "pooling" of the floatation water bath water under the paraffin section by removing the water entirely from the microscope slide and paraffin embedded biological specimen section, thus eliminating any possible movement or detachment of the paraffin embedded biological specimen section due to "floating paraffin" or "water pooling" movement of the paraffin embedded biological specimen.

One version of removing the residual water present under or on the paraffin embedded biological specimen or on the paraffin biological section and removing the residual water present on microscope slide is absent an evaporative heat step and absent a paraffin melting step. The present invention removes the water, by a spinning or by a centrifugal motion step without an integrated evaporative heat step or integrated evaporative paraffin melting step. After the present invention method of spinning to remove the residual water step is completed, it is understood that an automated protocol step of heating may then be used, from a separate unrelated step, to melt the now water free microscope slide and water free paraffin section, if desired, prior to the application of a de-waxing step (de-paraffinizing solution) to remove the paraffin from the biological specimen for subsequent processing steps relating to a processing protocol. The present invention method step of rotating or spinning or centrifugal motion to remove residual water from the microscope slide and paraffin section is also known as the "paraffin section drying protocol" or "paraffin section drying step".

In another embodiment, the "paraffin section drying protocol" can utilize an integrated heat step that can heat the microscope slide and biological specimen before, during, or after spinning or centrifugal motion. The integrated heat step can start just as the spinning has started and can ramp up the heat to heat the microscope slide and biological specimen during spinning. The integrated heat during spinning can be at any rate of heating or any temperature of heating during spinning. An example of integrated heating would be the heat plate under the microscope slide can be turned on at the start of spinning and the temperature of the heat plate can ramp up from ambient to 60° C. during spinning. The temperature can be ambient at the start of spinning and ramp up to 80° C. while spinning.

The present invention of spinning to remove a liquid or solution from a microscope slide with a biological specimen attached can include any biological specimen know in the art of biological specimens attached to microscope slide and is know as "biological drying protocol" which would include any biological specimen applied to a microscope slide that requires removal of a liquid from a biological specimen and or microscope slide.

In another version, the method of spinning to remove the floatation water bath trapped water can eliminate the need to heat the paraffin section prior to de-waxing. Therefore, eliminating the heated drying step or timed air-drying step completely prior to de-waxing. The present invention removes the entire step of heated drying of the flotation water bath water and/or a timed air-drying step to remove the flotation water bath water and moves straight to de-waxing saving the technician about 1 hour or more time before they can de-wax the specimen. The present invention of centrifugal force or spinning of the slide support or slide holder to remove reagents, buffers, solutions, chemicals, and liquids can be used to remove by-products or chemical products produced from the hydrolysis of the silane coupling agent coating described in U.S. Pat. No. 7,731,811. The silane coupling agent (i.e., silane) coating of U.S. Pat. No. 7,731,811 would be hydrolyzed by the water from the histological floatation water bath. The by-product from the reaction of the hydrolysis of the silane from the histological floatation water bath is the production of alcohol. This alcohol, water, silane mixture under or around the paraffin embedded biological specimen can be removed by centrifugal force or spinning. Once these reagents are spun away from the paraffin section, the biological specimen can lay flat against the microscope slide and the biological specimen will become attached to the microscope slide via silane coupling bonds. Since the biological specimen is now void of water between the paraffin section and the microscope slide, the biological specimen can now attach to the microscope slide via the covalent attachment of the silane coupler to biological specimen and the microscope slide.

The present invention embodiment of "spin drying" the microscope slide and the paraffin embedded biological specimen attached thereon, is due to the present inventions ability to "spin," "rotate," "turn," or "centrifugally spin" a microscope slide with a wet, recently floated paraffin embedded biological specimen attached thereon.

The microscope slide may be rotated, or otherwise turned spun, at varying rates of rotation and for varying periods of time to achieve a desired amount of floatation liquid. Examples of the revolution(s) per minute (rpm) of the spinning, rotating, and/or turning of the present inventions slide support element(s) to remove the histology floatation water bath water and or histology floatation liquids, from a microscope slide that has had a recently floated "wet" paraffin embedded biological specimen attached to the microscope slide are: 500 rpm, 1000 rpm, 1100 rpm, 1200 rpm, 1300 rpm, 1400 rpm, 1500 rpm, 1600 rpm, 1700 rpm, 1800 rpm, 1900 rpm, 2000 rpm, 2100 rpm, 2200 rpm, 2300 rpm, 2400 rpm, 2500 rpm, 2600 rpm, 2700 rpm, 2800 rpm, 2900 rpm, 3000 rpm, 3100 rpm, 3200 rpm, 3300 rpm, 3400 rpm, 3500 rpm, 3600 rpm, 3800 rpm, 3900 rpm, 4000 rpm, 4100 rpm, 4200 rpm, 4300 rpm, 4400 rpm, 4500 rpm, 4600 rpm, 4700 rpm, 4800 rpm, 4900 rpm, 5000 rpm, 5500 rpm, and at least 6000 rpm. In one embodiment, the rate of rotation may be in a range from about 500 rpm to about 6000 rpm. In another embodiment, the rate of rotation may be in a range from about 1000 rpm to about 3000 rpm. In embodiment, the rate of rotation may be in a range from about 1300 rpm to about 2300 rpm.

In an alternate embodiment, the rate of rotation can be less than one revolution per minute (1 rpm). In such an embodiment, the slide support can be "flicked" or move quickly from side to side without making a complete 360 degree rotation. The slide support could start in at the 6:00 position and be moved quickly to the 3:00 position and abruptly stopped to "flick" the water away from the slide. In this embodiment the slide support can start in any position 0 degrees to 360 degrees and move in an alternate position and be stopped abruptly to "flick" away the water from the slide. In this embodiment the slide support can start at any position from 0 degrees to 360 degrees and end at any position from 0 degrees to 360 degrees as long at the slide support stops abruptly at the end of its movement to cause the movement of the water or reagent away from the microscope slide.

In an alternate embodiment, the removal of a reagent can be at a specified rpm so that most of the regent is removed by spinning, however it may be advantageous to have a small amount or residual reagent left present on the microscope slide to more easily spread out the next reagent being applied. An example is a rinse solution between reagent steps can be present as a very thin film after a low rpm spinning of the slide support. The rpm range is high enough (e.g., 500 rpm) to remove the majority of the rinse buffer but low enough not to remove all the rinse buffer and leaving enough buffer present in a thin film to spread out the next reagent being applied. The rinse buffer would have a surfactant present that would easily spread out the next reagent being applied on top of the thin film of rinse buffer remaining on the slide.

The embodiment of the present invention method of specifically removing the residual water present from the histological tissue flotation water bath on or around the microscope slide and on or around the paraffin embedded biological specimen(s) by centrifugal force is meant to infer the present invention is an automated biological processing apparatus that is fully mechanized and fully enabled by a programmable microprocessor to centrifugally dry a microscope slide and biological specimen before a de-waxing or de-paraffinizing step and further processes and stain the biological specimen with any of the listed embodiments of this disclosure with or without a heat option prior to de-waxing or a de-paraffinizing step.

The method(s) of the present invention describe herein will be also known as "paraffin section drying protocol," "wet paraffin section drying protocol" "flotation liquid removal protocol," "flotation liquid removal process," "flotation liquid removal method," "biological flotation liquid removal protocol," "flotation water bath liquid removal protocol," "histological flotation water bath water removal protocol," "biological specimen flotation liquid removal protocol," "flotation water removal protocol," "histological flotation liquid removal method," "histological flotation liquid removal protocol," "histological flotation liquid removal process," "tissue flotation liquid removal method," "tissue flotation liquid removal protocol," and "tissue flotation liquid removal process." The "paraffin section drying protocol" features spinning the side support element with microscope slide thereon (with biological specimen attached to the microscope slide) to remove the histology floatation water from under the paraffin embedded biological specimen and additionally removing any residual histology floatation water from the microscope slide by spinning the slide support inside the reaction compartment therefore drying the microscope slide and paraffin biological specimen. This "paraffin section drying protocol" causes the paraffin biological specimen to come in a more close, complete, and effective contact with the positive charged microscopes slide's silane functional groups to more securely attach the paraffin biological specimen to the microscope slide. The "paraffin section drying protocol" does not use any type of heat to dry or evaporate the histology flotation water from underneath the paraffin section or dry or evaporate the residual water present on the microscope slide. The "paraffin section drying protocol" is free from a heat step to dry the paraffin section and dry the microscope slide. Drying from the "paraffin section drying protocol" is from spinning not from heating. After the "paraffin section drying protocol," a heat protocol can be used, as an option, to melt the spin dried paraffin section before a de-waxing step. The "paraffin section drying protocol" is absent an evaporative heat step for drying the residual water present under the paraffin section and possible residual water present on the microscope slide from a recently floated paraffin section from a histology floatation water-bath or other histology floatation protocol using a liquid to "float" a paraffin section onto a positive charged microscope slide.

An alternate embodiment of the present invention method and apparatus of specifically removing a floatation liquid present from at least one microscope with at least one paraffin embedded biological specimen floated thereon by centrifugal force, rotation, or spinning of at least one microscope slide and at least one paraffin embedded biological specimen floated on the at least one microscope slide is a automated biological processing apparatus that is fully mechanized to remove at least a floatation liquid from at least one microscope slide with at least one biological specimen floated thereon. The automated biological processing apparatus can further have, if desired, at least one other embodiment or embodiment step, described herein, incorporated with the automated biological processing apparatus and/or have at least one other processing step incorporated with the automated biological processing apparatus that is known in the art of processing at least one microscope slide with at least one paraffin embedded biological specimen floated thereon.

An alternate embodiment of the present invention method of specifically removing the residual water present from the histological tissue flotation water bath on or around the microscope slide and on or around the paraffin embedded biological specimen(s) by centrifugal force is meant to infer the present invention is an automated biological processing apparatus that is fully mechanized and fully enabled by a programmable microprocessor to centrifugally dry a plurality microscope slides and biological specimens before a de-waxing or de-paraffinizing step and is a standalone instrument that only dries the microscope slide and biological specimen before a de-waxing or de-paraffinizing step with or without a heat option prior to de-waxing or a de-paraffinizing step.

An alternate embodiment of the present invention method of specifically removing the residual water present from the histological tissue flotation water bath on or around the microscope slide and or biological specimen and on or around the paraffin embedded biological specimen(s) by centrifugal force is meant to infer the present invention is an automated biological processing apparatus that is fully mechanized and fully enabled by a programmable microprocessor to centrifugally dry a plurality microscope slides and biological specimens before a de-waxing or de-paraffinizing step and utilizes any other embodiments in combination of disclosed embodiments of this disclosure. Meaning, the present invention can have the ability to dry a plurality of slides and biological specimens centrifugally before a de-waxing or de-paraffinizing step with or without a heated step and perform automated pressurized antigen recovery without the ability to further stain the slide, therefore enabling this particular apparatus to be a centrifugal slide dryer, de-waxing, hydration, and antigen recovery instrument only. Any combination of embodiments can be added to the centrifugal drying apparatus to enable a automated apparatus having all the embodiments of this disclosure. An example being an automated apparatus of the present invention can have centrifugal drying, pressurized antigen recovery, staining, coversliping, etc. or any other combination of embodiments of the present disclosure that would enable a fully automated biological specimen processing apparatus.

An alternate embodiment of the present invention apparatus and method of specifically removing the residual water present from the histological tissue flotation water bath or floatation liquid on or around at least one microscope slide and on, under, or around at least one paraffin embedded biological specimen(s) by centrifugal force, spinning, or rotating is meant to infer the present invention is an automated biological processing apparatus and method that is fully mechanized and fully enabled by a programmable microprocessor to remove the flotation liquid from the microscope slide and from underneath the paraffin embedded biological specimen by rotating or spinning and can further process or stain a biological specimen as well. It is contemplated that the present invention method can or could be used in part or in combination with any of the disclosed embodiments of the present invention to process or stain a biological specimen. It is also understood and contemplated that the present invention method can or could be used in part with or incorporated into or intergraded with other microscope slide processing instruments systems know in the art to produce an improved prior art microscope slide staining apparatus or system that would benefit from the present invention method of removing a flotation liquid from between a microscope slide and a paraffin embedded biological specimen by spinning or rotating at least one microscope side with at least one floated paraffin embedded biological specimen thereon.

One embodiment of the present invention is specifically removing and/or drying the residual water present from the histological tissue flotation water bath or flotation water from a remote source on or around the microscope slide and on or around the paraffin embedded biological specimen(s) before a de-waxing or de-paraffinizing step (i.e., paraffin embedded tissue(s) or paraffin embedded cell(s)).

The flotation water bath water is in contact with the microscope slide and biological specimen at the time of floating the paraffin embedded tissue section(s) onto the microscope side.

This residual flotation bath water should be removed and/or dried from the microscope side and paraffin embedded biological specimen prior to de-waxing the paraffin section in aqueous and non-aqueous de-waxing liquids. This method of removing this residual water from the histological water flotation bath or other flotation water source other than the histological water flotation bath is novel in using centrifugal force to remove this residual water before a de-waxing or de-paraffinizing step, meaning before an initiation of a staining protocol that includes the use of de-waxing liquids as the first step of a liquid staining protocol.

The prior art is silent in the use of centrifugal force to specifically remove residual water on or around a microscope slide and paraffin section biological specimen from the flotation water or liquid flotation methods known in the art to float or mount a paraffin embedded biological specimen section to a analytic plate or microscope side prior to subjecting the paraffin embedded biological specimen to a liquid de-waxing protocol.

In one embodiment, the method of the present invention is directed to removing the residual water or liquid present from the histological tissue flotation water or liquid on or around the microscope slide and on or around the paraffin embedded biological specimen(s) by centrifugal force before or prior to a de-waxing or de-paraffinizing step before the paraffin biological specimen can be further stained by know methods in the art. These methods can include but are not limited to histological stains, histochemical stains, immunohistochemical stains, in-situ hybridization protocols for RNA, mRNA, and DNA.

The alternate method of the present invention of specifically removing the residual water present from the histological tissue flotation water bath on or around the microscope slide and on or around the paraffin embedded biological specimen(s) can further utilize heat before, during, or after the centrifugal mechatronics have been initiated by the apparatus programmable microprocessor to melt the paraffin associated with the paraffin embedded biological specimen prior to placing a liquid de-waxing reagent in contact with the microscope slide and/or paraffin embedded biological specimen.

The alternate method of the present invention of centrifugally removing the residual water present from the histological tissue flotation water bath on or around the microscope slide and on or around the paraffin embedded biological specimen(s) is the method of centrifugally removing the residual water and absent a heated paraffin melting step prior to placing a liquid de-waxing reagent in contact with the microscope slide and/or paraffin embedded biological specimen, wherein the paraffin section is not subject to a heating step or paraffin melting step prior to contact with a de-waxing reagent.

The alternate method of the present invention of centrifugally removing the residual water present from the histological tissue flotation water bath on or around the microscope slide and on or around the paraffin embedded biological specimen(s) is the method of centrifugally removing the residual water with a heated paraffin melting step after centrifugally removing the residual water and prior to placing a liquid de-waxing reagent in contact with the microscope slide and/or paraffin embedded biological specimen.

An alternate embodiment of the present invention method of specifically removing the residual water present from the histological tissue flotation water bath on or around the microscope slide and on or around the paraffin embedded biological specimen(s) by centrifugal force further comprises the use of independently, individually, and/or simultaneously moving slide supports that can impart a centrifugal force to the microscope slide and paraffin embedded biological specimen to remove the residual water from the histological flotation water bath from the microscope slide and paraffin embedded biological specimen prior to contact of the microscope slide and/or paraffin embedded biological specimen to a liquid de-waxing reagent.

In one embodiment of operation for removing water from the histological flotation water bath away from the biological specimen and microscope slide, the operator initiates the ejection of the slide support element from the inside of the apparatus or the treatment chamber to the outside of the apparatus or treatment chamber so the slide support element is now outside the apparatus or treatment chamber in the load/unload or microscope slide placement or microscope slide removal position outside the apparatus (similar in method and device of an ejected CD-ROM drive drawer, tray, or door on a personal computer to place or remove a Compact Disk on the CD-ROM drawer, tray, or door). The operator initiates the slide support eject protocol by pressing a button at the opening of the slide support element and or reaction compartment opening (located on the external faceplate of the reaction module) or initiating the proper icon or button (i.e., slide support eject button or icon) on the microprocessor screen to move or eject the slide support outside of the apparatus or treatment chamber to the microscope side load or microscope slide unload position. A "wet" microscope slide with its newly floated "wet" paraffin section biological specimen thereon is now placed on the slide support element and the operator can now gently push in the slide support element until the automatic retract feature is activated and the mechatronic devices are activated to automatically retract the slide support into the apparatus or treatment chamber to the treatment position inside the apparatus or treatment chamber (similar to a CD-ROM drive drawer, tray, or drawer automatic movement sensing feature). The operator can also push the appropriate button (i.e.—slide support retract button) near the slide support element or reaction compartment opening (located on the external faceplate of the reaction module) or by activating the appropriate icon or button (i.e.—slide support retract button or icon) on the microprocessor screen.

The "paraffin section drying protocol" is now initiated and the slide support element will begin to spin at a selected RPM that can centrifugally remove the water from the histological flotation water bath that is on the microscope side and the histological flotation water bath water that is trapped between the paraffin section and microscope slide. The slide support spins inside the reaction compartment and the water present on the microscope slide, biological specimen, slide support, and under the biological specimen is centrifugally moved away from the microscope slide, biological specimen, and slide support and is caught by the reaction compartment's inner wall. The slide support remains spinning for a timed protocol to efficiently and effectively dry the microscope slide, biological specimen, and slide support. The time of initial spinning to a dried slide, specimen, and slide support is in the range of 1 second to 1 minute of spinning and more preferably 1 second to 30 seconds spin time. The slide may be heated by any of the heating devices describe in this specification before, during or after spinning. The preferred embodiment for heat is the heating means protocol is activated after spinning and removal of the water present around the microscope slide, biological specimen, and slide support. Heating the paraffin section and melting the paraffin around and in the specimen, after the water is removed from biological specimen and microscope slide, is one way of heating and melting the paraffin biological specimen. In an alternative embodiment, the paraffin section may not be heated (paraffin melting) prior to de-waxing because the paraffin section is now dried do to spinning. A alternate embodiment is the spin dried biological specimen can be de-waxed without a paraffin melting protocol (i.e., heating step) prior to a de-waxing protocol whether the de-waxing protocol requires heat or the de-waxing protocol doesn't require heat.

A further method and apparatus embodiment of the present is the apparatus features programmability of the microprocessor or computer so the apparatus can be programmed with a staining protocol, that has any staining protocol feature described in this application, as well as, any staining protocols that are know in the art of automated staining protocols for biological specimens, which would include the "paraffin section drying protocol," of the present invention, which would feature a complete processing protocol integrated with a complete staining protocol that may also include any pre-treatment steps (i.e., antigen unmasking (pressurized/non-pressurized antigen unmasking), enzymatic treatments, primary antibody and detection regents, and final cover slipping with a thermoplastic resin) and all related processing steps (staining or otherwise processing the biological specimen) as one single complete protocol that is programmed via the microprocessor and features an initiation step by the user to "start" the programmed protocol once the wet, partially wet, or even air dried microscope slide with biological specimen attached is place onto the independently moving single side support for processing. The entire protocol which would include the first processing step of the "paraffin section drying protocol" followed by the heating step to melt the paraffin and subsequent processing of the paraffin section with a de-waxing liquid to remove the paraffin and all the remaining steps of processing the biological specimen to the final step of processing are carried out automatically with no user intervention once the protocol is initiated. Variation of any step of the protocol can be programmed before initiation of the protocol by the user. The entire programmed protocol can utilize "optical character recognition" technology known in the art of indentifying microscope slide and reagent that are loaded onto the apparatus to run the staining protocol.

Rotating or Spinning Terms Defined and Numerical Example of Rotating or Spinning a Microscope Slide:
Radius (R)=0.0127 meters (radius of a microscope slide is 0.5 inches)
Angular Velocity (Ω)=2000 rotation per minute
Tangential Velocity (V)=2.659 meters/second
Centripetal Acceleration (A)=557 meters/second^2
Radius from the center of rotation.
Angular Velocity or "spin rate."
Tangential Velocity or "rim speed."
Centripetal Acceleration or "gravity level."

Example

Floatation Liquid Removal Protocol with NO Heat

1) Float the paraffin embedded biological specimen from the histological floatation water bath (or other histological flotation liquid method) onto a positive charged microscope slide.
2) Immediately place the microscope slide onto a slide support element of the apparatus.
3) Initiate the start mode for the floatation liquid removal protocol and staining protocol of the microscope slide and biological specimen.
4) The microscope slide is spun in its reaction compartment in an rpm range of at least 1000 rpm up to 3000 rpm for a time of in a range from at least 1 second up to 30 seconds.
5) The floatation liquid removal protocol is now complete. The floatation liquid is removed from the microscope slide and biological specimen.
6) Automatically proceed to the de-waxing step and the remainder of the staining protocol.

Example

Floatation Liquid Removal Protocol with Heat to Melt the Paraffin

1) Float the paraffin embedded biological specimen from the histological floatation water bath (or other histological flotation liquid method) onto a positive charged microscope slide.
2) Immediately place the microscope slide onto a slide support element of the apparatus.
3) Initiate the start mode for the floatation liquid removal protocol and staining protocol of the microscope slide and biological specimen.
4) The microscope slide is spun in its reaction compartment in an rpm range of at least 1000 rpm up to 3000 rpm for a time of in a range from at least 1 second up to 30 seconds.
5) The floatation liquid removal protocol is now complete. The floatation liquid is removed from the microscope slide and biological specimen.
6) Heat the paraffin section to melt the paraffin in a time range from at least 1 minute up to 5 minutes at a temperature range from 60° C. up to 80° C.
7) Automatically proceed to the de-waxing step and the remainder of the staining protocol.

Example

Floatation Liquid Removal Protocol with NO Heat

1) Float the paraffin embedded biological specimen from the histological floatation water bath (or other histological flotation liquid method) onto a positive charged microscope slide.
2) Immediately place the microscope slide onto a slide support element of the apparatus.
3) Initiate the start the floatation liquid removal protocol and staining protocol of the microscope slide and biological specimen.
4) The microscope slide is spun in its reaction compartment in an rpm range of at least 1000 rpm up to 2500 rpm for a time of in a range from at least 1 second up to 30 seconds.
5) The floatation liquid removal protocol is now complete. The slide and biological specimen are free of any water in contact with the microscope slide and biological specimen.
6) Automatically proceed to the de-waxing step and the remainder of the staining protocol.

Example

Floatation Liquid Removal Protocol with Heat to Melt the Paraffin

1) Float the paraffin embedded biological specimen from the histological floatation water bath (or other histological flotation liquid method) onto a positive charged microscope slide.
2) Immediately place the microscope slide onto a slide support element of the apparatus.

3) Initiate the start the floatation liquid removal protocol and staining protocol of the microscope slide and biological specimen.

4) The microscope slide is spun in its reaction compartment in an rpm range of at least 1000 rpm up to 2500 rpm for a time of in a range from at least 1 second up to 30 seconds.

5) The floatation liquid removal protocol is now complete. The slide and biological specimen are free of any water in contact with the microscope slide and biological specimen.

6) Heat the paraffin section to melt the paraffin in a range from at least 1 minute up to 5 minutes at 60° C. to 80° C.

7) Automatically proceed to the de-waxing step and the remainder of the staining protocol.

Example

Floatation Liquid Removal Protocol with Staining Protocol with NO Heat for Melting Paraffin 1) Float the paraffin embedded biological specimen from the histological floatation water bath (or other histological flotation liquid method) onto a positive charged microscope slide.

2) Immediately place the microscope slide onto a slide support element of the apparatus.

3) Initiate the floatation liquid removal protocol and staining protocol of the microscope slide and biological specimen.

4) The microscope slide is spun in its reaction compartment in an rpm range of at least 1500 rpm up to 2500 rpm for a time of in a range from at least 1 second up to 30 seconds.

5) The floatation liquid removal protocol is now complete. The floatation liquid is removed from the microscope slide and biological specimen.

6) Automatically proceed to the de-waxing step and the remainder of the staining protocol.

Example

Floatation Liquid Removal/Staining Protocol with Heat Melting of Paraffin

1) Float the paraffin embedded biological specimen from the histological floatation water bath (or other histological flotation liquid method) onto a positive charged microscope slide.

2) Immediately place the microscope slide onto a slide support element of the apparatus.

3) Initiate the floatation liquid removal protocol and staining protocol of the microscope slide and biological specimen.

4) The microscope slide is spun in its reaction compartment in an rpm range of at least 1500 rpm up to 2500 rpm for a time of in a range from at least 1 second up to 30 seconds.

5) The floatation liquid removal protocol is now complete. The floatation liquid is removed from the microscope slide and biological specimen.

6) Heat the paraffin section to melt the paraffin in a range from at least 1 up to 5 minute in a temperature range of at least 60° C. up to 80° C.

7) Automatically proceed to the de-waxing step and the remainder of the staining protocol.

The pressure seals can be an inflatable type of seal that do not engage the reaction compartment's inner tubular wall during spinning. Under pressure these inflatable seals "inflate" to seal against the reaction compartment for pressure required protocols.

Another embodiment of the present invention apparatus and method is at least one independently moving or rotatable single microscope slide support can be attached with, captured with, held together, held together with, coupled with, or otherwise be connected at least in part with a movable or rotatable individual reaction compartment that at least in part is associated with the microscope slide support is contemplated. In this embodiment, at least one microscope slide support and at least one reaction compartment would comprise a feature that would engage or couple both the microscope slide support and its associated reaction compartment together as a unit to move or rotate together by being "captured" or "coupled" together and therefore being able to move together as a unit. This coupling feature can also be "decoupled." This coupling or de-coupling feature can be associated with the slide support or reaction compartment or both. The coupling and decoupling feature can be, for example, an inflatable seal on at least one of the slide support and reaction compartment that inflates to couple both the slide support and reaction compartment together as a unit to move or rotate together. Once coupled, the slide support and reaction compartment would move together just as if the slide support and reaction compartment were a single piece moving or rotating. When coupled, the slide support and reaction compartment move and/or rotate together completely. When decoupled, the slide support and reaction compartment can move independently in relation to each other. At least one slide support and reaction compartment can be stationary while the other is moving during a decoupled state. The couple and decouple feature can be implemented using any known way to couple and decouple items known in the art. This couple and decouple feature is completely automated and controlled by the microprocessor of the apparatus. This coupling and decoupling is at least in part a mechatronic system(s) feature of the apparatus and can utilize any mechatronic system(s) feature(s) known in the art to couple and decouple items. The couple and decouple feature can be an inflatable seal, cog, hook, latch, pin, motor, device, electromagnet, centrifugal device etc., or any other structural feature on or incorporated with at least a slide support and reaction compartment or other structure associated with at least a slide support and reaction compartment. These coupling or decoupling items, structures, parts, or apparatus structures are under the automated control of the microprocessor or computer or any other mechatronic system or mechatronic systems. This coupling and decoupling feature can also be a mechanically activated. The couple and decouple feature can be activated by the centrifugal movement alone from either the slide support or reaction compartment moving or rotating. Under centrifugal force placed on at least the slide support and reaction compartment, the coupling feature is activated and the slide support and reaction compartment are coupled and when the centrifugal force is reduced the slide support and reaction compartment decouple.

The present invention can have two separate tubular reaction compartments, a "pressure reaction compartment" that engages the seals of the slide support element against the reaction compartment to pressurize the reaction compartment and a second "spin reaction compartment" that has a larger inside diameter than the "pressure reaction compartment" so the seals do not engage the inside diameter of the 'spin reaction compartment" during spinning. These two tubular reaction compartments can be in line with each other or can collapse over one another for reduced space requirement. These reaction compartments can have a space between them when lined up in a row (in the middle between the two compartments) so that the slide support can be outside the two reaction compartments (in front or back of each compartment) and even outside the reaction compartment between each compartment (a space between the two lined up adjacent compartments) to add or remove reagents via the reagent dispensing element, reagent dispensing packs, or XYZ dispenser or any other dispensing system know in the art of dispensing reagent onto microscope slides.

The electrical connections to each individual heating element or other electrical device on or in the slide support element or reaction compartment can be controlled by wireless connections, Bluetooth® connections, impedance connections, or any other type of wireless connection to enable the free movement of the slide support element and reaction compartment in any direction or speed or speed of movement thereof. For example, the individual heating element that is part of the slide support element can be connected to the microprocessor wirelessly by those connections known in the art of connecting electrical devices wirelessly. This wireless connection of the individual heating element can thus be maintained when the slide support element or reaction compartment are in motion, for example, this enables maintenance of the heating current to the individual heating element when the slide support element is spinning while removing reagents by centrifugal force.

The reaction compartments and/or the slide support elements of the invention optionally are disposable. The disposable slide support element can be constructed of plastic or polymers that can support a microscope slide and be able to withstand the temperature and pressure requirements of the present invention. Pressures of 25-30 psig and temperatures of 100-160° C., for example, are possible with modern plastics, thermoplastics, and polymers. In one embodiment, the disposable slide support element is constructed without a heating element, rather the heating element used to heat the reagent to the above mentioned temperatures is placed within the walls of the reaction compartment rather than in the slide support element. A disposable reaction compartment is also contemplated. The disposable reaction compartment can be constructed using the same materials as said disposable slide support element. Heating elements for heating the microscope slide could be, for example, heaters that can be present outside of the disposable reaction compartment or disposable slide support element. In one embodiment, the heating element can be tubular and can contain, in its center, a disposable reaction compartment in a tubular shape. The walls of such a tubular heater could heat the tubular reaction compartment and thus heat the reagent associated with the slide support element. After a microscope slide has been treated the disposable slide support element, and/or the disposable reaction compartment can be removed from the apparatus and discarded. A new disposable reaction compartment can then be placed into the tubular heater and/or a new disposable slide support element can be placed in the staining apparatus for use. All the motions and controls of the present invention can be utilized with this embodiment of disposable reaction compartments and disposable slide support elements.

Other aspects of the present invention are shown and described in U.S. Pat. Nos. 6,534,008; 7,951,612; and 8,486,335, the entirety of each of which is hereby expressly incorporated herein by reference.

The heating element or plate of the slide support elements can be slightly smaller than the width of a microscope slide to facilitate remove of the slide from the heating plate. The width of the heating plate can be 1-6 millimeters, for example, less than a microscope slide width. A standard microscope slide is about 25 mm in width. The heating plate can be 23 mm, for example, in width to facilitate removal of the microscope slide off the heating plate.

The slide support element can have an ejection means such as a movable pin or lever underneath the microscope slide to push up a portion of the slide to facilitate removal of the microscope slide from the heating plate. These ejection means can be underneath one or more corners of the microscope slide for example. This movement can facilitate the cleaning underneath the microscope slide, removal of the microscope slide, or cooling of the microscope slide by moving the slide away from the heating plate.

The heating plate can have holes present for vacuum or pressure to be applied to the bottom of the microscope slide. Pressure exerted from these holes can push up the microscope slide to help remove the slide from the heating plate. The holes can also be used to help clean residual reagent that may be trapped underneath the slide. The process of using a rinsing liquid and the use of the vacuum or pressure holes in the heating plate provides a method of cleaning and drying the underside of the microscope slide.

The staining apparatus can have automatically leveling devices, reaction components such as slide supports and reaction compartments, pins, pegs, feet, or level sensors that are under the control of the microprocessor. When the apparatus is turned on the microprocessor will determine if the entire apparatus and or each reaction component is level. If it is not level or needs to be adjusted the leveling devices (stepper motors, pneumatic, electromechanical devices) in each leveling device, slide support, reaction compartment, pins, pegs, feet are moved in or out to level the entire apparatus or each reaction component. This is especially important when using the field models since they are moved more frequently. The main microprocessor can determine if the entire apparatus or each staining module is level each time the apparatus is turned on or a "level" icon can be available on the master microprocessor to level or check the levels at any time during a protocol.

The staining apparatus can produce a blast of air inside the reaction compartment of agitate a reagent or liquid therein to produce an emulsion.

Mixing a reagent on the microscope slide can be by at least one gas source blowing across the slide to stir the reagent. Mixing can occur by blowing at least one gas jet over the reagent and subsequently moving the slide support in at least one direction to agitate or mix a reagent or rinse a slide. Mixing is very efficient because the present invention utilizes agitated rinse or kinetic rinsing to dislodge unbound reagents from the biological specimen or the microscope slide. The kinetic movement can be by gas, physical movement of the slide, vibrations, agitation, ultrasound, etc. Kinetic movement can be for mixing or rinsing.

There can be a separate individual camera present on the outside front wall of each staining apparatus of the apparatus to see the label end of the microscope side or reagent pack information more clearly or increase the visual size of the microscope labeled end or reagent pack information. The camera can, for example, inversely project its image to improve viewing of the label end of the microscope slide for better identification of the name of the stain desired.

The reagent pack can have a RFID (radio frequency identification) tag or device for the apparatus to automatically identify the reagent pack and protocol program.

The apparatus can use non-refrigerated reagent packs for field and lab use to reduce necessary refrigeration space.

The reagent container, capsule, or vial can line up to the reagent conduit on the reaction compartment or window, or over the microscope slide and a vacuum can pull the reagent out of the capsule or vial without using the dispensing element to push the reagent out. The vacuum pulls the reagent out and the reagent drips onto the microscope slide.

There can be a plurality of movable reagent conduit lines each having a magnetic end to connect the reagent conduit line to the metal reagent conduit positioned on the reaction compartment. One of the heads on the at least one X-Y-Z positioning device can have a plurality of these movable reagents lines with magnetic couple ends to service one or a plurality of reaction compartment simultaneously with a remote reagent from a reagent container or bulk reagent bottle.

The X-Y-Z positioning device can be constructed so as to be able to pick up different types of spreading devices from a supply station and use them on the microscope slide to spread reagents. When the reagent is spread across the slide, the dispensing head, carrying the spreading device, can move to an ejection area to eject the used spreading device and can return to the supply station to pick up a new spreading device.

The X-Y-Z positioning device can be of any type known in the art of dispensing reagents. There can be one or a plurality of X-Y-Z positioning devices that can move independently to reagent supply stations or spreading device supply stations to pick up and dispense reagents from a remote source inside the staining apparatus or outside the staining apparatus.

A wet, recently floated, tissue section on a microscope side can be placed onto a slide support element and is moved into an individual reaction compartment or common pressurization chamber to apply pressure to the tissue section to further flatten out the section to the microscope slide before, during, or after the heat plate is turned on to melt the paraffin and securely attach the tissue or biological specimen to the microscope slide.

The microscope slide once stained can be coverslipped by a dry film adhesive glass coverslip by applying a solvent to the slide then tilting the slide support element at an angle to the coverslip dispenser and then the coverslip is touched at one edge to the microscope side and the slide support is moved back to horizontal placing the coverslip on the slide. The heating plate is turned on to dry the coverslip prior to removal of the slide for examination under a microscope.

The present invention contemplates that the microscope slides and reagents used herein can be heated by magnetic induction. This embodiment would be in the place of wired heating elements in the individual reaction compartment and individual slide support element. The reaction compartment and or slide support element would have metal associated therewith for magnetic induction heating.

Magnetic Induction heating is the process of heating an electrically conducting object, like a metal, by electromagnetic induction. Electromagnetic induction heating is the production of voltage across a conductor situated in a changing magnetic field or a conductor moving through a stationary magnetic field (Faraday's Law). This changing magnetic field generates eddy currents within the metal and the resistance leads to Joule heating of the metal. This type of heater is known, for example, in the art of cooking ranges and cook top surfaces (Waring Pro SB-30, Pro ICT100, Waring Products 314 Ella T. Grasso Avenue, Torrington, Conn. 06790). An induction heater (for heating a reagent on or around the biological specimen or just the biological specimen) consists of an electromagnet, through which a high-frequency alternating current (AC) is passed. Commercial power line frequency is acceptable to induce the primary inductor or electromagnet. Heat may also be generated by magnetic hysteresis losses in materials that have significant relative permeability. The frequency of AC used depends on the object size, material type, coupling (between the work coil and the object to be heated) and the penetration depth. Magnetic induction works best with cast iron, steel, stainless steel, ferrite based metal(s) and any coated metal of these types. The cast iron, steel, stainless steel, ferrite based metal(s) can be coated or intergraded with glass, ceramic or enamels, for example to have excellent anti-corrosive properties. Any coating known in the art of metal coating that can be heated can be use and are contemplated. Copper to some degree can be used. Magnetic induction heating doesn't heat non-metal objects. The primary inductor (electromagnet) would be positioned around the metal slide support element heating plate, or any other metal associated with a slide support, reaction compartment, common camber, reagent support, reagent containers, reagent conduits, etc. The metal slide support element or metal heat plate, or magnetic induction inducible heating material, for example, is heated by a commercial power line frequency (current) induced in it by a primary inductor (electromagnet). This type of heating of any metal present in the staining apparatus that is required to be heated to transfer (conduction heating) the heat to a reagent or just the biological specimen is advantageous in the present invention. Just the metal in the reaction compartment and slide support element would get hot to heat the reagent. The individual reaction compartment can be constructed of metal, metal and glass, metal and ceramic, or metal and a plastic polymer for use with a magnetic induction heating device. The individual slide support element can be constructed of metal, metal and glass, metal and ceramic, or metal and a plastic polymer for use with a magnetic induction heating device. Since the present invention has independently moving processing components (i.e., independently moving slide supports, independently moving reaction compartments, independently moving reagent supports, etc.) this method of heating doesn't require hard electrical wiring to each heater or heaters. This use of magnetic induction to heat reagents or the biological specimen or both, reduces the clutter and cost of hard wiring each heater(s) of the present invention. Each reaction module or staining module can have at least one separate independently working magnetic inductor to heat an electromagnetic inducible metal that can then conductively transfer its heat to a reagent or biological specimen for a particular heat requiring protocol. There may also be more than one magnetic inductor for heating more than one metal source of the reaction module or staining module. The heated plate(s) or heated metal that is heated by Joule heating is extremely fast, controllable, and efficient. The heated metal plates or heated metal structures can be regulated in the range of less than 1° C. to exceeding 1000° C. More preferable the temperature regulation can be in the range of 20° C. to 180° C., depending on the heating requiring protocol. Any processing device can be constructed of an electromagnetic inducible metal and can have any shape. Shapes made of an electromagnetic inducible metal like tubes, plates, pins, ducts, dispensers, supports, of all types of shapes and construction are known and are contemplated. The processing devices of the present invention would be constructed mostly of non-metal materials and only the heating areas being constructed of an inducible material like metal. The microprocessor can regulate the temperature of any electromagnetically-inducible metal by adjusting the voltage or current to the at least one primary inductor (electromagnet) therefore regulating the electromagnetic inducible metal(s) (i.e., slide support element, heat plate, reaction compartment heated wall(s), reagent strip support heater, reagent containers heater, etc.) temperature associated with each component of the staining apparatus. It is known that any and all type of heating method along with magnetic induction heating is contemplated and any combination of these types of heaters (i.e.—infra red, conductive, convection, radiant, foil, kapton, conductive inks, magnetic induction, microwaves, etc.) can be used in each slide support element or reaction compartment. The electromagnetically inducible metal(s) can be quickly cooled once the primary inductor is turn off, because it is not necessary to wait for the heating means to cool down as well. When the electromagnetic induction is turned off the heat stops generating at the inducible metal site and the cooling process starts immediately without having to wait for the heating source (i.e., electromagnetism) to cool down along with the heated inducible metal. Just the inducible metal is cooled alone. This is in stark contrast for the cooling method of a conventional conduction heat source which requires the cooling of the conduction heat source in lockstep with its heated plate. The reaction compartment can be made entirely of glass or ceramics as to not be heated by the magnetic induction heating device. The inside of the reaction compartment can be engineered to be the magnetic induction heating device that heats the slide support element metal heat plate or the entire slide support element if it was constructed of metal. The advantage to this is the outside of the reaction compartment can remain cool to the touch and only the slide support element or slide support would be heated by the magnetic induction device to heat the reagent present on or associated with the microscope side. A user can place a bench unit, field unit, or small scale version of the staining apparatus (e.g., comprising 5-15 reaction compartments) near their microtome or processing table during preparation of a microscope slide once the tissues is floated onto the microscope slide the user can press the individual slide support element's eject/insert button and the individual slide support element inside the staining apparatus would then automatically move out of the staining apparatus and the user could then place the wet microscope slide onto the individual slide support element. The user could then press the appropriate button on the staining apparatus to cause the electromagnet to induce the individual slide support element metal plate directly under only the microscope slide to start heating the microscope slide with biological specimen attached. The slide support element metal plate would be heated causing heating of the microscope slide thereon without heating the remainder of the slide support element because it is constructed from a non-metal material like glass, for example. If the user would accidently touch the slide support element he or she would not feel the heat because only the heating plate of the slide support element and microscope slide thereon are being heated and the majority of the slide support elements mass (i.e., glass slide support) is not heated. The user can then let the slide support element stay outside the staining apparatus or move the slide support element into the staining apparatus by slightly pushing in on the slide support element to activate the automated movement of the slide support element into the staining apparatus. The user can alternatively press the eject/insert button again to automatically move the slide support element into the staining apparatus without pushing in on the slide support element. This movement is similar to a CD-ROM drawer or door on a personal computer and is described in detail elsewhere in this application. Once all of the microscope slides are placed on their individual slide support elements the user would move all the slide support elements into the staining apparatus either by pushing each individual eject/insert button for each slide support element or press the appropriate icon to move all the open slide support elements into the staining apparatus at the same time. There are icons and buttons present on the staining apparatus to move just one slide support element out of the staining apparatus and into the staining apparatus or move all the slide support elements together out of the staining apparatus or into the staining apparatus. An alternate embodiment of the present invention using magnetic induction heating is the use of a disposable individual slide support element and or a disposable individual reaction compartment or both that has at least one area being metal or an inducible metal or material that can be heated by magnet induction is contemplated. A further example is the use of a metal pan or inducible material in the cavity of the slide support element or the metal pan or inducible material in the head space of the reaction compartment. The magnetic induction heating device would then only heat the metal pan or inducible material in the slide support element, therefore heating D.I. water, for example, in the metal pan to produce steam that would pressurize the reaction compartment and heat the reagent on or associated with the biological specimen on the microscope slide. The method of magnetic induction heating contemplated herein is preferred because it can be controlled precisely depending on the amount of heat required and the amount of steam being generated to produce the desired level of pressurization without the necessity of releasing of the pressure being produced by steam generation to control pressure level. The magnetic field can be adjusted to regulate the heat temperature of the metal pan therefore increasing or decreasing the pressure contained in the reaction compartment for pressure regulation. Any combination of metal and non-metal in the construction of the individual reaction compartment or individual slide support element is contemplated. A magnetic induction heating device can be in or around the individual reaction compartment and/or in or around the individual slide support element. Magnetic induction can be used as long as there is metal or an inducible material either in the reaction compartment and/or metal present in the slide support element that can be heated by a magnetic induction heating device. The pressurizable common chamber can also employ magnetic induction to heat the walls of the pressurizable common chamber and or the metal slide support elements or areas requiring heating by magnetic induction of a metal or inducible material inside the pressurizable common chamber.

The staining apparatus can be relatively small, having just 5-20 sets of reaction components for example. This compact "point of use" staining apparatus can be positioned at the microtome or cryostat. A user can place wet microscope slides with their newly floated tissue section attached or frozen tissue attached onto the staining apparatus at the point of microtomy. Once the slides have been placed onto the staining apparatus, the apparatus can be moved to an area for staining the slides or just left near the microtome or cryostat to start the staining process. The automated leveling feature (described elsewhere in this application), of the present invention, can "level" the staining apparatus prior to staining or treatment initiation. The user needs only the reagent pack for each particular slide protocol to be placed into or onto the reagent pack support device and start the protocol. The entire reagent protocol, including rinses and application of a cover-slipping mountant, can be provided by the reagent pack with no need for bulk fluid sources if desired. The entire protocol from start to finish is preferably supplied from the reagent pack. If the apparatus requires bulk fluid sources, the apparatus can have attached bulk fluids in containers that can be small and quickly refillable without stopping the staining apparatus because the bulk fluid containers can be linked together in a series or parallel for quick removal, filling, or disposal of bulk reagents and bulk waste.

The staining apparatus in one embodiment is adapted for pressurized pre-treatment only. It is constructed so as to perform only High Pressure Epitope Retrieval (HiPer™) pretreatments without further staining the slide. This HiPer™ apparatus can perform "Heat Induced Epitope Retrieval" (HIER) and or High Pressure Epitope Retrieval (HiPer™) pretreatment protocols. This embodiment is useful in particular when labs have an existing manual or automated staining platform or system that needs the added benefit of quick and efficient high temperature pre-treatment protocols prior to placing slides onto their existing automated or manual staining systems. The HiPer™ apparatus can use reagent packs for different types of heat induced epitope retrieval solutions or bulk fluid containers for use with the ports in each reaction module. The HiPer™ apparatus can move individual slides into and out of a pressurizable common chamber without leakage of the pressure contained in the pressurizable common chamber. The HiPer™ apparatus features Independent Access™, the mechanics of which are described elsewhere in this application.

The HiPer™ apparatus can also be adapted to move a plurality of slides on a single slide support device into and out of a pressurizable common chamber for a pre-treatment under pressurization, prior to further staining. A plurality of slides movable on a common support can be moved into and out of the pressurizable common chamber. The plurality of slides is moved into the inner space of the common chamber; a reagent can be dispensed onto each individual microscope slide either independently or simultaneously. This apparatus can use reagent packs or dispense reagents from a bulk reagent solution container by ports such as dispenser elements described elsewhere in this application. The pressurizable common chamber is closed and is subjected to pressure and heat to treat the biological specimen on the microscope slide. The heating means and pressurization means are explained elsewhere in this application. The reagent on or associated with the biological specimen is preferable on only the microscope slide.

The staining apparatus of the invention, in any embodiment described herein, can have a hand held or stationary scanner like IRISPen™ Express 6 (I.R.I.S. Group s.a. 10 rue du Bosquet, B-1348, Louvain la Neuve, Belgium) or any scanner or digitizer that can "scan" the entire microscope slide before, during and or after the biological specimen has been processed. Any scanner or digitizer known in the art can be used. This scanner or scanners provides information to the exact location or the position of the biological specimen (i.e., tissues section(s)) on the microscope slide in relation to the frosted, Colormark™, Colorfrost™, or otherwise labeled end of the microscope slide. The scanner can also use or store the information provided on the labeled end. The scanner can scan before, during, or after the slide is stained to store information to give the user the digital account of the entire staining protocol that can be stored in memory of the microprocessor and be retrieved at a later date for evaluation. The stored information can be for any OCR code or codes on the slide's labeled end along with the digital image of the biological specimen before, during, and after the completed processing or staining. The scanner may also be inside the staining apparatus and is movable inside the staining apparatus such as described previously in regard to the X-Y-Z processing device. Further each set of reaction components can have an independently moving scanner specific to only one set of reaction components. The scanner(s) can be stationary and the slide support element is movable to provide the scanning motion. The scanner can be inside the staining apparatus or outside the staining apparatus or both. There is at least one scanner present for the staining apparatus to capture digital images of the biological specimen on the microscope slide and the labeled end of the microscope slide, an example being, the tissue section can be scanned and the staining apparatus detects where the biological specimen is positioned relative to the labeled end of the microscope slide. The staining apparatus can now more effectively and efficiently dispense or treat only the area of the microscope slide the biological specimen occupies. The location, area used by the biological specimen, and biological specimen(s) information (i.e., size, area, pieces of tissue(s) present, cells, agglutination patterns, color, texture, inking colors for margin identification, etc.) along with the information collected from any OCR code, machine readable code(s), letters, numbers, symbols, written information, etc. present on the labeled end of the microscope slide can be compiled, calculated, arranged, digitally stored, and retrieved for later analysis.

While the invention has been described herein in connection with certain embodiments so that aspects thereof may be more fully understood and appreciated, it is not intended that the invention be limited to these particular embodiments. On the contrary, it is intended that all alternatives, modifications and equivalents are included within the scope of the invention as defined by the appended claims. Thus the examples and embodiments described herein, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

Changes may be made in the construction and the operation of the various components, elements and assemblies described herein or in the steps or the sequence of steps of the methods described herein without departing from the spirit and scope of the inventive concepts disclosed and claimed herein.

What is claimed is:

1. A method of removing a floatation liquid from between a microscope slide and a paraffin embedded biological specimen, the method comprising:
   positioning at least one microscope slide with at least one paraffin embedded biological specimen floated thereon onto a slide support element;
   positioning the microscope slide with the paraffin embedded biological specimen floated thereon in a reaction compartment; and
   rotating the slide support element within the reaction compartment so as to cause the microscope slide and the paraffin embedded biological specimen to move in a way that causes substantially all of the floatation liquid disposed between the microscope slide and the paraffin embedded biological specimen to be drawn from between the microscope slide and the paraffin embedded biological specimen.

2. The method of claim 1, wherein the slide support element is rotated at a rate and for a time period sufficient to cause all the floatation liquid disposed between the microscope slide and the paraffin embedded biological specimen to be drawn from between the microscope slide and the paraffin embedded biological specimen.

3. The method of claim 2, wherein the step of rotating the slide support element further comprises rotating the slide support element at a rate in a range of from about 1300 rpm to about 2300 rpm for a period of time ranging from about 1 second to about 60 seconds.

4. The method of claim 2, wherein the step of rotating the slide support element further comprises rotating the slide support element at a rate in a range of from about 1300 rpm to about 2500 rpm for a period of time ranging from about 1 second to about 20 seconds.

5. The method of claim 1, wherein the slide support element has a longitudinal axis, and wherein the step of rotating the slide support element further comprises rotating the slide support element about the longitudinal axis of the slide support element while maintaining the longitudinal axis in a stationary position.

6. The method of claim 5, wherein microscope slide has a longitudinal axis, and wherein the step of positioning the microscope slide on the slide support element further comprises positioning the microscope slide onto the slide support element so that the longitudinal axis of the microscope slide is substantially aligned with the longitudinal axis of the slide support element.

7. A method of treating a paraffin embedded biological specimen, comprising:
  floating at least one paraffin embedded biological specimen onto at least one microscope slide with a flotation liquid;
  positioning the microscope slide with the paraffin embedded biological specimen floated thereon onto a slide support element; and
  rotating the slide support element to cause the microscope slide and the paraffin embedded biological specimen to turn in a way that causes substantially all the floatation liquid disposed between the microscope slide and the paraffin embedded biological specimen to be drawn from between the microscope slide and the paraffin embedded biological specimen.

8. The method of claim 7, further comprising the step of positioning the microscope slide with the paraffin embedded biological specimen floated thereon in a reaction compartment prior to rotating the slide support element.

9. The method of claim 8, wherein the slide support element is rotated at a rate and for a time period sufficient to cause all the floatation liquid disposed between the microscope slide and the paraffin embedded biological specimen to be drawn from between the microscope slide and the paraffin embedded biological specimen.

10. The method of claim 7, further comprising de-paraffinizing the paraffin embedded biological specimen after drawing the floatation liquid from between the microscope slide and the paraffin embedded biological specimen.

11. The method of claim 10, further comprising initiating an antigen unmasking protocol after the de-paraffinizing step.

12. The method of claim 11, further comprising initiating a staining protocol after completing the antigen unmasking protocol.

13. The method of claim 7, further comprising the step of heating the paraffin embedded biological specimen to a temperature sufficient to melt the paraffin.

14. The method of claim 10, further comprising the step of de-paraffinizing the paraffin embedded biological specimen absent melting the paraffin with heat.

15. The method of claim 10, further comprising initiating a staining protocol after the de-paraffinizing step.

16. The method of claim 7, further comprising the steps of: after drawing the floatation liquid from between the microscope slide and the paraffin embedded biological specimen, heating the paraffin embedded biological specimen to a temperature sufficient to melt the paraffin, and treating the paraffin embedded biological specimen with a de-paraffinizing reagent.

17. The method of claim 7, wherein the slide support element has a longitudinal axis, and wherein the step of rotating the slide support element further comprises rotating the slide support element about the longitudinal axis of the slide support element while maintaining the longitudinal axis in a stationary position.

18. The method of claim 17, wherein microscope slide has a longitudinal axis, and wherein the step of positioning the microscope slide on the slide support element further comprises positioning the microscope slide onto the slide support element so that the longitudinal axis of the microscope slide is substantially aligned with the longitudinal axis of the slide support element.

19. A method of treating a plurality of paraffin embedded biological specimens, comprising:
  floating the plurality of paraffin embedded biological specimens onto a plurality of microscope slides with a flotation liquid to form a plurality of microscope slides with at least one paraffin embedded biological specimen floated thereon;
  positioning each of the microscope slides with the paraffin embedded biological specimen floated thereon onto a plurality of slide support elements, wherein each of the slide support elements is configured to support only a single microscope slide; and
  rotating the slide support elements to cause the microscope slides and the paraffin embedded biological specimens to turn in a way that causes substantially all of the floatation liquid disposed between each of the microscope slides and the paraffin embedded biological specimens to be drawn from between the microscope slides and the paraffin embedded biological specimens.

20. The method of claim 19, wherein the method further comprises the step of moving each of the microscope slides with the paraffin embedded biological specimen floated thereon into a reaction compartment prior to rotating the slide support elements.

21. The method of claim 20, wherein the step of moving each of the microscope slides with the paraffin embedded biological specimen floated thereon into a reaction compartment, further comprises moving each of the microscope slides with the paraffin embedded biological specimen floated thereon into a reaction compartment configured to receive only one microscope slide.

22. The method of claim 20, wherein the slide support elements are independently movable and rotatable relative to one another.

23. The method of claim 1, wherein the method is integrated in an automated slide staining apparatus.

24. The method of claim 7, wherein the method is integrated in an automated slide staining apparatus.

25. The method of claim 19, wherein the slide support element is rotated at a rate and for a time period sufficient to cause all the floatation liquid disposed between the microscope slide and the paraffin embedded biological specimen to be drawn from between the microscope slide and the paraffin embedded biological specimen.

26. The method of claim 25, wherein the step of rotating the slide support element further comprises rotating the slide support element at a rate in a range of from about 1300 rpm to about 2300 rpm for a period of time ranging from about 1 second to about 60 seconds.

27. The method of claim 25, wherein the step of rotating the slide support element further comprises rotating the slide support element at a rate in a range of from about 1300 rpm to about 2500 rpm for a period of time ranging from about 1 second to about 20 seconds.

28. The method of claim 19, wherein the slide support element has a longitudinal axis, and wherein the step of rotating the slide support element further comprises rotating the slide support element about the longitudinal axis of the slide support element while maintaining the longitudinal axis in a stationary position.

29. The method of claim 28, wherein microscope slide has a longitudinal axis, and wherein the step of positioning the microscope slide on the slide support element further comprises positioning the microscope slide onto the slide support element so that the longitudinal axis of the microscope slide is substantially aligned with the longitudinal axis of the slide support element.

30. The method of claim 19, wherein the method is integrated in an automated slide staining apparatus.

31. A method of treating a plurality of paraffin embedded biological specimens, comprising:
floating the plurality of paraffin embedded biological specimens onto a plurality of microscope slides with a flotation liquid to form a plurality of microscope slides with at least one paraffin embedded biological specimen floated thereon;
positioning each of the microscope slides with the paraffin embedded biological specimen floated thereon onto a slide support element; and
rotating the slide support element to cause the microscope slides and the paraffin embedded biological specimens to turn in a way that causes substantially all of the floatation liquid disposed between each of the microscope slides and the paraffin embedded biological specimens to be drawn from between the microscope slides and the paraffin embedded biological specimens.

32. The method of claim 31, wherein the slide support element is rotated at a rate and for a time period sufficient to cause all the floatation liquid disposed between the microscope slide and the paraffin embedded biological specimen to be drawn from between the microscope slide and the paraffin embedded biological specimen.

33. The method of claim 32, wherein the step of rotating the slide support element further comprises rotating the slide support element at a rate in a range of from about 1300 rpm to about 2300 rpm for a period of time ranging from about 1 second to about 60 seconds.

34. The method of claim 32, wherein the step of rotating the slide support element further comprises rotating the slide support element at a rate in a range of from about 1300 rpm to about 2500 rpm for a period of time ranging from about 1 second to about 20 seconds.

35. The method of claim 31, wherein the slide support element has a longitudinal axis, and wherein the step of rotating the slide support element further comprises rotating the slide support element about the longitudinal axis of the slide support element while maintaining the longitudinal axis in a stationary position.

36. The method of claim 35, wherein microscope slide has a longitudinal axis, and wherein the step of positioning the microscope slide on the slide support element further comprises positioning the microscope slide onto the slide support element so that the longitudinal axis of the microscope slide is substantially aligned with the longitudinal axis of the slide support element.

37. The method of claim 31, wherein the method is integrated in an automated slide staining apparatus.

38. The method of claim 31, wherein the method further comprises the step of moving each of the microscope slides with the paraffin embedded biological specimen floated thereon into a reaction compartment prior to rotating the slide support element.

39. A method of removing floatation liquid from a plurality of microscope slides and paraffin embedded biological specimens, comprising:
positioning a plurality of microscope slides with at least one paraffin embedded biological specimen floated thereon onto a slide support element; and
rotating the slide support element to cause the microscope slides and the paraffin embedded biological specimens to turn in a way that causes substantially all of the floatation liquid disposed between each of the microscope slides and the paraffin embedded biological specimens to be drawn from between the microscope slides and the paraffin embedded biological specimens.

40. The method of claim 39, wherein the slide support element is rotated at a rate and for a time period sufficient to cause all the floatation liquid disposed between the microscope slide and the paraffin embedded biological specimen to be drawn from between the microscope slide and the paraffin embedded biological specimen.

41. The method of claim 39, wherein the step of rotating the slide support element further comprises rotating the slide support element at a rate in a range of from about 1300 rpm to about 2300 rpm for a period of time ranging from about 1 second to about 60 seconds.

42. The method of claim 39, wherein the step of rotating the slide support element further comprises rotating the slide support element at a rate in a range of from about 1300 rpm to about 2500 rpm for a period of time ranging from about 1 second to about 20 seconds.

43. The method of claim 39, wherein the slide support element has a longitudinal axis, and wherein the step of rotating the slide support element further comprises rotating the slide support element about the longitudinal axis of the slide support element while maintaining the longitudinal axis in a stationary position.

44. The method of claim 43, wherein microscope slide has a longitudinal axis, and wherein the step of positioning the microscope slide on the slide support element further comprises positioning the microscope slide onto the slide support element so that the longitudinal axis of the microscope slide is substantially aligned with the longitudinal axis of the slide support element.

45. The method of claim 39, wherein the method is integrated in an automated slide staining apparatus.

46. The method of claim 39, wherein the method further comprises the step of moving each of the microscope slides with the paraffin embedded biological specimen floated thereon into a reaction compartment prior to rotating the slide support element.

47. A method of removing a floatation liquid from between a microscope slide and a paraffin embedded biological specimen, the method comprising:
positioning at least one microscope slide with at least one paraffin embedded biological specimen floated thereon onto a slide support element; and
rotating the slide support element so as to cause the microscope slide and the paraffin embedded biological specimen to move in a way that causes substantially all of the floatation liquid disposed between the microscope slide and the paraffin embedded biological specimen to be drawn from between the microscope slide and the paraffin embedded biological specimen.

48. The method of claim 47, wherein the slide support element is rotated at a rate and for a time period sufficient to cause all the floatation liquid disposed between the microscope slide and the paraffin embedded biological specimen to be drawn from between the microscope slide and the paraffin embedded biological specimen.

49. The method of claim 48, wherein the step of rotating the slide support element further comprises rotating the slide support element at a rate in a range of from about 1300 rpm to about 2300 rpm for a period of time ranging from about 1 second to about 60 seconds.

50. The method of claim 48, wherein the step of rotating the slide support element further comprises rotating the slide support element at a rate in a range of from about 1300 rpm to about 2500 rpm for a period of time ranging from about 1 second to about 20 seconds.

51. The method of claim 47, wherein the slide support element has a longitudinal axis, and wherein the step of rotating the slide support element further comprises rotating the slide support element about the longitudinal axis of the slide support element while maintaining the longitudinal axis in a stationary position.

52. The method of claim 51, wherein microscope slide has a longitudinal axis, and wherein the step of positioning the microscope slide on the slide support element further comprises positioning the microscope slide onto the slide support element so that the longitudinal axis of the microscope slide is substantially aligned with the longitudinal axis of the slide support element.

53. The method of claim 47, wherein the method is integrated in an automated slide staining apparatus.

\* \* \* \* \*

UNITED STATES PATENT AND TRADEMARK OFFICE
CERTIFICATE OF CORRECTION

PATENT NO. : 9,170,179 B2  
APPLICATION NO. : 14/216071  
DATED : October 27, 2015  
INVENTOR(S) : Lee H. Angros Page 1 of 1

It is certified that error appears in the above-identified patent and that said Letters Patent is hereby corrected as shown below:

In The Specification:

Column 59, line 26: After "specimen" delete "know" and replace with -- known --
Column 59, line 28: Delete "know" and replace with -- known --
Column 59, line 33: Before "floatation" insert -- trapped --
Column 59, line 33: After "floatation" delete "water bath trapped"
Column 60, line 1: After "turned" insert -- or --
Column 60, line 3: After "achieve" insert -- removal of --
Column 60, line 21: Before "embodiment," insert -- another --

Signed and Sealed this  
Fifteenth Day of March, 2016

Michelle K. Lee  
*Director of the United States Patent and Trademark Office*